(12) United States Patent
Madden et al.

(10) Patent No.: US 12,286,481 B2
(45) Date of Patent: *Apr. 29, 2025

(54) METHODS FOR THE TREATMENT OF THYROID EYE DISEASE

(71) Applicant: Horizon Therapeutics Ireland DAC, Dublin (IE)

(72) Inventors: David Madden, Mount Kisco, NY (US); Kathleen Gabriel, Voorhees, NJ (US); Guido Magni, Basel (CH); Richard Woodward, Phoenixville, PA (US)

(73) Assignee: Horizon Therapeutics Ireland DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/929,510

(22) Filed: Oct. 28, 2024

(65) Prior Publication Data

US 2025/0051461 A1 Feb. 13, 2025

Related U.S. Application Data

(63) Continuation of application No. 17/531,365, filed on Nov. 19, 2021, now Pat. No. 12,209,130, which is a continuation of application No. 16/256,221, filed on Jan. 24, 2019, now Pat. No. 11,208,489.

(60) Provisional application No. 62/716,194, filed on Aug. 8, 2018, provisional application No. 62/635,342, filed on Feb. 26, 2018, provisional application No. 62/621,201, filed on Jan. 24, 2018.

(51) Int. Cl.
| | | |
|---|---|---|
| C07K 16/28 | (2006.01) | |
| A61K 39/00 | (2006.01) | |
| A61K 39/395 | (2006.01) | |
| A61K 45/06 | (2006.01) | |
| A61P 27/02 | (2006.01) | |

(52) U.S. Cl.
CPC ...... *C07K 16/2863* (2013.01); *A61K 39/3955* (2013.01); *A61K 45/06* (2013.01); *A61P 27/02* (2018.01); *A61K 2039/505* (2013.01); *A61K 2039/545* (2013.01); *A61K 2039/55* (2013.01); *C07K 2317/21* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,572,897 B2 | 8/2009 | Graus et al. | |
| 7,579,157 B2 | 8/2009 | Graus et al. | |
| 8,153,121 B2 | 4/2012 | Smith et al. | |
| 11,208,489 B2 | 12/2021 | Madden et al. | |
| 11,208,490 B2 | 12/2021 | Madden et al. | |
| 12,209,130 B2 | 1/2025 | Madden et al. | |
| 2007/0218514 A1 | 9/2007 | Smith et al. | |
| 2016/0287611 A1 | 10/2016 | Dobak | |
| 2019/0225696 A1 | 7/2019 | Madden et al. | |
| 2019/0270820 A1 | 9/2019 | Madden et al. | |
| 2021/0284741 A1 | 9/2021 | Madden et al. | |
| 2022/0324985 A1 | 10/2022 | Madden et al. | |
| 2022/0340667 A1 | 10/2022 | Madden et al. | |
| 2024/0301072 A1 | 9/2024 | Madden et al. | |

FOREIGN PATENT DOCUMENTS

| | | |
|---|---|---|
| WO | WO 2016/064716 A1 | 4/2016 |
| WO | WO 2019/173352 A1 | 9/2019 |

OTHER PUBLICATIONS

Bagatell, R. et al., "Pharmacokinelically Guided Phase 1 Trial of the IGF-1 Receptor Antagonist RG1507 in Children with Recurrent or Refractory Solid Tumors", Clin Cancer Res., vol. 17(3), pp. 611-619 (2011).
Bahn, R. S., "Current Insights into the Pathogenesis of Graves' Ophthalmopathy", Horm Metab Res., vol. 47(10). pp. 773-778 (2015).
Bahn, R. S., "Graves' ophthalmopathy", N Engl J Med., vol. 362(8), pp. 726-738 (2010).
Bartalena, L. et al., "Consensus statement of the European Group on Graves' orbitopathy (EUGOGO) on management of GO", Eur J Endocrinol, vol. 158(3), pp. 273-285 (2008).
Bartelena, L. et al. "Efficacy and safety of three different cumulative doses of intravenous methylprednisolone for moderate to severe and active Graves' orbitopathy", J Clin Endocrinol Metab., vol. 97(12), pp. 4454-4463 (2012).
Chen, H. et al., "Teprotumumab, an IGF-1R blocking monoclonal antibody inhibits TSH and IGF-1 action in fibrocytes", J Clin Endocrinol Metab., vol. 99, pp. E1635-E1640 (2014).
Chen, X. L. et al., "Effects and Its Mechanism of IGF-1R on the Synthesis of Hyaluronic Acid in Orbital Fibroblasts of Thyroid Associated Ophthalmopathy", Sichuan Da Xue Xue Bao Yi Xue Ban, vol. 48(5), pp. 727-731 (2017).
Clinical Trials No. NCT01868997. Teprotumumab (RV 001) Treatment in Patients With Active Thyroid Eye Disease, Version 1. Reported date submitted: May 30, 2013. Date publicly available: Unknown. Date accessed: May 24, 2024. Available at https://classic.clinicaltrials.gov/ct2/history/NCT01868997?V_1=View#StudyPageTop.
Clinical Trials No. NCT01868997. Teprotumumab (RV 001) Treatment in Patients With Active Thyroid Eye Disease, Version 10. Reported date submitted: Apr. 16, 2014. Date publicly available: Unknown. Date accessed: May 24, 2024. Available at: https://classic.clinicaltrials.gov/ct2/history/NCT01868997?V_10=View#StudyPageTop.

(Continued)

*Primary Examiner* — Ruixiang Li
(74) *Attorney, Agent, or Firm* — Knobbe, Martens, Olson & Bear, LLP

(57) ABSTRACT

The invention provides a method of reducing the severity of, or treating, thyroid-associated ophthalmopathy (TAO), also known as thyroid eye disease (TED) or Graves' ophthalmopathy or orbitopathy (GO), as well as antibodies, or antigen binding fragments thereof, and pharmaceutical compositions comprising them, useful in the methods.

28 Claims, 10 Drawing Sheets

Specification includes a Sequence Listing.

(56) References Cited

OTHER PUBLICATIONS

Clinical Trials No. NCT01868997. Teprotumumab (RV 001) Treatment in Patients With Active Thyroid Eye Disease, Version 11. Reported date submitted: Jul. 29, 2014. Date publicly available: Unknown. Date accessed: May 24, 2024. Available at: https://classic.clinicaltrials.gov/ct2/history/NCT01868997?V_11=View#StudyPageTop.

Clinical Trials No. NCT01868997. Teprotumumab (RV 001) Treatment in Patients With Active Thyroid Eye Disease, Version 12. Reported date submitted: Nov. 3, 2014. Date publicly available: Unknown. Date accessed: May 24, 2024. Available at: https://classic.clinicaltrials.gov/ct2/history/NCT01868997?V_12=View#StudyPageTop.

Clinical Trials No. NCT01868997. Teprotumumab (RV 001) Treatment in Patients With Active Thyroid Eye Disease, Version 13. Reported date submitted: Nov. 13, 2014. Date publicly available: Unknown. Date accessed: May 24, 2024. Available at: https://classic.clinicaltrials.gov/ct2/history/NCT01868997?V_13=View#StudyPageTop.

Clinical Trials No. NCT01868997. Teprotumumab (RV 001) Treatment in Patients With Active Thyroid Eye Disease, Version 14. Reported date submitted: Feb. 5, 2015. Date publicly available: Unknown. Date accessed: May 24, 2024. Available at: https://classic.clinicaltrials.gov/ct2/history/NCT01868997?V_14=View#StudyPageTop.

Clinical Trials No. NCT01868997. Teprotumumab (RV 001) Treatment in Patients With Active Thyroid Eye Disease, Version 15. Reported date submitted: Mar. 6, 2015. Date publicly available: Unknown. Date accessed: May 24, 2024. Available at: https://classic.clinicaltrials.gov/ct2/history/NCT01868997?V_15=View#StudyPageTop.

Clinical Trials No. NCT01868997. Teprotumumab (RV 001) Treatment in Patients With Active Thyroid Eye Disease, Version 16. Reported date submitted: Sep. 18, 2015. Date publicly available: Unknown. Date accessed: May 24, 2024. Available at: https://classic.clinicaltrials.gov/ct2/history/NCT01868997?V_16=View#StudyPageTop.

Clinical Trials No. NCT01868997. Teprotumumab (RV 001) Treatment in Patients With Active Thyroid Eye Disease, Version 17. Reported date submitted: Oct. 3, 2016. Date publicly available: Unknown. Date accessed: May 24, 2024. Available at: https://classic.clinicaltrials.gov/ct2/history/NCT01868997?V_17=View#StudyPageTop.

Clinical Trials No. NCT01868997. Teprotumumab (RV 001) Treatment in Patients With Active Thyroid Eye Disease, Version 18. Reported date submitted: Nov. 15, 2016. Date publicly available: Unknown. Date accessed: May 24, 2024. Available at: https://classic.clinicaltrials.gov/ct2/history/NCT01868997?V_18=View#StudyPageTop.

Clinical Trials No. NCT01868997. Teprotumumab (RV 001) Treatment in Patients With Active Thyroid Eye Disease, Version 19. Reported date submitted: Nov. 23, 2016. Date publicly available: Unknown. Date accessed: May 24, 2024. Available at: https://classic.clinicaltrials.gov/ct2/history/NCT01868997?V_19=View#StudyPageTop.

Clinical Trials No. NCT01868997. Teprotumumab (RV 001) Treatment in Patients With Active Thyroid Eye Disease, Version 2. Reported date submitted: Jun. 9, 2013. Date publicly available: Unknown. Date accessed: May 24, 2024. Available at https://classic.clinicaltrials.gov/ct2/history/NCT01868997?V_2=View#StudyPageTop.

Clinical Trials No. NCT01868997. Teprotumumab (RV 001) Treatment in Patients With Active Thyroid Eye Disease, Version 20. Reported date submitted: Mar. 20, 2017. Date publicly available: Unknown. Date accessed: May 24, 2024. Available at: https://classic.clinicaltrials.gov/ct2/history/NCT01868997?V_20-View#StudyPageTop.

Clinical Trials No. NCT01868997. Teprotumumab (RV 001) Treatment in Patients With Active Thyroid Eye Disease, Version 21. Reported date submitted: Aug. 10, 2017. Date publicly available: Unknown. Date accessed: May 24, 2024. Available at: https://classic.clinicaltrials.gov/ct2/history/NCT01868997?V_21=View#StudyPageTop.

Clinical Trials No. NCT01868997. Teprotumumab (RV 001) Treatment in Patients With Active Thyroid Eye Disease, Version 22. Reported date submitted: Mar. 27, 2018. Date publicly available: Unknown. Date accessed: May 24, 2024. Available at: https://classic.clinicaltrials.gov/ct2/history/NCT01868997?V_22-View#StudyPageTop.

Clinical Trials No. NCT01868997. Teprotumumab (RV 001) Treatment in Patients With Active Thyroid Eye Disease, Version 3. Reported date submitted: Jun. 13, 2013. Date publicly available: Unknown. Date accessed: May 24, 2024. Available at: https://classic.clinicaltrials.gov/ct2/history/NCT01868997?V_3=View#StudyPageTop.

Clinical Trials No. NCT01868997. Teprotumumab (RV 001) Treatment in Patients With Active Thyroid Eye Disease, Version 4. Reported date submitted: Jun. 21, 2013 Date publicly available: Unknown. Date accessed: May 24, 2024. Available at: https://classic.clinicaltrials.gov/ct2/history/NCT01868997?V_4=View#StudyPageTop.

Clinical Trials No. NCT01868997. Teprotumumab (RV 001) Treatment in Patients With Active Thyroid Eye Disease, Version 5. Reported date submitted: Jun. 27, 2013. Date publicly available: Unknown. Date accessed: May 24, 2024. Available at: https://classic.clinicaltrials.gov/ct2/history/NCT01868997?V_5=View#StudyPageTop.

Clinical Trials No. NCT01868997. Teprotumumab (RV 001) Treatment in Patients With Active Thyroid Eye Disease, Version 6. Reported date submitted: Aug. 9, 2013. Date publicly available: Unknown. Date accessed: May 24, 2024. Available at: https://classic.clinicaltrials.gov/ct2/history/NCT01868997?V_6=View#StudyPageTop.

Clinical Trials No. NCT01868997. Teprotumumab (RV 001) Treatment in Patients With Active Thyroid Eye Disease, Version 7. Reported date submitted: Sep. 12, 2013. Date publicly available: Unknown. Date accessed: May 24, 2024. Available at: https://classic.clinicaltrials.gov/ct2/history/NCT01868997?V_7=View#StudyPageTop.

Clinical Trials No. NCT01868997. Teprotumumab (RV 001) Treatment in Patients With Active Thyroid Eye Disease, Version 8. Reported date submitted: Jan. 20, 2014. Date publicly available: Unknown. Date accessed: May 24, 2024. Available at: https://classic.clinicaltrials.gov/ct2/history/NCT01868997?V_8=View#StudyPageTop.

Clinical Trials No. NCT01868997. Teprotumumab (RV 001) Treatment in Patients With Active Thyroid Eye Disease, Version 9. Reported date submitted: Mar. 17, 2014. Date publicly available: Unknown. Date accessed:May 24, 2024. Available at: https://classic.clinicaltrials.gov/ct2/history/NCT01868997?V_9=View#StudyPageTop.

Dolman, P. J. et al., "VISA Classification for Graves orbitopathy", Ophthalmic Plast Reconstr Surg, vol. 22(5), pp. 319-324 (2006).

Dolman, P. J., "Evaluating Graves' orbitopathy", Best Pract Res Clin Endocrinol Metab, vol. 26(3), pp. 229-248 (2012).

Douglas, R. et al., "Aberrant expression of the insulin-like growth factor-1 receptor by T cells from patients with Graves' disease may carry functional consequences for disease pathogenesis", J Immunol., vol. 178(5), pp. 3281-3287 (2007).

Douglas, R. et al., "B cells from patients with Graves' disease aberrantly express the IGF-1 receptor: implications for disease pathogenesis", J Immunol., vol. 181(8), pp. 5768-5774 (2008).

Douglas, R. et al., "Increased generation of fibrocytes in thyroid-associated ophthalmopathy", J Clin Endocrinol Metab., vol. 95(1), pp. 430-438 (2010).

Douglas, R., "Teprotumumab, an Insulin-Like Growth Factor-1 Receptor Antagonist Antibody, in the Treatment of Active Thyroid Eye Disease: A Focus on Proptosis", Eye (Lond), vol. 33(2), pp. 183-190 (2019).

Ezra, D. G. et al., Genome Level Microarray Expression Profiling Implicates IGF-1 and Wnt Signalling Dysregulation in the Pathogenesis of Thyroid Associated Ophthalmopathy, ARVO Annual Meeting Scientific Abstracts, in 2 pages (2011).

(56) References Cited

OTHER PUBLICATIONS

Gianoukakis, A. G. et al., "Immunoglobulin G from patients with Graves' disease induces interleukin-16 and RANTES expression in cultured human thyrocytes: a putative mechanism for T-cell infiltration of the thyroid in autoimmune disease", Endocrinology, vol. 147(4), pp. 1941-1949 (2006).
Görtz, G.-E. et al., "Pathogenic Phenotype of Adipogenesis and Hyaluronan in Orbital Fibroblasts From Female Graves' Orbitopathy Mouse Model", Endocrinology, vol. 157(10), pp. 3771-3778 (2016).
Gupta, S., "Intention-to-treat concept: A review", Perspect Clin Res, vol. 2(3), pp. 109-112 (2011).
Hansson, H., "Aspects of growth factors in exophthalmos", Acta Endocrinologica (Copenh), vol. 121(Suppl. 2), pp. 107-111 (1989).
Hoa, N. et al., "Nuclear Targeting of IGF-1 Receptor in Orbital Fibroblasts from Graves' Disease: Apparent Role of ADAM17", PLoS One, vol. 7(4), pp. e34173 (2012).
Hwang, C. J. et al., "Orbital fibroblasts from patients with thyroid-associated ophthalmopathy overexpress CD40: CD154 hyperinduces IL-6, IL-8, and MCP-1", Invest Ophthalmol Vis Sci., vol. 50(5), pp. 2262-2268 (2009).
Imai, Y. et al., "Effect of growth factors on hyaluronan and proteoglycan synthesis by retroocular tissue fibroblasts of Graves' ophthalmopathy in culture", Acta Endocrinol (Copenh), vol. 126(6), pp. 541-552 (1992).
Kabat, E. A. et al., *Sequences of Proteins of Immunological Interest*, NIH Pub. No. 91-3242. Public Health Service, National Institutes of Health, 5th edition, pp. 647-669 (1991).
Khong, J. J. et al., "Pathogenesis of thyroid eye disease: review and update on molecular mechanisms", Br J Ophthalmol., vol. 100(1), pp. 142-150 (2016).
Khoo, T. K. et al., "Pathogenesis of Graves' Ophthalmopathy: The Role of Autoantibodies", Thyroid, vol. 17(10), pp. 1013-1018 (2007).
Krieger, C. C. et al., "Thyroid Stimulating Hormone (TSH)/Insulin-like Growth Factor 1 (IGF1) Receptor Cross-talk in Human Cells", Curr Opin Endocr Metab Res, vol. 2, pp. 29-33 (2018).
Krieger, C. C. et al., "TSH/IGF-1 Receptor Cross-Talk Rapidly Activates Extracellular Signal-Regulated Kinases in Multiple Cell Types", Endocrinology, vol. 158(10), pp. 3676-3683 (2017).
Krieger, C. C. et al., "TSHR/IGF-1R Cross-Talk, Not IGF-1R Stimulating Antibodies, Mediates Graves' Ophthalmopathy Pathogenesis", Thyroid, vol. 27(5), pp. 746-747 (2017).
Kumar, S. et al., "A stimulatory thyrotropin receptor antibody enhances hyaluronic acid synthesis in graves' orbital fibroblasts: inhibition by an IGF-I receptor blocking antibody", J Clin Endocrinol Metab., vol. 97(5), pp. 1681-1687 (2012).
Kumar, S. et al., "Forkhead Transcription Factor FOXO1 Is Regulated by Both a Stimulatory Thyrotropin Receptor Antibody and Insulin-Like Growth Factor-1 in Orbital Fibroblasts from Patients with Graves' Ophthalmopathy", Thyroid, vol. 25(10), pp. 1145-1150 (2015).
Kurzrock, R. et al., "A Phase I Study of Weekly R1507, A Human Monoclonal Antibody Insulin-like Growth Factor—I Receptor Antagonist, in Patients with Advanced Solid Tumors", Clin Cancer Res, vol. 16(8), pp. 2458-2465 (2010).
Lovell, D. J. et al., "Adalimumab with or without Methotrexate in Juvenile Rheumatoid Arthritis", N Engl J Med, vol. 359, pp. 810-820 (2008).
Ma, H. et al., "The Adverse Events Profile of Anti-IGF-IR Monoclonal Antibodies in Cancer Therapy", Br J Clin Pharmacol, vol. 77(6), pp. 917-928 (2013).
Marcus-Samuels, B. et al., "Evidence that Graves Ophthalmopathy Immunoglobulins Do Not Directly Activate IGF-1 Receptors", Thyroid, vol. 28(5), pp. 650-655 (2018).
Mourits, M. et al., "Clinical activity score as a guide in the management of patients with Graves' ophthalmopathy", Clin Endocrinol (Oxf), vol. 47(1), pp. 9-14 (1997).
Mourits, M. et al., "Clinical criteria for the assessment of disease activity in Graves' ophthalmopathy: a novel approach", Br J Ophthalmol, vol. 73( 8), pp. 639-644 (1989).

Naik, V. M. et al., "Immunopathogenesis of thyroid eye disease: emerging paradigms", Surv Ophthalmol., vol. 55(3), pp. 215-226 (2010).
Pappo, A. et al., "R1507, a Monoclonal Antibody to the Insulin-Like Growth Factor 1 Receptor, in Patients With Recurrent or Refractory Ewing Sarcoma Family of Tumors: Results of a Phase II Sarcoma Alliance for Research Through Collaboration Study", J Clin Oncol, vol. 29(34), pp. 4541-4547, (2011).
Pawlowski, P. et al., "Decreased Frequencies of Peripheral Blood CD4+CD25+CD127-Foxp3+ in Patients with Graves' Disease and Graves' Orbitopathy: Enhancing Effect of Insulin Growth Factor-1 on Treg Cells", Horm Metab Res., vol. 49(3), pp. 185-191 (2017).
Piantanida, E. et al., "Teprotumumab: A New Avenue for the Management of Moderate-to-Severe and Active Graves' Orbitopathy? ", J Endocrinol Invest, vol. 40(8), pp. 885-887 (2017).
Place, R. F. et al., "Inhibiting thyrotropin/insulin-like growth factor 1 receptor crosstalk to treat Graves' ophthalmopathy: studies in orbital fibroblasts in vitro", Br J Pharmacol., vol. 174(4), pp. 328-340 (2017).
Pritchard, J. et al., "Igs from patients with Graves' disease induce the expression of T cell chemoattractants in their fibroblasts", J Immunol., vol. 168(2), pp. 942-950 (2002).
Pritchard, J. et al., "Immunoglobulin activation of T cell chemoattractant expression in fibroblasts from patients with Graves' disease is mediated through the insulin-like growth factor I receptor pathway", J Immunol., vol. 170(12), pp. 6348-6354 (2003).
Ramalingam, S. et al., "Randomized Phase II Study of Erlotinib in Combination with Placebo or R1507, a Monoclonal Antibody to Insulin-Like Growth Factor-1 Receptor, for Advanced-Stage Non-Small-Cell Lung Cancer", J Clin Oncol, vol. 29(34), pp. 4574-4580 (2011).
Salvi, M. et al., "Efficacy of B-cell targeted therapy with rituximab in patients with active moderate to severe Graves' orbitopathy: a randomized controlled study", J Clin Endocrinol Metab., vol. 100(2), pp. 422-431 (2015).
Salvi, M., "Immunotherapy for Graves' ophthalmopathy", Curr Opin Endocrinol Diabetes Obes., vol. 21(5), pp. 409-414 (2014).
Smith, T. et al., "Building the Case for Insulin-Like Growth Factor Receptor—I Involvement in Thyroid-Associated Ophthalmopathy", Front Endocrinol (Lausanne), vol. 7, Article 167, in 8 pages (2017).
Smith, T. et al., "Insulin-Like Growth Factor—I Regulation of Immune Function: A Potential Therapeutic Target in Autoimmune Diseases?", Pharmacological Rev., vol. 62(2), pp. 199-236 (2010).
Smith, T. et al., "Immunoglobulins from patients with Graves' disease induce hyaluronan synthesis in their orbital fibroblasts through the self-antigen, insulin-like growth factor—I receptor", J Clin Endocrinol Metab, vol. 89(10), pp. 5076-5080 (2004).
Smith, T. et al., "New Advances in Understanding Thyroid-Associated Ophthalmopathy and the Potential Role for Insulin-Like Growth Factor—I Receptor [version 1; referees: 2 approved]", F1000 Research 2018, 7(F1000 Faculty Rev):134 last updated Feb. 1, 2018, in 9 pages (2018).
Smith, T. et al., "Pathogenesis of Graves' orbitopathy: A 2010 update", J Endocrinol Invest., vol. 33(6), pp. 414-421 (2010).
Smith, T. et al., "Recognizing the Putative Role for TSH Receptor Expressing Fibrocytes in Thyroid-Associated Ophthalmopathy may solve several mysteries", Nat Rev Endocrinol., vol. 11(3), pp. 171-181 (2015).
Smith, T. et al., "Role of IGF-1 pathway in the pathogenesis of Graves' orbitopathy", Best Pract Res Clin Endocrinol Metab., vol. 26(3), pp. 291-302 (2012).
Smith, T. et al., "Teprotumumab for Thyroid-Associated Ophthalmopathy", N Engl J Med., vol. 376(18), pp. 1748-1761 (2017).
Smith, T. et al., "Unique attributes of orbital fibroblasts and global alterations in IGF-1 receptor signaling could explain thyroid-associated ophthalmopathy", Thyroid, vol. 18(9), pp. 983-988 (2008).
Song, D. et al., "Locally produced insulin-like growth factor-1 by orbital fibroblasts as implicative pathogenic factor rather than systemically circulated IGF-1 for patients with thyroid-associated ophthalmopathy", Graefes Arch Clin Exp Ophthalmol, vol. 250(3), pp. 433-440 (2012).

(56) References Cited

OTHER PUBLICATIONS

Stan, M. N. et al., "Randomized controlled trial of rituximab in patients with Graves' orbitopathy", J Clin Endocrinol Metab., vol. 100(2), pp. 432-441 (2015).
Terwee, C. B. et al., "Development of a disease specific quality of life questionnaire for patients with Graves' ophthalmopathy: the GO-QOL", Br J Ophthalmopathy, vol. 82, pp. 773-779 (1998).
Tsui, S. et al., "Evidence for an association between thyroid-stimulating hormone and insulin-like growth factor 1 receptors: a tale of two antigens implicated in Graves' disease", J Immunol, vol. 181(6), pp. 4397-4405 (2008).
Ugradar, S. et al., "Teprotumumab for non-inflammatory thyroid eye disease (TED): evidence for increased IGF-1R expression", Eye (Lond), vol. 35(9), pp. 2607-2612 (2021).
Ugradar, S. et al., "Teprotumumab for the treatment of chronic thyroid eye disease", Eye (Lond), vol. 36(8), pp. 1553-1559 (2022).
Varewijck, A. J. et al., "Circulating IgGs may modulate IGF-I receptor stimulating activity in a subset of patients with Graves' ophthalmopathy", J Clin Endocrinol Metab., vol. 98(2), pp. 769-776 (2013).
Weightman, D. R. et al., "Autoantibodies to IGF-1 binding sites in thyroid associated ophthalmopathy", Autoimmunity, vol. 16(4), pp. 251-257 (1993).
Werner, S., "Classification of the eye changes of Graves' disease", Am J Ophthalmol, vol. 68(4), pp. 646-648 (1969).
Werner, S., "Modification of the classification of the eye changes of Graves' disease", Am J Ophthalmol, vol. 83(5), pp. 725-727 (1977).
Wiersinga, W. M. et al., "Clinical assessment of patients with Graves' orbitopathy: the European Group on Graves' Orbitopathy recommendations to generalists, specialists and clinical researchers", European Journal of Endocrinology, vol. 155, pp. 387-389 (2006).
Wiersinga, W. M., "Management of Graves opthalmopathy", Nat Clin Pract Endocrinol Metab., vol. 3(5), pp. 396-404 (2007).
Xu, N. et al., "Comparative Efficacy of Medical Treatments for Thyroid Eye Disease: A Network Meta-Analysis", J Ophthalmol., 7184163, in 10 pages (2018).
Zhang, L. et al., "Possible Targets for Nonimmunosuppressive Therapy of Graves' Orbitopathy", J Clin Endocrinol Metab., vol. 99(7), pp. E1183-E1190 (2014).
Zhao, P. et al., "Insulin-like growth factor 1 promotes the proliferation and adipogenesis of orbital adipose-derived stromal cells in thyroid-associated ophthalmopathy", Exp Eye Res, vol. 107, pp. 65-73 (2013).
U.S. Appl. No. 16/256,221; Restriction Response, dated Oct. 16, 2020; 7 pages.
U.S. Appl. No. 16/256,221; Non-Final Office Action, dated Apr. 29, 2021; 28 pages.
U.S. Appl. No. 16/256,221; Notice of Allowance, dated Aug. 23, 2021; 12 pages.
U.S. Appl. No. 16/293,293; Restriction Requirement, dated Dec. 10, 2020; 5 pages.
U.S. Appl. No. 16/293,293; Non-Final Office Action, dated Apr. 29, 2021; 27 pages.
U.S. Appl. No. 16/293,293; Notice of Allowance, dated Aug. 20, 2021; 12 pages.
U.S. Appl. No. 17/117,625, Office Action, dated Sep. 14, 2022; 14 pages.
U.S. Appl. No. 17/531,365; Non-Final Office Action, dated Mar. 19, 2024; 18 pages.
U.S. Appl. No. 17/531,365; Final Office Action, dated Jul. 11, 2024; 15 pages.
U.S. Appl. No. 17/531,365, Notice of Allowance, dated Sep. 13, 2024; 6 pages.
U.S. Appl. No. 17/531,368; Restriction Requirement, dated Mar. 18, 2024; 5 pages.
U.S. Appl. No. 17/531,368; Non-Final Office Action, dated Jul. 11, 2024; 16 pages.
International Application No. PCT/US2019/020770; International Search Report and Written Opinion, date of mailing Jul. 9, 2019; 12 pages.
International Application No. PCT/US2019/020770; International Preliminary Report on Patentability, date of issuance Sep. 17, 2020; 9 pages.
Xu, N. et al., "Ocular Surface Characteristics and Impression Cytology in Patients with Active versus Inactive Thyroid Eye Disease", Eye Science, vol. 27, No. 2, pp. 64-68 (2012).
U.S. Appl. No. 17/531,368; Notice of Allowance, dated Nov. 18, 2024; 7 pages.

```
                        SEQUENCE LISTING

Sequence total quantity: 12
SEQ ID NO: 1            moltype = AA  length = 5
FEATURE                 Location/Qualifiers
source                  1..5
                        mol_type = protein
                        organism = Homo sapiens
SEQUENCE: 1
SYGMH                                                               5

SEQ ID NO: 2            moltype = AA  length = 17
FEATURE                 Location/Qualifiers
source                  1..17
                        mol_type = protein
                        organism = Homo sapiens
SEQUENCE: 2
IIWFDGSSTY YADSVRG                                                 17

SEQ ID NO: 3            moltype = AA  length = 9
FEATURE                 Location/Qualifiers
source                  1..9
                        mol_type = protein
                        organism = Homo sapiens
SEQUENCE: 3
ELGRRYFDL                                                           9

SEQ ID NO: 4            moltype = AA  length = 11
FEATURE                 Location/Qualifiers
source                  1..11
                        mol_type = protein
                        organism = Homo sapiens
SEQUENCE: 4
RASQSVSSYL A                                                       11

SEQ ID NO: 5            moltype = AA  length = 7
FEATURE                 Location/Qualifiers
source                  1..7
                        mol_type = protein
```

```
                    organism = Homo sapiens
SEQUENCE: 5
DASKRAT                                                                7

SEQ ID NO: 6           moltype = AA  length = 10
FEATURE                Location/Qualifiers
source                 1..10
                       mol_type = protein
                       organism = Homo sapiens
SEQUENCE: 6
QQRSKWPPWT                                                            10

SEQ ID NO: 7           moltype = AA  length = 118
FEATURE                Location/Qualifiers
source                 1..118
                       mol_type = protein
                       organism = Homo sapiens
SEQUENCE: 7
QVELVESGGG VVQPGRSQRL SCAASGFTFS SYGMHWVRQA PGKGLEWVAI IWFDGSSTYY     60
ADSVRGRFTI SRDNSKNTLY LQMNSLRAED TAVYFCAREL GRRYFDLWGR GTLVSVSS      118

SEQ ID NO: 8           moltype = AA  length = 108
FEATURE                Location/Qualifiers
source                 1..108
                       mol_type = protein
                       organism = Homo sapiens
SEQUENCE: 8
EIVLTQSPAT LSLSPGERAT LSCRASQSVS SYLAWYQQKP GQAPRLLIYD ASKRATGIPA     60
RFSGSGSGTD FTLTISSLEP EDFAVYYCQQ RSKWPPWTFG QGTKVESK                 108

SEQ ID NO: 9           moltype = AA  length = 18
FEATURE                Location/Qualifiers
source                 1..18
                       mol_type = protein
                       organism = Homo sapiens
SEQUENCE: 9
IIWFDGSSKY YGDSVKGL                                                   18

SEQ ID NO: 10          moltype = AA  length = 7
FEATURE                Location/Qualifiers
source                 1..7
                       mol_type = protein
                       organism = Homo sapiens
SEQUENCE: 10
DASNRAT                                                                7

SEQ ID NO: 11          moltype = AA  length = 118
FEATURE                Location/Qualifiers
source                 1..118
                       mol_type = protein
                       organism = Homo sapiens
SEQUENCE: 11
QVQLVESGGG VVQPGRSLRL SCAASGFTFS SYGMHWVRQA PGKGLEWMAI IWFDGSSKYY     60
GDSVKGRFTI SRDNSKNTLY LQMNSLRADD TAVYYCAREL GRRYFDLWGR GTLVTVSS      118

SEQ ID NO: 12          moltype = AA  length = 324
FEATURE                Location/Qualifiers
source                 1..324
                       mol_type = protein
                       organism = Homo sapiens
SEQUENCE: 12
GLUILEVALL EUTHRGLNSE RPROALATHR LEUSERLEUS ERPROGLYGL UARGALATHR     60
LEUSERCYSA RGALASERGL NSERVALSER SERTYRLEUA LATRPTYRGL NGLNLYSPRO    120
GLYGLNALAP ROARGLEULE UILETYRASP ALASERASNA RGALATHRGL YILEPROALA    180
ARGPHESERG LYSERGLYSE RGLYTHRASP PHETHRLEUT HRILESERSE RLEUGLUPRO    240
GLUASPPHEA LAVALTYRTY RCYSGLNGLN ARGSERLYST RPPROPROTR PTHRPHEGLY    300
GLNGLYTHRL YSVALGLUIL ELYS                                           324
```

METHODS FOR THE TREATMENT OF THYROID EYE DISEASE

PRIORITY APPLICATIONS

This application is a continuation of U.S. application Ser. No. 17/531,365, filed Nov. 19, 2021, which is a continuation of U.S. application Ser. No. 16/256,221, filed Jan. 24, 2019, issued as U.S. Pat. No. 11,208,489 on Dec. 28, 2021, which claims the benefit of priority of U.S. Provisional Applications No. 62/621,201, filed Jan. 24, 2018, No. 62/635,342, files Feb. 26, 2018, and No. 62/716,194, filed Aug. 8, 2018, the contents of which are incorporated by reference as if written herein in their entireties.

REFERENCE TO SEQUENCE LISTING

The present application is filed with a Sequence Listing in Electronic format. The Sequence Listing is provided as a file entitled AMGN025C4_Sequence_Listing.xml, created Oct. 25, 2024, which is 12,061 bytes in size. The information in the electronic format of the sequence listing is incorporated herein by reference in its entirety.

Thyroid-associated ophthalmopathy (TAO), also known as thyroid eye disease (TED), Graves' ophthalmopathy or orbitopathy (GO), thyrotoxic exophthalmos, dysthyroid ophthalmopathy, and several other terms, is orbitopathy associated with thyroid dysfunction. TAO is divided into two types. Active TAO, which typically lasts 1-3 years, is characterized by an ongoing autoimmune/inflammatory response in the soft tissues of the orbit. Active TAO is responsible for the expansion and remodeling of the ocular soft tissues. The autoimmune/inflammatory response of active TAO spontaneously resolves and the condition transitions into inactive TAO. Inactive TAO is the term used to describe the long-term/permanent sequelae of active TAO.

The cause of TAO is unknown. TAO is typically associated with Graves' hyperthyroidism, but can also occur as part of other autoimmune conditions that affect the thyroid gland and produce pathology in orbital and periorbital tissue, and, rarely, the pretibial skin (pretibial myxedema) or digits (thyroid acropachy). TAO is an autoimmune orbitopathy in which the orbital and periocular soft tissues are primarily affected with secondary effects on the eye and vision. In TAO, as a result of inflammation and expansion of orbital soft tissues, primarily eye muscles and adipose, the eyes are forced forward (bulge) out of their sockets—a phenomenon termed proptosis or exophthalmos.

The annual incidence rate of TAO has been estimated at 16 cases per 100,000 women and 2.9 cases per 100,000 men from a study based in one largely rural Minnesota community. There appears to be a female preponderance in which women are affected 2.5-6 times more frequently than men; however, severe cases occur more often in men than in women. In addition, most patients are aged 30-50 years, with severe cases appearing to be more frequent in those older than 50 years. Although most cases of TAO do not result in loss of vision, this condition can cause vision-threatening exposure keratopathy, troublesome diplopia (double vision), and compressive dysthyroid optic neuropathy.

TAO may precede, coincide with, or follow the systemic complications of dysthyroidism. The ocular manifestations of TAO include upper eyelid retraction, lid lag, swelling, redness (erythema), conjunctivitis, and bulging eyes (exophthalmos or proptosis), chemosis, periorbital edema, and altered ocular motility with significant functional, social, and cosmetic consequences.

Many of the signs and symptoms of TAO, including proptosis and ocular congestion, result from expansion of the orbital adipose tissue and periocular muscles. The adipose tissue volume increases owing in part to new fat cell development (adipogenesis) within the orbital fat. The accumulation of hydrophilic glycosaminoglycans, primarily hyaluronic acid, within the orbital adipose tissue and the perimysial connective tissue between the extraocular muscle fibers, further expands the fat compartments and enlarges the extraocular muscle bodies. Hyaluronic acid is produced by fibroblasts residing within the orbital fat and extraocular muscles, and its synthesis in vitro is stimulated by several cytokines and growth factors, including IL-1□, interferon-γ, platelet-derived growth factor, thyroid stimulating hormone (TSH) and insulin-like growth factor I (IGF-I).

TAO is commonly considered to be the autoimmune orbital manifestation of Graves' Disease (GD). However, only approximately 30% of patients with Graves' hyperthyroidism manifest clinically relevant ocular pathology indicating there is mechanistic heterogeneity and differentiation between the conditions. The molecular mechanisms underlying TAO remain unclear. It is accepted that the generation of autoantibodies that act as agonists on the thyroid-stimulating hormone receptor (TSHR) is responsible for Graves' hyperthyroidism. Pathogenic overstimulation of TSHR, leads to overproduction of thyroid hormones (T3 and T4) and accelerated metabolism of many tissues.

In active TAO, autoantibodies trigger connective tissue and fat to expand, in part from stimulating excessive synthesis of hyaluronan. The expanded tissues are infiltrated with T and B cells, become inflamed, and get and extensively remodeled. It has been suggested that TSHR might have some pathogenic role in the development of active TAO. Indeed, a positive correlation has been found between anti-TSHR antibodies and the degree of TAO activity. However, no definitive link has been established, and a proportion of TAO patients remain euthyroid throughout the course of their disease.

Antibodies that activate the insulin-like growth factor I receptor (IGF-IR) have also been detected and implicated in active TAO. Without being bound to any theory, it is believed that TSHR and IGF-IR form a physical and functional complex in orbital fibroblasts, and that blocking IGF-IR appears to attenuate both IGF-I and TSH-dependent signaling. It has been suggested that blocking IGF-IR using an antibody antagonist might reduce both TSHR- and IGF-I-dependent signaling and therefore interrupt the pathological activities of autoantibodies acting as agonists on either receptor.

IGF-IR is a widely expressed heterotetrameric protein involved in the regulation of proliferation and metabolic function of many cell types. It is a tyrosine kinase receptor comprising two subunits. IGF-IRα contains a ligand-binding domain while IGF-IRβ is involved in signaling and contains tyrosine phosphorylation sites. Monoclonal antibodies directed against IGF-IR have been developed and assessed as a therapeutic strategy for several types of solid tumors and lymphomas.

Management of hyperthyroidism due to Graves' disease is imperfect because therapies targeting the specific underlying pathogenic autoimmune mechanisms of the disease are lacking. Even more complex is the treatment of moderate-to-severe active TAO. Although recent years have witnessed a better understanding of its pathogenesis, TAO remains a therapeutic challenge and dilemma. There are no approved drugs to treat active TAO. Intravenous glucocorticoids (ivGCs) and oral glucocorticoids are used to treat patients with moderate-to-severe active TAO, but results are seldom satisfactory. Partial responses are frequent and relapses (rebound) after drug withdrawal are not uncommon. Adverse events do occur and many patients eventually require rehabilitative surgery conducted when their condition has transitioned to inactive TAO.

Recently, attention has been focused on the use of biologicals, which might specifically intervene on the pathogenic mechanisms of TAO. In 2015 two small, monocenter, randomized clinical trials (RCTs) investigated the effects of rituximab, a CD20+ B cell-depleting agent, versus placebo or ivGCs, respectively. The results from the two trials were conflicting; they were negative (no differences with placebo) in the first trial, but positive (beneficial effects comparable to ivGCs) in the second one. The effectiveness of rituximab for moderate-to-severe active TAO therefore remains to be determined. The recent guidelines published by the European Thyroid Association/European Group on Graves' Orbitopathy (EUGOGO) indicate rituximab as a possible second-line treatment for patients poorly responsive to a first course of ivGCs. As with rituximab, there is no dependable evidence concerning other potential therapeutic agents, such as adalimumab, etanercept, infliximab, or monoclonals or small molecules blocking the TSH receptor. The use of the interleukin-6 receptor monoclonal antibody, tocilizumab, based on an ongoing RCT also remains to be determined.

As stated above, medical therapies for moderate-to-severe TAO that have proved to be effective and safe in adequately powered, prospective, placebo-controlled trials are lacking. Previous clinical trials, which were rarely placebo-controlled, suggest that high dose glucocorticoids, alone, or with radiotherapy, can reduce inflammation-related signs and symptoms in patients with active ophthalmopathy, but only minimally affect proptosis and can cause dose-limiting adverse reactions.

Immunoglobulins that activate IGF-IR signaling have been detected in patients with GD and TAO. Furthermore, IGF-I synergistically enhances the actions of thyrotropin. IGF-IR, a membrane-spanning tyrosine kinase receptor with roles in development and metabolism, also stimulates immune function and thus might be targeted therapeutically in autoimmune diseases. IGF-IR is overexpressed by orbital fibroblasts and by T cells and B cells in persons with GD and TAO. It forms a signaling complex with TSHR through which it is transactivated. In vitro studies of orbital fibroblasts and fibrocytes show that IGF-IR-inhibitory antibodies can attenuate the actions of IGF-I, thyrotropin, thyroid-stimulating immunoglobulins, and immunoglobulins isolated from patients with GD and TAO. These observations prompted a trial of teprotumumab, a fully human IGF-IR-inhibitory monoclonal antibody, in patients with active, moderate-to-severe TAO.

Provided herein are antibodies against insulin-like growth factor I receptor (IGF-IR) for use in the treatment of GO or TAO.

Also provided herein is a method of reducing proptosis (e.g., by at least 2 mm) and reducing the clinical activity score (CAS) in a subject with thyroid-associated ophthalmopathy (TAO), thyroid eye disease (TED) or Graves' ophthalmopathy (GO) comprising administering to the subject an effective amount of an antibody, or an antigen binding fragment thereof, wherein the antibody specifically binds to and inhibits insulin-like growth factor-I receptor (IGF-IR).

Also provided herein is a method of reducing the severity of, or treating, TED comprising administering to a subject in need thereof, an effective amount of an antibody, or an antigen binding fragment thereof, wherein the antibody specifically binds to and inhibits IGF-IR, and wherein the antibody (i) reduces proptosis by at least 2 mm; and (ii) reduces the CAS in the subject by at least 2 points (on the 7-point version of the scale—as described below).

Also provided herein is a method of reducing proptosis by at least 4 mm in a subject with TED comprising administering to the subject an effective amount of an antibody, or an antigen binding fragment thereof, wherein the antibody specifically binds to and inhibits IGF-IR.

Also provided herein is a method of reducing the severity of, or treating, TED comprising administering to a subject in need thereof, an effective amount of an antibody, or an antigen binding fragment thereof, wherein the antibody specifically binds to and inhibits IGF-IR, and wherein the antibody reduces proptosis by at least 4 mm.

Also provided herein is a method of reducing the severity of, or treating, diplopia in a subject with TED, comprising administering to the subject, an effective amount of an antibody, or an antigen binding fragment thereof, wherein the antibody specifically binds to and inhibits IGF-IR.

In some embodiments, the antibody, or an antigen binding fragment thereof, that is administered to the subject comprises: (i) heavy chain complementarity determining region (CDR) 1, 2 and 3, i.e., CDR1, CDR2, and CDR3 amino acid sequences and light chain CDR1, CDR2, and CDR3 amino acid sequences as set forth in SEQ ID NOs: 1-6, respectively; or (ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively.

In some embodiments, the antibody, or an antigen binding fragment thereof, that is administered to the subject comprises: (i) a heavy chain variable region comprising the amino acid sequence of SEQ ID NO: 7 and a light chain variable region comprising the amino acid sequence of SEQ ID NO: 8; or (ii) a heavy chain variable region comprising the amino acid sequence of SEQ ID NO: 11 and a light chain variable region comprising the amino acid sequence of SEQ ID NO: 12.

In some embodiments, the antibody that is administered to the subject is antibody 1 or antibody 2, as disclosed herein, or an antigen binding fragment thereof. In some embodiment of the invention, antibody 1 is teprotumumab.

Also provided herein is a method of reducing the severity of TAO (TED or GO) comprising administering to a subject in need thereof, an effective amount of a pharmaceutical composition comprising an antibody that specifically binds to and inhibits IGF-IR, or an antigen binding fragment thereof, and a pharmaceutically acceptable excipient or diluent or carrier. In some embodiments, the antibody, or an antigen binding fragment thereof, comprises the complementarity determining regions or heavy and/or light chain variable regions as disclosed herein.

DESCRIPTION OF FIGURES

FIG. 2 compares the onset of response amongst responders in teprotumumab and placebo groups.

FIG. 3 compares the proportion of patients who had a response between the teprotumumab and placebo groups at weeks 6, 12, 18, and 24.

FIG. 4 compares the level of response between the teprotumumab group than in the placebo group In FIGS. 5, 6, 8, and 9, means±SE are shown, and P values were calculated with the use of a mixed model of repeated-measurements analysis involving the intention-to-treat population (45 patients in the placebo group and 42 patients in the teprotumumab group). P values shown in FIGS. 7 and 10 were calculated with the use of the chi-square test comparing data from patients who had a response with data from those who did not.

FIG. 5 shows the change in proptosis from baseline.

FIG. 6 shows the change in the Clinical Activity Score from baseline.

FIG. 7 shows the results of the post hoc analysis of the percentage of patients with a Clinical Activity Score of 0 or 1 through week 24.

FIG. 8 shows the change in the visual-functioning subscale of the Graves' ophthalmopathy-specific quality-of-life scale (GO-QOL) from baseline. Scores on the visual-functioning subscale range from 0 to 100, and a change of 8 points is considered to be clinically relevant.

FIG. 9 shows the change in the GO-QOL appearance subscale from baseline. Scores on the appearance subscale range from 0 to 100, and a change of 8 points is considered to be clinically relevant.

FIG. 10 shows the response with respect to subjective diplopia. In this assessment, patients are categorized according to four grades, and a change of one grade or more is considered to be clinically relevant.

Figure 1:
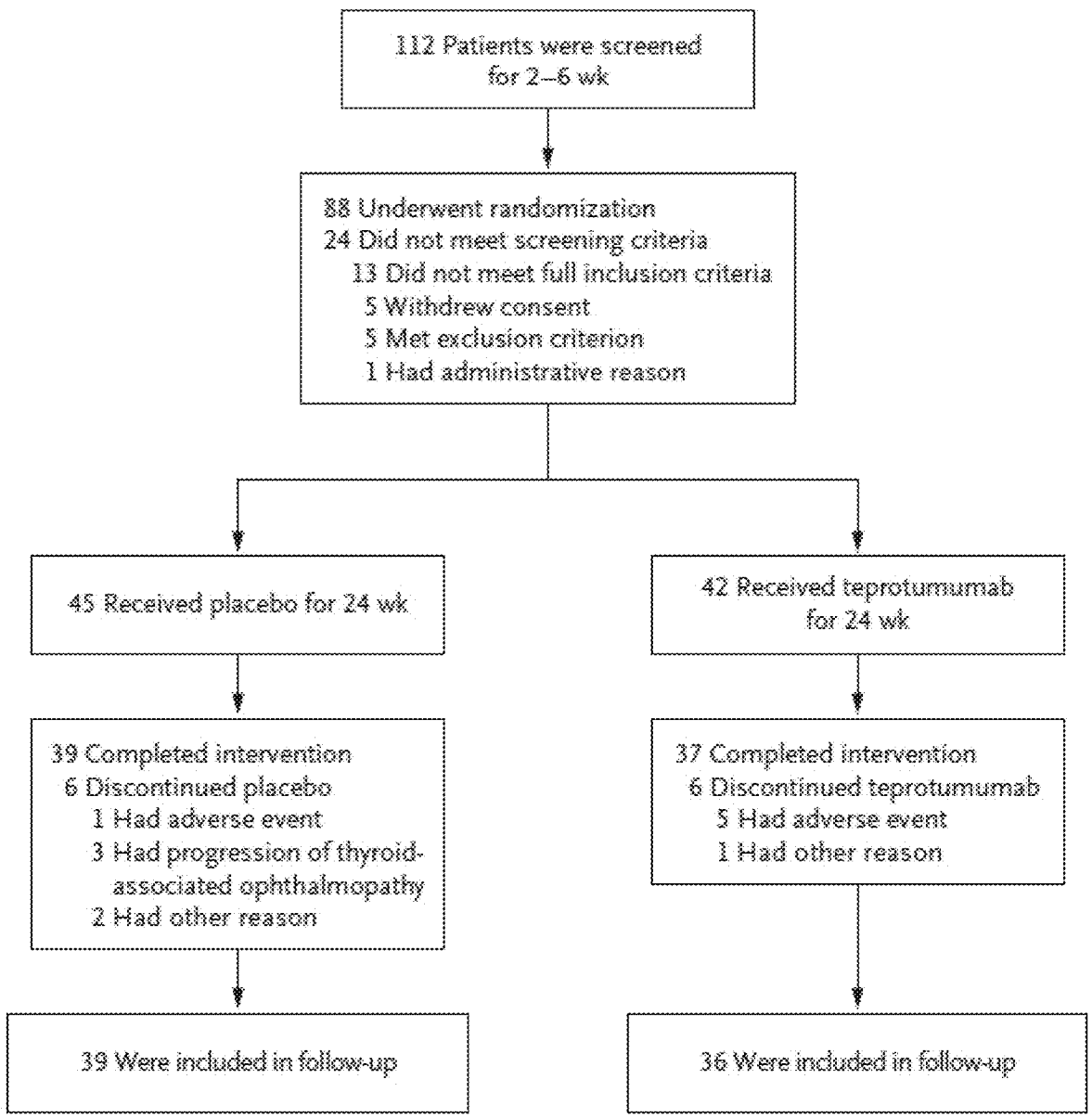
FIG. 1 shows the screening, randomization to teprotumumab therapy or placebo, completion, and follow-up of patients from the trial of patients from the trial.

The Figures are discussed further below.

DETAILED DESCRIPTION

Certain antibodies are able to decrease TSHR and IGF-IR display by orbital fibroblasts and fibrocytes and attenuate the actions of IGF-I, TSH, thyroid-stimulating immunoglobulins, and immunoglobulins isolated from patients with GD and/or TAO.

As described above, TED (TAO or GO) remains inadequately treated. Current medical therapies, which primarily consist of glucocorticoids, have limited efficacy and present safety concerns. It is well known that broad immunosuppressive treatments for TAO, e.g. glucocorticoids and rituximab, cause a limited reduction in exophthalmos. In the largest RCT using three different cumulative doses of ivGCs (2.25 g, 4.98 g. 7.47 g of methylprednisolone), the mean reduction in proptosis was 0.6 mm, even using the highest dose. Results were not different using rituximab. Further, advanced cases of TAO or TED usually call for more invasive surgical treatment such as orbital decompression. Provided herein, is an extremely effective, significantly less invasive method of treating TED (TAO or GO) that also has an improved side effects profile.

Until the present disclosure, therapies for the treatment of TED (TAO or GO) had, as stated above, not only limited efficacy, but also safety concerns. As stated by one of skill in the art, "[t]he most striking and unexpected effect of [the methods disclosed herein] is the treatment-related decrease in exophthalmos [i.e., proptosis]. It is well known that immunosuppressive treatments for GO cause a limited reduction in exophthalmos, [but with the methods disclosed herein] exophthalmos decreased by an average of 2.46 mm (vs. 0.15 mm in the placebo group), . . . These results, never achieved with whatsoever medical treatment, are comparable to those obtained with orbital decompression" (Piantanida, E. and Bartalena, L. *J Endocrinol Invest*, 2017, 40, 885-887).

Accordingly, provided herein is a method of reducing proptosis by at least 2 mm and reducing the clinical activity score (CAS) in a subject with TED (TAO or GO). The method comprises administering to the subject an effective amount of an antibody, or an antigen binding fragment thereof, wherein the antibody specifically binds to and inhibits IGF-IR (e.g., teprotumumab).

Also provided herein is a method of reducing the severity of, or treating, TED (TAO or GO). The method comprises administering to a subject in need thereof, an effective amount of an antibody, or an antigen binding fragment thereof, wherein the antibody specifically binds to and inhibits IGF-IR (e.g., teprotumumab), and wherein the antibody (i) reduces proptosis by at least 2 mm; and (ii) reduces the CAS in the subject by at least 2 points (on the 7-point version of the scale).

In some embodiments, the reduction in proptosis or exophthalmos could be greater than 2 mm, for example, 2.2 mm, 2.4 mm, 2.5 mm, 2.6 mm. 2.8 mm, 3 mm, 3.2 mm, 3.4 mm, 3.5 mm, 3.6 mm, 3.8 mm, 4 mm, 4.1 mm, 4.2 mm, 4.3 mm, 4.4 mm, 4.5 mm, 4.6 mm, 4.7 mm, 4.8 mm, 4.9 mm, 5 mm or more than 5 mm.

In some embodiments, the reduction in CAS is by 2 points or more, for example, by 3, 4, 5, 6, or 7 points. In one embodiment, the reduction in CAS is by 2 or more points. In another embodiment, it is by 3 or more points. In yet another embodiment, the reduction in CAS is by 4 or more points.

Also provided herein is a method of reducing proptosis by at least 4 mm in a subject with TED (TAO or GO). The method comprises administering to the subject an effective amount of an antibody, or an antigen binding fragment thereof, wherein the antibody specifically binds to and inhibits IGF-IR (e.g., teprotumumab).

Also provided herein is a method of reducing the severity of, or treating, TED. The method comprises administering to a subject in need thereof an effective amount of an antibody, or an antigen binding fragment thereof, wherein the antibody specifically binds to and inhibits IGF-IR (e.g., teprotumumab), and wherein the antibody reduces proptosis or exophthalmos by at least 3 mm. Also provided herein is a method of reducing the severity of, or treating, TED. The method comprises administering to a subject in need thereof, an effective amount of an antibody, or an antigen binding fragment thereof, wherein the antibody specifically binds to and inhibits IGF-IR (e.g., teprotumumab), and wherein the antibody reduces proptosis or exophthalmos by at least 4 mm.

Also provided herein is a method of reducing the severity of, or treating, diplopia associated with TED (in a subject with TED and diplopia), comprising administering to the subject, an effective amount of an antibody, or an antigen binding fragment thereof, wherein the antibody specifically binds to and inhibits IGF-IR (e.g., teprotumumab).

Also provided herein is a method of reducing the severity of, or treating, diplopia in a subject with thyroid eye disease (TED), comprising administering to the subject an effective amount of an antibody, or an antigen binding fragment thereof, wherein the antibody specifically binds to and inhibits IGF-IR (e.g., teprotumumab).

When TED is severe, this active autoimmune disease, characterized by orbital tissue remodeling from activation of TSH and IGF-1 receptors, results in excess extracellular matrix and proptosis/diplopia, a major quality of life (QoL)

issue for TED patients. The severity and long-term diplopia response from a masked, placebo-controlled trial of teprotumumab in TED are presented herein, and the results showed that diplopia improved relative to placebo and was sustained out to 51 weeks after drug discontinuation.

Accordingly, also provided herein is a method of reducing the severity of, or treating, constant diplopia (CD) in a subject with thyroid eye disease (TED), comprising administering to the subject, an effective amount of an antibody, or an antigen binding fragment thereof, wherein the antibody specifically binds to and inhibits IGF-IR (e.g., teprotumumab). In some embodiments, the with teprotumumab to improve the CD QoL in patients with severe TED. Also provided herein is a method of treatment of diplopia comprising administering to the subject, an effective amount of an antibody, or an antigen binding fragment thereof, wherein the antibody specifically binds to and inhibits IGF-IR (e.g., teprotumumab), that results in improved diplopia relative to placebo which is sustained out to 51 weeks after drug discontinuation.

It should be noted that not all subjects respond to administration of the antibody, or an antigen binding fragment thereof, in the same manner. When administered to a population of patients, about 20%, 25%, 30%, 35%, 40%, 45%, 50%, 55%, 60%, 65%, 70%, 75%, 80%, 85%, 90%, 95% or 100% of the patients may respond with a reduction in proptosis or exophthalmos by at least 2 mm and a reduction in the CAS by at least 2 points. In some embodiments, the response is seen in at least 20%, or at least 25%, or at least 30%, or at least 35%, or at least 40%, or at least 45%, or at least 50%, or at least 55%, or at least 60%, or at least 65%, or at least 70%, or at least 80% of the patients.

In some embodiments, the antibody, or an antigen binding fragment thereof, reduces proptosis by at least 3 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 3.5 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 4 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 4 mm in about 40% of the subjects.

The antibody, or an antigen binding fragment thereof, can be administered in a single dose or in multiple doses. In one embodiment, the therapeutic antibody is administered to the subject in a single dose. In another embodiment, the therapeutic antibody is administered to the subject in multiple doses, spread out over the course of a few days, weeks or months. In some embodiments the antibody, or an antigen binding fragment thereof, is administered every week or every 2 weeks or every 3 weeks or every 4 weeks or every 5 weeks or every 6 weeks or every 7 weeks or every 8 weeks or every month or every 2 months or every 3 months.

In some embodiments the antibody, or an antigen binding fragment thereof, is administered in multiple doses and the dosage is the same each time. In some embodiments the antibody, or an antigen binding fragment thereof, is administered in multiple doses and the dosage at the time of first administration is different (could be higher or lower) from those at subsequent times. In some embodiments the antibody, or an antigen binding fragment thereof, is administered in multiple doses and the dosage is adjusted at each administration based on the subject's response to the therapy.

The dosage may further vary between patients, based on different factors such as the age, gender, race, and body weight of each patient. In one embodiment, the dosage varies by body weight of the patient. The dosage could range from about 1 mg of the antibody, or an antigen binding fragment thereof, per kilogram of body weight to about 100 mg of the antibody, or an antigen binding fragment thereof, per kilogram of body weight. The dosage, could for example, be 1 mg, 2 mg, 3 mg, 5 mg, 7 mg, 10 mg, 12 mg, 15 mg, 17 mg, 20 mg, 22 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg, of the antibody, or an antigen binding fragment thereof, per kilogram of body weight.

In some embodiments, the dosage is about 1 mg/kg to about 5 mg/kg of the antibody, or an antigen binding fragment thereof. In some embodiments, the dosage is about 5 mg/kg to about 10 mg/kg of the antibody, or an antigen binding fragment thereof. In some embodiments, the dosage is about 10 mg/kg to about 15 mg/kg of the antibody, or an antigen binding fragment thereof. In some embodiments, the dosage is about 15 mg/kg to about 20 mg/kg of the antibody, or an antigen binding fragment thereof.

In some embodiments where the antibody, or an antigen binding fragment thereof, is administered in multiple doses and the dosage at the time of first administration is different from those at subsequent times, the dosage at the time of first administration is about 1 mg/kg to about 5 mg/kg of the antibody, or an antigen binding fragment thereof; or about 5 mg/kg to about 10 mg/kg of the antibody, or an antigen binding fragment thereof; or about 10 mg/kg to about 15 mg/kg of the antibody, or an antigen binding fragment thereof; or about 15 mg/kg to about 20 mg/kg of the antibody, or an antigen binding fragment thereof; or about 20 mg/kg to about 25 mg/kg of the antibody, or an antigen binding fragment thereof. The subsequent dose(s) could be higher or lower than the first dose. In some embodiments, the subsequent dose is about 1 mg/kg to about 5 mg/kg of the antibody, or an antigen binding fragment thereof; or about 5 mg/kg to about 10 mg/kg of the antibody, or an antigen binding fragment thereof; or about 10 mg/kg to about 15 mg/kg of the antibody, or an antigen binding fragment thereof; or about 15 mg/kg to about 20 mg/kg of the antibody, or an antigen binding fragment thereof; or about 20 mg/kg to about 25 mg/kg of the antibody, or an antigen binding fragment thereof.

The duration of the treatment would depend on the subject's response to the therapy and can range from about one month or 4 weeks to about 2 years or 100 weeks. In different embodiments, the treatment may be provided over a total duration of about 1 month, 2 months, 3 months, 4 months, 5 months, 6 months, 7 months, 8 months, 9 months, 10 months, 11 months, 1 year, 14 months, 16 months, 18 months, 20 months, 22 months or 2 years. In other embodiments, the treatment may be provided over a total duration of 4, 6, 8, 10, 12, 14, 16, 20, 22, 24, 26, 28, 30, 32, 34, 36, 38, 40, 42, 44, 46, 48, 50, 52 weeks, or extended to 56, 64, 72, 80, 88, 96 or 104 weeks.

In one embodiment, the antibody, or an antigen binding fragment thereof, is administered for a duration of 24 weeks at intervals of 3 weeks starting with an initial dose of 10 mg per kilogram of body weight, followed by 20 mg per kilogram for seven additional infusions.

The antibody, or an antigen binding fragment thereof, may be administered by any suitable route including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions disclosed herein. Typically, the therapeutic antibody may be prepared as a freeze-dried (lyophilized) powder or as an injectable, either as a liquid solution or suspension. Solid forms suitable for solution in, or suspension in, liquid vehicles prior to injection may also be used.

Provided herein are the following specific embodiments.

Provided as Embodiment 1 is a method of a) reducing proptosis by at least 2 mm and b) reducing the clinical activity score (CAS) in a subject with thyroid eye disease (TED), comprising administering to the subject an effective amount of an antibody, or an antigen binding fragment thereof, wherein the antibody specifically binds to and inhibits insulin like growth factor-I receptor (IGF-IR).

Embodiment 2: The method of Embodiment 1, wherein CAS is reduced by at least 2 points.

Embodiment 3: The method of Embodiment 1, wherein proptosis is reduced by at least 3 mm and CAS is reduced by at least 3 points.

Embodiment 4: The method of Embodiment 3, wherein proptosis is reduced by at least 4 mm in at least 40% of the subjects.

Provided as Embodiment 5 is a method of reducing proptosis by at least 4 mm in a subject with TED, comprising administering to the subject an effective amount of an antibody, or an antigen binding fragment thereof, wherein the antibody specifically binds to and inhibits IGF-IR.

Provided as Embodiment 6 is a method of treating or reducing the severity of diplopia in a subject with thyroid eye disease (TED), comprising administering to the subject an effective amount of an antibody, or an antigen binding fragment thereof, wherein the antibody specifically binds to and inhibits IGF-IR.

Embodiment 7: The method of Embodiment 6, wherein the diplopia is constant diplopia.

Embodiment 8: The method of Embodiment 6, wherein the diplopia is inconstant diplopia.

Embodiment 9: The method of Embodiment 6, wherein the diplopia is intermittent diplopia.

Embodiment 10: The method of any of Embodiments 6-9 wherein the improvement in or reduction in severity of diplopia is sustained at least 20 weeks after discontinuation of antibody administration.

Embodiment 11: The method of any of Embodiments 6-9 wherein the improvement in or reduction in severity of diplopia is sustained at least 40 weeks after discontinuation of antibody administration.

Embodiment 12: The method of any of Embodiments 6-9 wherein the improvement in or reduction in severity of diplopia is sustained at least 20 weeks after discontinuation of antibody administration.

Provided as Embodiment 13 is a method of reducing the Clinical Activity Score (CAS) in a subject with thyroid eye disease (TED) to 0 or 1, comprising administering to the subject an effective amount of an antibody, or an antigen binding fragment thereof, wherein the antibody specifically binds to and inhibits IGF-IR.

Embodiment 14: The method of Embodiment 13, comprising administering to the subject the effective amount of the antibody, or antigen binding fragment thereof, for a period of at least 12 weeks.

Embodiment 15: The method of Embodiment 13, comprising administering to the subject the effective amount of the antibody, or antigen binding fragment thereof, for a period of at least 18 weeks.

Embodiment 16: The method of Embodiment 13, comprising administering to the subject the effective amount of the antibody, or antigen binding fragment thereof, for a period of at least 24 weeks.

Provided as Embodiment 17 is a method of improving the visual functioning of a subject with thyroid eye disease (TED) to 0 or 1, comprising administering to the subject an effective amount of an antibody, or an antigen binding fragment thereof, wherein the antibody specifically binds to and inhibits IGF-IR.

Embodiment 18: The method of Embodiment 17, wherein the visual functioning is measured by the Graves' Ophthalmopathy Quality of Life (GO-QoL) visual functioning subscale.

Provided as Embodiment 19 is a method of improving the visual appearance of a subject with thyroid eye disease (TED) to 0 or 1, comprising administering to the subject an effective amount of an antibody, or an antigen binding fragment thereof, wherein the antibody specifically binds to and inhibits IGF-IR.

Embodiment 20: The method of Embodiment 19, herein the visual functioning is measured by the Graves' Ophthalmopathy Quality of Life (GO-QoL) visual appearance subscale.

Provided as Embodiment 21 is a method of treating or reducing the severity of diplopia in a subject with thyroid eye disease (TED), comprising administering to the subject an effective amount of an antibody, or an antigen binding fragment thereof, wherein the antibody specifically binds to and inhibits IGF-IR.

Embodiment 22: The method of Embodiment 21, wherein the diplopia is constant diplopia.

Embodiment 23: The method of Embodiment 22, wherein the improvement in or reduction in severity of diplopia is sustained at least 20 weeks after discontinuation of antibody administration.

Embodiment 24: The method of Embodiment 22, wherein the improvement in or reduction in severity of diplopia is sustained at least 40 weeks after discontinuation of antibody administration.

Embodiment 25: The method of Embodiment 22, wherein the improvement in or reduction in severity of diplopia is sustained at least 50 weeks after discontinuation of antibody administration.

Embodiment 26: The method of Embodiment 21, wherein the diplopia is inconstant diplopia.

Embodiment 27: The method of Embodiment 21, wherein the diplopia is intermittent diplopia.

Embodiment 28: The method of any one of Embodiments 1-27, wherein the antibody is administered at a dosage of about 1 mg/kg to about 5 mg/kg antibody as a first dose.

Embodiment 29: The method of any one of Embodiments 1-27, wherein the antibody is administered at a dosage of about 5 mg/kg to about 10 mg/kg antibody as a first dose.

Embodiment 30: The method of either of Embodiments 28 and 29, wherein the antibody is administered at a dosage of about 5 mg/kg to about 20 mg/kg antibody in subsequent doses.

Embodiment 31: The method of any one of Embodiments 1-30, wherein the antibody is administered in the following amounts:
about 10 mg/kg antibody as a first dose; and
about 20 mg/kg antibody in subsequent doses.

Provided as Embodiment 32 is a method of treatment of thyroid eye disease (TED), comprising administering to a subject in need thereof an antibody, or an antigen binding fragment thereof, wherein the antibody specifically binds to and inhibits IGF-IR, wherein the antibody is administered in the following amounts:
about 10 mg/kg antibody as a first dose; and
about 20 mg/kg antibody in subsequent doses.

Embodiment 33: The method of any of Embodiments 30, 31, and 32, wherein the subsequent doses are administered every three weeks for at least 21 weeks.

Embodiment 34: The method of any one of Embodiments 1-33, wherein the antibody, or an antigen binding fragment thereof, has a binding affinity ($K_D$) of $10^{-8}$ M or less for the IGF-1R.

Embodiment 35: The method of any one of Embodiments 1-33, wherein the antibody, or an antigen binding fragment thereof, has a binding affinity ($K_D$) of $10^{-13}$ to $10^{-9}$ M for the IGF-1R.

Embodiment 36: The method of any one of Embodiments 1-33, wherein the antibody, or an antigen binding fragment thereof, has an $IC_{50}$ values for the binding of IGF-I and IGF-II to IGF-IR of no more than about 2 nM.

Embodiment 37: The method of any one of Embodiments 1-36, wherein the antibody, or an antigen binding fragment thereof, comprises a heavy chain comprising CDR1, CDR2 and CDR3 and a light chain comprising CDR1, CDR2 and CDR3,
wherein the heavy chain CDR1, CDR2, and CDR3 amino acid sequences and light chain CDR1, CDR2, and CDR3 amino acid sequences are at least 90% identical to
(i) the amino acid sequences of SEQ ID NOs: 1-6, respectively; or
(ii) the amino acid sequences of SEQ ID NOs: 1, 9, 3, 4, 10, 6, respectively.

Embodiment 38: The method of any one of Embodiments 1-36, wherein the antibody, or an antigen binding fragment thereof, comprises:
(i) heavy chain CDR1, CDR2, and CDR3 amino acid sequences and light chain CDR1, CDR2, and CDR3 amino acid sequences as set forth in SEQ ID NOs: 1-6, respectively; or
(ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively.

Embodiment 39: The method of either of Embodiments 37 or 38, wherein the antibody, or an antigen binding fragment thereof, comprises:
(i) a heavy chain variable region having at least 80% sequence identity to the amino acid sequence of SEQ ID NO: 7 and a light chain variable region having at least 80% sequence identity to the amino acid sequence of SEQ ID NO: 8; or
(ii) a heavy chain variable region having at least 80% sequence identity to the amino acid sequence of SEQ ID NO: 11 and a light chain variable region having at least 80% sequence identity to the amino acid sequence of SEQ ID NO: 12.

Embodiment 40: The method of Embodiment 39, wherein the antibody, or an antigen binding fragment thereof, comprises:
(i) a heavy chain variable region comprising the amino acid sequence of SEQ ID NO: 7 and a light chain variable region comprising the amino acid sequence of SEQ ID NO: 8; or
(ii) a heavy chain variable region comprising the amino acid sequence of SEQ ID NO: 11 and a light chain variable region comprising the amino acid sequence of SEQ ID NO: 12.

Embodiment 41: The method of any one of Embodiments 1-40, wherein the antibody is antibody 1 or antibody 2, or an antigen binding fragment thereof.

Embodiment 42: The method of any one of Embodiments 1-41, wherein the antibody is teprotumumab.

Embodiment 43: The method of any one of Embodiments 1-42, wherein the antibody, or an antigen binding fragment thereof, is a human antibody, a monoclonal antibody, a human monoclonal antibody, a purified antibody, a diabody, a single-chain antibody, a multi-specific antibody, Fab, Fab', F(ab')2, Fv or scFv.

Embodiment 44: The method of any one of Embodiments 1-43, wherein the antibody, or an antigen binding fragment thereof, is administered in a pharmaceutical composition that additionally comprises a pharmaceutically acceptable diluent or excipient or carrier.

Embodiment 45: The method of Embodiment 44, wherein the pharmaceutical composition further comprises one or more pharmaceutically active compounds for the treatment of TED.

Embodiment 46: The method of Embodiment 45, wherein the pharmaceutical composition further comprises corticosteroids; rituximab or other anti-CD20 antibodies; tocilizumab or other anti-IL-6 antibodies; or selenium, infliximab or other anti-TNF□□ antibodies or a thyroid-stimulating hormone receptor (TSHR) inhibitor.

Embodiment 47: The method of any one of Embodiments 1-46, wherein the treatment is efficacious for at least 4 weeks beyond the last administered dose.

Embodiment 48: The method of any one of Embodiments 1-46, wherein the treatment is efficacious for at least 6 weeks beyond the last administered dose.

Embodiment 49: The method of any one of Embodiments 1-46, wherein the treatment is efficacious for at least 8 weeks beyond the last administered dose.

Embodiment 50: The method of any one of Embodiments 1-36, wherein the treatment is efficacious for at least 20 weeks beyond the last administered dose.

Also provided are embodiments wherein any embodiment above may be combined with any one or more of these embodiments, provided the combination is not mutually exclusive. As used herein, two embodiments are "mutually exclusive" when one is defined to be something which is different than the other.

The following terms shall be understood to have the meanings ascribed herein.

As used herein, "Thyroid-associated Ophthalmopathy" (TAO), "Thyroid Eye Disease" (TED), "Thyroid Inflammatory Eye Disease (TIED)," "Graves' Ophthalmopathy" (GO) or "Graves' Orbitopathy" (GO) refer to the same disorder or condition and are used interchangeably. They all refer to the inflammatory orbital pathology associated with some autoimmune thyroid disorders, most commonly with "Graves' Disease" (GD), but sometimes with other diseases, e.g. Hashimoto's thyroiditis.

The terms "proptosis" and "exophthalmos" (also known as exophthalmus, exophthalmia, or exorbitism) refer to the forward projection, displacement, bulging, or protrusion of an organ. As used herein, the terms refer to the forward projection, displacement, bulging, or protrusion of the eye anteriorly out of the orbit. Proptosis and exophthalmos are considered by some of skill in the art to have the same meaning and are often used interchangeably, while others attribute subtle differences to their meanings. Exophthalmos is used by some to refer to severe proptosis; or to refer to endocrine-related proptosis. Yet others use the term exophthalmos when describing proptosis associated with the eye, in, for example, subjects with TAO (TED or GO).

As used herein, the terms "proptosis" and "exophthalmos" are used interchangeably and refer to the forward projection, displacement, bulging, or protrusion of the eye anteriorly out of the orbit. Owing to the rigid bony structure of the orbit with only anterior opening for expansion, any increase in orbital soft tissue contents taking place from the side or from behind will displace the eyeball forward. Proptosis or exophthalmos can be the result of a several disease processes including infections, inflammations, tumors, trauma, metastases, endocrine lesions, vascular diseases & extra orbital lesions. TAO (TED or GO) is currently recognized as the most common cause of proptosis in adults. Exophthalmos can be either bilateral, as is often seen in TAO (TED or GO), or unilateral (as is often seen in an orbital tumor).

Measurement of the degree of exophthalmos can be performed using an exophthalmometer, an instrument used for measuring the degree of forward displacement of the eye. The device allows measurement of the forward distance of the lateral orbital rim to the front of the cornea.

Computed tomography (CT) scanning and Magnetic resonance imaging (MRI) may also be used in evaluating the degree of exophthalmos or proptosis. CT scanning is an excellent imaging modality for the diagnosis of TAO. In addition to allowing visualization of the enlarged extraocular muscles, CT scans provide the surgeon or clinician with depictions of the bony anatomy of the orbit when an orbital decompression is required. MRI, with its multi-planar and inherent contrast capabilities, provides excellent imaging of the orbital contents without the radiation exposure associated with CT scan studies. MRI provides better imaging of the optic nerve, orbital fat, and extraocular muscle, but CT scans provide better views of the bony architecture of the orbit.

Orbital ultrasonography can also be a used for the diagnosis and evaluation of TAO, because it can be performed quickly and with a high degree of confidence. High reflectivity and enlargement of the extraocular muscles are assessed easily, and serial ultrasonographic examinations can also be used to assess progression or stability of the ophthalmopathy.

Based on the technologies currently available, or that will become available in the future, one of skill in the art would be capable of determining the best modality for diagnosing and evaluating the extent of proptosis or exophthalmos.

Although it is generally accepted that the normal range of proptosis is 12-21 mm, it must be noted that the value for a normal person varies by age, gender and race. For example, in normal adult white males, the average distance of globe protrusion is 16.5 mm, with the upper limit of normal at 21.7 mm. In adult African Americans it averages 18.2 mm, with an upper normal limit of 24.1 mm in males and 22.7 mm in females. In Mexican adults, males averaged 15.2 mm and females averaged 14.8 mm and in Iran, for the age group of 20-70 years, the average was 14.7 mm. In Taiwanese adults, comparing normal subjects to those with Graves' Ophthalmopathy, the normal group had an average reading of 13.9 mm versus 18.3 mm for the TAO group.

Even within a group of people, there can be variability. Four ethnic groups in Southern Thailand had exophthalmometry measurement averages ranging from 15.4 mm to 16.6 mm. In 2477 Turkish patients, the median measurement was 13 mm, with an upper limit of 17 mm; and in a Dutch study, the upper limit was 20 mm in males and 16 mm in females.

Although the average and upper limits for exophthalmos or proptosis vary widely, it is accepted in the field that a difference greater than 2 mm between the eyes is significant and not normal.

One of skill in the art, for example an ophthalmologist, surgeon or other clinician skilled in the knowledge and treatment of eye disorders would know what a normal value of proptosis is based on the age, gender and race of the subject and have the ability to diagnose or evaluate the presence or absence of proptosis as well as track its progression.

Activity Measures or Assessments

Several classification systems have been conceived to assess the clinical manifestations of TAO. In 1969, Werner reported the NOSPECS Classification (No physical signs or symptoms, Only signs, Soft tissue involvement, Proptosis, Extraocular muscle signs, Corneal involvement, and Sight loss) (Werner, S. C. *American Journal of Ophthalmology*, 1969, 68, no. 4, 646-648.)

The modified NOSPECS was also published by Werner in 1977 and has been broadly used since then (Werner, S. C. *American Journal of Ophthalmology*, 1977, 83, no. 5, 725-727). This classification grades for clinical severity and does not provide a means of distinguishing active TAO (inflammatory progressive) from inactive TAO (noninflammatory stationary). Therefore, the indication for treatments used to be based exclusively in the severity of symptoms without consideration whether the disease was active or inactive. In 1989, Mourits et al. described the Clinical Activity Score (CAS) (Mourits et al., *British Journal of Ophthalmology*, 1989, 73, no. 8, 639-644) as a way of assessing the degree of active disease. This score, based on the classical signs of acute inflammation (pain, redness, swelling, and impaired function) was proposed as a clinical classification to discriminate easily between active and inactive disease and was modified in 1997 (Mourits et al., *Clinical Endocrinology*, 1997. 47, no. 1, 9-14). This protocol is further described below.

As used herein, the term CAS refers to the protocol described and scored as disclosed below. According to this protocol, one point is given for the presence of each of the parameters assessed in the Table below. The sum of all points defines clinical activity and provides the CAS. For patients assessed for the first time only items 1-7 are scored. A CAS≥3/7 indicates active GO. For patients that are assessed for the second or subsequent time (typically, 1-3 months later), items 8-10 are also scored; and a CAS≥4/10 indicates active disease. A ten-item CAS scale exists as well, but in clinical trials, the 7-item scale is generally used, being more amenable to longitudinal studies involving multiple assessments.

The CAS consists of seven components:
1. spontaneous retrobulbar pain,
2. pain on attempted eye movements (upward, side-to-side, and downward gazes),
3. conjunctival redness,
4. redness of the eyelids,
5. chemosis (conjunctival swelling/edema),
6. swelling of the caruncle/plica, and
7. swelling of the eyelids.

Each component is scored as present (1 point) or absent (0 points). The score at each efficacy assessment is the sum of all items present; giving a range of 0-7, where 0 or 1 constitutes inactive disease and 7 severe active ophthalmopathy. A change of >2 points is considered clinically meaningful.

Item 1, spontaneous orbital pain could be a painful, or oppressive feeling on, or behind, the globe. This pain may be caused by the rise in intraorbital pressure, when the orbital tissues volume increases through excess synthesis of extracellular matrix, fluid accumulation, and cellular infiltration and expansion. Item 2, gaze evoked orbital pain, could be pain in the eyes when looking, or attempting to look, up, down or sideways, i.e., pain with upward, downward, or lateral eye movement, or when attempting upward, downward, or lateral gaze. This kind of pain could arise from the stretching of the inflamed muscle(s), especially on attempted up-gaze. The 'stretching pain' cannot be provoked by digital pressing on the eyeball, as would be expected if it were a manifestation of the raised intraorbital pressure. Both kinds of pain can be reduced after anti-inflammatory treatment. These kinds of pain are therefore considered to be directly related to autoimmune inflammation in the orbit and thus useful in assessing TAO activity.

Swelling in TAO is seen as chemosis (edema of the conjunctiva), and swelling of the caruncule and/or plica semilunaris. Both are signs of TAO activity. Swollen eyelids can be caused by edema, fat prolapse through the orbital septum, or fibrotic degeneration. In addition to swelling, other symptoms indicative of active TAO include redness and/or pain of the conjunctiva, eyelid, caruncule and/or plica semilunaris.

Other grading systems have also been developed for the assessment of GO. The VISA Classification (vision, inflammation, strabismus, and appearance) (Dolman, P. J., and Rootman, J., *Ophthalmic Plastic and Reconstructive Surgery*, 2006, 22, no. 5, 319-324 and Dolman, P. J., *Best Practice & Research Clinical Endocrinology & Metabolism*, 2012, 26, no. 3, 229-248) and the European Group of Graves' Orbitopathy (EUGOGO) Classification (Bartalena, L., et al., *European Journal of Endocrinology*, 2008, 158, no. 3, 273-285) are two such examples. Both systems are grounded in the NO SPECS and CAS classifications and use indicators to assess the signs of activity and the degree of severity. More importantly, they allow the clinician to guide the treatment of the patient with GO. VISA is more commonly used in North America and Canada while EUGOGO is in Europe. Since the VISA and EUGOGO protocols are not interchangeable, only one of them should be employed as a reference in a specific patient.

In addition to proptosis (or exophthalmos) and CAS, quality of life (QoL) was also evaluated with the use of the Graves' ophthalmopathy quality of life (GO-QoL) questionnaire. This questionnaire is designed to determine the improved quality of life after treatment. In some embodiments, questionnaire may determine the decreased or lack of side effects after being treated with an antibody, or an antigen binding fragment thereof, according to the methods disclosed herein, as compared to treatment with glucocorticoids.

As described below in Example 5, the questionnaire has two self-assessment subscales. The first relates to the impact of visual function on daily activities, while the second relates to the impact of self-perceived appearance. Each subscale has 8 questions which are answered with: (i) yes—very much so; (ii) yes—a little; or (iii) no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale is considered to be clinically meaningful. The combined score takes raw scores from both subscales and again transforms them to a single 0-100 scale.

Severity Measures

For lid aperture, the distance between the lid margins were measured (in mm) with the patient looking in the primary position, sitting relaxed, and with distant fixation.

For swelling of the eyelids, the measure/evaluation was either "absent/equivocal," "moderate," or "severe."

Redness of the eyelids was either absent or present.

Redness of the conjunctivae was either absent or present.

Conjunctival edema was either absent or present.

Inflammation of the caruncle or plica was either absent or present.

Exophthalmos was measured in millimeter using the same Hertel exophthalmometer and same intercanthal distance for an individual patient.

As described below in Example 10, subjective diplopia was scored from 0 to 3 (0=no diplopia; 1=intermittent, i.e., diplopia in primary position of gaze, when tired or when first awakening; 2=inconstant, i.e., diplopia at extremes of gaze; 3=constant, i.e., continuous diplopia in primary or reading position).

For eye muscle involvement, the ductions were measured in degrees.

Corneal involvement was either absent/punctate or keratopathy/ulcer.

For optic nerve involvement, i.e., best-corrected visual acuity, color vision, optic disc, relative afferent pupillary defect, the condition was either absent or present. In addition, visual fields were checked if optic nerve compression was suspected.

Severity Classification

Sight-threatening thyroid eye disease: Patients with dysthyroid optic neuropathy (DON) and/or corneal breakdown. This category warranted immediate intervention.

Moderate-to-severe thyroid eye disease: Patients without sight-threatening disease whose eye disease had sufficient impact on daily life to justify the risks of immunosuppression (if active) or surgical intervention (if inactive). Patients with moderate-to-severe thyroid eye disease usually had any one or more of the following: lid retraction ≥2 mm, moderate or severe soft tissue involvement, exophthalmos ≥3 mm above normal for race and gender, inconstant or constant diplopia.

Mild thyroid eye disease: Patients whose features of thyroid eye disease have only a minor impact on daily life insufficient to justify immunosuppressive or surgical treatment. They usually have only one or more of the following: minor lid retraction (<2 mm), mild soft tissue involvement, exophthalmos <3 mm above normal for race and gender, transient or no diplopia, and corneal exposure responsive to lubricants.

To facilitate understanding of the disclosure, a number of terms and abbreviations as used herein are defined below as follows:

As used herein, the term "antibody" encompasses the various forms of antibodies including but not being limited to whole antibodies, monoclonal antibodies, antibody fragments, human antibodies, humanized antibodies, chimeric antibodies and genetically engineered antibodies as long as the characteristic properties such as specificity and IGF-IR inhibitory activity are retained.

As used herein, the terms "antigen binding fragment," "fragment," and "antibody fragment" are used interchangeably to refer to any fragment that comprises a portion of a full length antibody, generally at least the antigen binding portion or the variable region thereof. Examples of antibody fragments include, but are not limited to, diabodies, single-chain antibody molecules, multispecific antibodies, Fab, Fab', F(ab')$_2$, Fv or scFv. Further, the term "antibody" as used herein includes both antibodies and antigen binding fragments thereof. In addition, antibody fragments comprise single chain polypeptides having the characteristics of a VH chain, namely being able to assemble together with a VL chain or of a VL chain binding to IGF-IR, namely being able to assemble together with a VH chain to a functional antigen binding pocket and thereby providing the property of inhibiting the binding of IGF-I and IGF-II to IGF-IR.

The terms "monoclonal antibody" or "monoclonal antibody composition," as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light human chain transgene fused to an immortalized cell.

The term "human antibody" as used herein, is intended to include antibodies having variable and constant regions derived from human germline immunoglobulin sequences. The term "humanized antibody" as used herein refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody."

The term "recombinant human antibody," as used herein, is intended to include all human antibodies that are prepared, expressed, created or isolated by recombinant means, such as antibodies isolated from a host cell such as an SP2-0, NS0 or CHO cell or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play an important role in the binding specificity/affinity of antibodies.

The terms "complementarity determining region," "CDR," "hypervariable region," or "antigen-binding portion of an antibody" are used interchangeably herein and refer to the amino acid residues of an antibody which are responsible for antigen-binding. The hypervariable region comprises amino acid residues from the complementarity determining regions or CDRs. "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat et al., Sequences of Proteins of Immunological Interest, 5th Ed. Public Health Service, National Institutes of Health, Bethesda, MD. (1991)) and/or those residues from a "hypervariable loop."

The terms "binding to IGF-IR" or "specific binding to IGF-IR" are used interchangeably herein and mean the binding of the antibody to IGF-IR in an in vitro assay, preferably in a binding assay in which the antibody is bound to a surface and binding of IGF-IR is measured by Surface Plasmon Resonance (SPR). Binding means a binding affinity ($K_D$) of $10^{-8}$ M or less, preferably $10^{-13}$ to $10^{-9}$ M. Binding to IGF-IR can be investigated by a BIAcore assay (Pharmacia Biosensor AB, Uppsala, Sweden). The affinity of the binding is defined by the terms ka (rate constant for the association of the antibody from the antibody/antigen complex), kd (dissociation constant), and $K_D$ (kd/ka). The antibodies used in the methods disclose herein typically show a $K_D$ of about $10^{-9}$ M or less.

The antibodies, or antigen binding fragments thereof, used in the methods disclosed herein inhibit the binding of IGF-I and IGF-II to IGF-IR. The inhibition is measured as $IC_{50}$ in an assay for binding of IGF-I/IGF-II to IGF-IR on cells. Such an assay is known to one of skill in the art and is described, for example, U.S. Pat. No. 7,579,157, which is incorporated herein in its entirety. The $IC_{50}$ values of the antibodies used in the methods disclosed herein for the binding of IGF-I and IGF-II to IGF-IR typically are no more than 2 nM. $IC_{50}$ values are measured as average or median values of at least three independent measurements. Single $IC_{50}$ values may be excluded from the scope.

The term "inhibiting the binding of IGF-I and IGF-II to IGF-IR" as used herein refers to inhibiting the binding of $I^{125}$-labeled IGF-I or IGF-II to IGF-IR presented on the surface of cells in an in vitro assay. Inhibiting means an $IC_{50}$ value of 2 nM or lower.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a subject or patient is intended to include prevention, prophylaxis, attenuation, amelioration and therapy. Treatment may also include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The terms "subject" and "patient" are used interchangeably herein to mean all mammals including humans. Examples of subjects include, but are not limited to, humans, monkeys, dogs, cats, horses, cows, goats, sheep, pigs, and rabbits. In one embodiment, the subject or patient is a human.

The terms "affected with a disease or disorder," "afflicted with a disease or disorder," or "having a disease or disorder" are used interchangeably herein and refer to a subject or patient with any disease, disorder, syndrome or condition. No increased or decreased level of severity of the disorder is implied by the use of one the terms as compared to the other.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

When introducing elements of the present disclosure or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein in relation to a numerical value x means x±10%.

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may optionally be omitted where used herein.

An "intention-to-treat" population includes all clinical trial subjects who are randomized according to randomized treatment assignment. Randomized controlled trials often suffer from two major complications, i.e., noncompliance and missing outcomes. One potential solution to this problem is a statistical concept called intention-to-treat (ITT) analysis. ITT analysis ignores noncompliance, protocol deviations, withdrawal, and anything that happens after randomization. ITT analysis maintains prognostic balance generated from the original random treatment allocation. In ITT analysis, estimate of treatment effect is generally conservative. A better application of the ITT approach is possible if complete outcome data are available for all randomized subjects. Per-protocol population is defined as a subset of the ITT population who completed the study without any major protocol violations. See, e.g., Gupta S K, Intention-to-treat concept: A review, Perspect Clin Res. 2011 July-September; 2(3): 109-112.

The term "teprotumumab," also known as RV-001 and R-1507, is a human monoclonal antibody that binds to insulin-like growth factor-1 receptor (IGF-1R). It has CAS number 1036734-93-6 and comprises a SEQ ID NO.S 1-8 disclosed herein (see, e.g., table 17). It may be referred to in the alternative throughout this disclosure as "Antibody 1."

Antibodies

The sequences of the heavy chains and light chains of examples of antibodies that may be used in the methods of the invention, each comprising three CDRs on the heavy chain and three CDRs on the light chain are provided below. The sequences of the CDRs, heavy chains, light chains as well as the sequences of the nucleic acid molecules encoding the CDRs, heavy chains and light chains of the antibodies are disclosed in the sequence listing. The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRL1 (or LCDR1), CDRL2 (or LCDR2) and CDRL3 (or LCDR3), respectively. Table 1 provides the SEQ ID numbers for the amino acid sequences of the six CDRs of the heavy and light chains, respectively, of the antibodies that may be used in the methods disclosed herein.

TABLE 1

SEQ ID Numbers for CDR Polypeptides of Antibodies that may be used in the methods disclosed herein.

| | SEQ ID NOs. for CDR Polypeptides | | | | | |
|---|---|---|---|---|---|---|
| | CDRH1 | CDRH2 | CDRH3 | CDRL1 | CDRL2 | CDRL3 |
| Antibody 1 | 1 | 2 | 3 | 4 | 5 | 6 |
| Antibody 2 | 1 | 9 | 3 | 4 | 10 | 6 |

In one embodiment, an antibody or antibody fragment useful in the methods disclosed herein comprises at least one CDR with a sequence that has at least 95% sequence identity to any one of SEQ ID NOs: 1-6, 9, or 10 and specifically inhibits (or blocks) Insulin Like Growth Factor-I Receptor (IGF-IR).

In another embodiment, the antibody or antigen binding fragment that can be used in the methods comprising a heavy chain comprises one or more (i.e. one, two or all three) heavy chain CDRs from antibody 1 or antibody 2 and specifically inhibits or blocks IGF-IR.

In yet another embodiment, the antibody or antigen binding fragment useful in the methods disclosed herein comprises a heavy chain CDR1 with the amino acid sequence of SEQ ID NO: 1; a heavy chain CDR2 with the amino acid sequence of SEQ ID NO: 2, or SEQ ID NO: 9; and a heavy chain CDR3 with the amino acid sequence of SEQ ID NO: 3. In some embodiments, the antibody or antibody fragment comprises a heavy chain comprising the amino acid sequence of (i) SEQ ID NO: 1 for CDRH1, SEQ ID NO: 2 for CDRH2 and SEQ ID NO: 3 for CDRH3; or (ii) SEQ ID NO: 1 for CDRH1, SEQ ID NO: 9 for CDRH2, and SEQ ID NO: 3 for CDRH3 and specifically inhibits IGF-IR.

In another embodiment, the antibody or antigen binding fragment that can be used in the methods disclosed herein comprising a light chain comprising one or more (i.e. one, two or all three) light chain CDRs from antibody 1 or antibody 2 and specifically inhibits IGF-IR.

In yet another embodiment, an antibody or antibody fragment useful in the methods disclosed herein comprises a light chain CDR1 with the amino acid sequence of SEQ ID NO: 4; a light chain CDR2 with the amino acid sequence of SEQ ID NO: 5, or SEQ ID NO: 10; and a light chain CDR3 with the amino acid sequence of SEQ ID NO: 6. In some embodiments, the antibody or antibody fragment comprises a light chain comprising the amino acid sequence of (i) SEQ ID NO: 4 for CDRL1, SEQ ID NO: 5 for CDRL2, and SEQ ID NO: 6 for CDRL3; or (ii) SEQ ID NO: 4 for CDRL1, SEQ ID NO: 10 for CDRL2, and SEQ ID NO: 6 for CDRL3.

In one embodiment, the antibody, or antigen binding fragment thereof, comprises all of the CDRs of antibody 1 as listed in Table 1, and specifically inhibits (or blocks) Insulin Like Growth Factor-I Receptor (IGF-IR). In another embodiment, the antibody, or antigen binding fragment thereof, comprises all of the CDRs of antibody 2 as listed in Table 1, and specifically inhibits (or blocks) IGF-IR.

The SEQ ID numbers for the amino acid sequence for the heavy chain variable region (VH) and the light chain variable region (VL) of antibodies useful in the methods disclosed herein are listed in Table 2.

TABLE 2

SEQ ID Numbers for $V_H$ and $V_L$ amino acid for Antibodies that may be used in the methods disclosed herein.

| | $V_H$ amino acid | $V_L$ amino acid |
|---|---|---|
| Antibody 1 | 7 | 8 |
| Antibody 2 | 11 | 12 |

In one embodiment, the antibody or antigen binding fragment that can be used in the methods disclosed herein comprises a heavy chain variable region having an amino acid sequence that is about 70%, 75%, 80%, 85%, 90%, 95%, 97%, 98%, 99% or 100% identical to the sequence recited in SEQ ID NOs: 7 or 11 wherein the antibody specifically inhibits IGF-IR.

In another embodiment, the antibody or antigen binding fragment that can be used in the methods disclosed herein specifically inhibits IGF-IR and comprises a heavy chain variable region comprising the amino acid sequence of SEQ ID NO: 7 and a light chain variable region comprising the amino acid sequence of SEQ ID NO: 8; or a heavy chain variable region comprising the amino acid sequence of SEQ ID NO: 11 and a light chain variable region comprising the amino acid sequence of SEQ ID NO: 12.

Examples of antibodies useful in the methods disclosed herein disclosed herein include, but are not limited to, antibody 1, and antibody 2. In some embodiments, antibody 1 is teprotumumab.

Variant antibodies are also included within the scope of the antibodies to be used in the methods disclosed herein. Thus, variants of the sequences recited herein are also included. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are antibodies to be used in the methods disclosed herein. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences disclosed herein are antibodies to be used in the methods disclosed herein.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Antibodies used with the methods disclosed herein can be coupled to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody and an epitope of interest can be facilitated by attaching a detectable substance to the antibody and detecting the antibody-antigen complex by suitable detection means known to one of skill in the art.

Antibodies, or antigen binding fragments thereof, used with the methods disclosed herein can be of any isotype (e.g., IgA, IgG, IgM i.e. an α, γ or μ heavy chain). In one embodiment the antibody is IgG. Within the IgG isotype, antibodies may be IgG1, IgG2, IgG3 or IgG4 subclass. The antibodies may have a κ or a λ light chain.

The antibodies, or an antigen binding fragments thereof, used with the methods disclosed herein can be administered by any route known to one of skill in the art. Non-exhaustive examples of routes that can be used are provided below.

Pharmaceutical Compositions

The pharmaceutical compositions used in the methods disclosed herein comprise one or more of: the antibodies or antibody fragments described above and a pharmaceutically acceptable carrier or excipient. Although the carrier or excipient may facilitate administration, it should not itself induce the production of antibodies harmful to the subject or individual receiving the composition; nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles, and are known to one of skill in the art.

The antibodies, or an antigen binding fragments thereof, or pharmaceutical compositions used with the methods disclosed herein may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions. Typically, the therapeutic compositions may be prepared as injectables, either as liquid solutions or suspensions. Solid forms suitable for solution in, or suspension in, liquid vehicles prior to injection may also be prepared.

In one embodiment, the antibody, or an antigen binding fragment thereof, or pharmaceutical composition is administered intravenously. In another embodiment, the antibody, or an antigen binding fragment thereof, or pharmaceutical composition is administered by intravenous infusion.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

The methods of the present invention can use an antibody, or an antigen binding fragment thereof, as described above, alone or in combination with other pharmaceutically active compounds, to treat conditions such as those disclosed hereinabove. The additional pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of an antibody, or an antigen binding fragment thereof, of the present invention and one or more additional pharmaceutically active compounds.

In some embodiments, the antibody, or an antigen binding fragment thereof, of the present invention is used in combination with existing therapies, including, but not limited to, corticosteroids; rituximab and other anti-CD20 antibodies; tocilizumab and other anti-IL-6 antibodies; or selenium, infliximab and other anti-TNF☐☐antibodies. In some embodiments, the antibody, or an antigen binding fragment thereof, of the present invention is used in combination with TSHR inhibitors.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1. Description of Randomized, Placebo-Controlled Clinical Trial to Determine the Efficacy and Safety of Teprotumumab (Antibody 1)

A multicenter, double-masked, randomized, placebo-controlled clinical trial was conducted to determine the efficacy and safety of teprotumumab, a human monoclonal antibody and inhibitor of IGF-IR, in patients with active, moderate-to-severe TAO. A total of 88 patients were randomly assigned to receive placebo or active drug administered intravenously once every 3 weeks for a total of eight infusions. The primary end point was the response in the study eye (selected by investigators at baseline as the most affected eye). This response was defined as a reduction of 2 points or more in the Clinical Activity Score (CAS) and a reduction of 2 mm or more in proptosis at week 24. CAS scores could range from 0 to 7, with a score of ≥4 indicating moderate to severe active TAO. Secondary end points, measured as continuous variables, included proptosis, the CAS, and results on the Graves' ophthalmopathy-specific quality-of-life questionnaire. Adverse events were also assessed.

The trial was conducted at 15 sites. Patients were recruited between Jul. 2, 2013, and Sep. 23, 2015. Major inclusion criteria were the following: patients were 18 to 75 years of age, with TAO that were enrolled into the study no more than 9 months after the onset of orbital symptoms, had a Clinical Activity Score of 4 or more on a 7-point scale in the more severely affected (study) eye, and had not received surgical or medical treatment, with the exception of oral glucocorticoids (a cumulative dose of ≤1 g of methylprednisolone or equivalent, with a 6-week washout period). Serum glucose levels in patients with diabetes were well controlled. Female patients had negative pregnancy tests and used approved contraception. Patients with optic neuropathy, severe ocular surface damage, or an improved CAS of 2 points or more between screening and baseline visits were excluded.

The trial comprised three phases: screening (2 to 6 weeks), intervention (24 weeks), and follow-up (48 weeks). Screening involved one to three visits. During the intervention phase, patients were assessed at baseline and every 3 weeks for 24 weeks; efficacy was assessed at weeks 6, 12, 18, and 24. Data from week 24 were used to assess the primary and secondary end points. With the exception of rare instances, at every assessment, patients were evaluated by the same ophthalmologist, who was unaware of the trial-group assignments. A change of 2 points in the 7-component CAS was considered to be clinically relevant. Proptosis was assessed with the use of a Hertel exophthalmometer. Quality of life was evaluated with the use of the Graves' ophthalmopathy-specific quality-of-life questionnaire (GO-QoL), comprising two subscales assessed separately or in combination; scores on each subscale as well as the score on the overall GO-QoL scale had a range of 0 to 100 points. A change of 8 points was considered to be clinically relevant. Subjective diplopia was assessed by categorizing patients according to four grades. A change of one grade was considered to be clinically relevant.

The trial was designed by academic investigators in collaboration with the manufacturer of teprotumumab, which provided primary financial support for the trial and teprotumumab free of charge and was responsible for trial oversight.

Institutional review and ethics committees of the participating centers and the investigators approved the research protocol. An independent data and safety monitoring board oversaw the safety aspects of the trial. Witnessed, written informed consent was obtained from all patients. Data were obtained by the investigators and their staff.

The investigators vouch for the accuracy and completeness of the data generated at their respective institutions. The investigators and the manufacturer vouch for the fidelity of the trial to the protocol.

Example 2. Moieties/Interventions Used in Randomized, Placebo-Controlled Trials Teprotumumab was provided as freeze-dried powder in glass vials. The placebo was 0.9% sodium chloride solution supplied by the research pharmacy. Patients received eight intravenous infusions, one every 3 weeks starting with an initial dose of 10 mg per kilogram of body weight, followed by 20 mg per kilogram for the remaining seven infusions.

Example 3. Randomization and Masking the Trial

The randomized trial was designed to assess efficacy and safety. Patients were randomly assigned in the double-masked intervention phase to either of two intervention groups in a 1:1 ratio in blocks of two, stratified within each clinical center according to smoking status with the use of an interactive Web-response system. Study pharmacists who were aware of the trial-group assignments prepared the masked infusion. The on-site principal investigators could identify a patient's intervention (teprotumumab or placebo) only in the case of an emergency.

Example 4. Calculation of Clinical Activity Score (CAS)

The clinical activity score consists of seven components: spontaneous retrobulbar pain, pain on attempted eye movements (upward, side-to-side, and downward gazes), conjunctival redness, redness of the eyelids, chemosis, swelling of the caruncle/plica, and swelling of the eyelids. Each component was scored as present or absent, 1 or 0. The score at each efficacy assessment is the sum of all items present. This gave a range of 0-7, where 0 or 1 constitutes inactive disease and 7 severe active ophthalmopathy. A change of $\geq 2$ points was considered clinically meaningful.

Example 5. Evaluation of Graves' Ophthalmopathy Quality of Life (GO-QoL)

Quality of life was evaluated with the use of the GO quality of life questionnaire. The questionnaire has two self-assessment subscales; one covering impact of visual function on daily activities, the other assesses the impact of self-perceived appearance. The visual function subscale covers activities such as driving, walking outdoors, reading, watching television, etc. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes—very much so; yes—a little; or no—not at all. Each question is scored 0-2, respectively, and the total raw score is then mathematically transformed to a 0-100 scale, where 0 represents the most negative impact on quality of life, and 100 represents no impact. A change of $\geq 8$ points on the 0-100 scale has been shown to be clinically meaningful. The combined score takes raw scores from both subscales and again transforms them to a single 0-100 scale.

Example 6. Assessment of Gorman Grading of Diplopia

The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of $\geq 1$ grade is considered clinically meaningful.

Example 7. Outcomes of Trials

Patients who had a response were defined as those who met the composite primary end point at week 24. This end point comprised a reduction of 2 points or more in the CAS and a reduction of 2 mm or more in proptosis in the study eye in the absence of a corresponding amount of worsening in the non-study eye. Secondary end points were proptosis and the CAS (both measured as continuous variables over time) and assessment of the patient's quality of life with the use of the GO-QOL instrument (which includes two subscales that measure limitations in visual functioning and psychosocial functioning as a consequence of changed physical appearance). Patients were also categorized according to their level of response. Safety was assessed according to the incidence of adverse events, serious adverse events, and withdrawals due to adverse events.

Example 8. Statistical Analysis of Outcomes of Trials

It was estimated that a sample of 84 patients would provide the trial with a power of 80% or more to detect a between-group difference if 42 patients per trial group had data that could be evaluated. On the basis of published trial results, it was expected that 30% of the patients in the placebo group and 60% of the patients in the teprotumumab group would have a response. All statistical tests were two-sided and performed at the 5% significance level. No interim data analysis was performed. Analyses were performed with the use of SAS software, version 9.1 (SAS Institute), after database lock.

The intention-to-treat population, which included all randomly assigned patients who received at least one infusion, was used to analyze the primary and secondary efficacy outcomes. The safety population, which included all patients who received teprotumumab or placebo, was used for all safety analyses.

In the primary analysis, we used a logistic-regression model with the intervention group as the model effect and smoking as a covariate. Patients who did not have week 24 data for any reason were considered to have treatment failure. Results of a stratified Cochran-Mantel-Haenszel chi-square test, with smoking status as the stratification factor, enabled confirmation of the logistic analysis results.

For assessment of the secondary end points (proptosis, CAS, and GO-QOL scores), a mixed model of repeated measurements was fit to the individual change from baseline with the use of the PROC MIXED procedure in SAS software. Each baseline score (including smoking status, intervention group, time, time according to intervention, and time according to baseline interaction) was incorporated into the analysis. Responses in the nonstudy eye were assessed with the use of identical analyses.

Example 9. Initial Results of Trials

A total of 88 eligible patients underwent randomization. Of these patients, the intention-to-treat population of 87 patients (45 in the placebo group and 42 in the teprotumumab group) had more than one infusion. A total of 39 patients in the placebo group (87%) and 37 patients in the teprotumumab group (88%) completed the intervention as shown in FIG. 1.

As shown in FIG. 1, patients who met the primary inclusion criteria for being enrolled into the study within 9 months or less after the onset of orbital symptoms and who had a Clinical Activity Score of 4 points or more (on a scale from 0 to 7, with a score of ≥3, indicating active TAO, were entered into the screening phase of the trial. One patient who did not meet the screening criteria for an "administrative reason" was screened after the screening period was closed. At the baseline visit (week 0), patients who met all inclusion and exclusion criteria were randomly assigned to receive teprotumumab or placebo in a 24-week intervention phase of the trial. Patients then entered a 1-year follow-up phase, which is ongoing. The intention-to-treat population was defined as all patients who received one infusion of teprotumumab or placebo and excluded one patient who was randomly assigned to teprotumumab but withdrew consent before the drug was administered. One patient discontinued the intervention during the intervention phase but returned for the week 24 assessment.

All patients met criteria for euthyroid status (within ±50% of the reference range) at trial entry; 25 of 87 patients (29%) had minor adjustments in the dose of levothyroxine or an anti-thyroid drug. Although patients were stratified according to smoking status, there was an imbalance between the two groups with respect to this variable (Table 3). The P values associated with the adjusted odds ratios presented in the next section, as well as the P values for the reduced proptosis and the reduction in the CAS (both measured as continuous variables) and for the GO-QOL score, were calculated with the use of analytic methods that adjusted for a potential imbalance in smoking status by including smoking as a covariate.

TABLE 3

Baseline Characteristics of the Patients.*

| Characteristic | Teprotumumab (N = 43) | Placebo (N = 44) |
|---|---|---|
| Demographic and clinical characteristics | | |
| Age - yr | 51.6 ± 10.6 | 54.2 ± 13.0 |
| Female sex - no. of patients (%) | 28 (65) | 36 (82) |
| Time since initiation of treatment for thyroid disease - mo† | | |
| Median | 8 | 15 |
| Range | 1-134 | 3-189 |
| Current treatment for thyroid disease - no. of patients (%) | | |
| Antithyroid drug‡ | 15 (35) | 20 (45) |
| Levothyroxine | 26 (60) | 23 (52) |
| Thyroid extract | 1 (2) | 3 (7) |
| Adjustment of medication at trial entry - no. of patients (%) | | |
| Levothyroxine | 8 (19) | 5 (11) |
| Antithyroid drug | 5 (12) | 7 (16) |
| Duration of eye symptoms or signs - mo | 4.7 ± 2.1 | 5.2 ± 2.3 |
| Duration of Graves' disease - mo | | |
| Median | 10.7 | 10.8 |
| Range | 1.2-228.0 | 1.2-299.0 |
| Smoking status - no. of patients (%)§ | | |
| Nonsmoker | 32 (74) | 26 (59) |
| Smoker | 11 (26) | 18 (41) |
| Biochemical characteristics | | |
| Thyrotropin-binding inhibitory immunoglobulins - % | 51.6 ± 26.9 | 48.7 ± 25.4 |
| Thyroid-stimulating immunoglobulins - % | 422.9 ± 118.1 | 435.1 ± 105.2 |

TABLE 3-continued

Baseline Characteristics of the Patients.*

| Characteristic | Teprotumumab (N = 43) | Placebo (N = 44) |
|---|---|---|
| Mean thyroid hormone levels - pmol/liter¶ | | |
| Free triiodothyronine | 4.8 ± 1.4 | 4.9 ± 1.7 |
| Free thyroxine | 16.3 ± 4.8 | 16.3 ± 3.6 |
| Levels of free triiodothyronine and free thyroxine - no. of patients (%) | | |
| Euthyroid at baseline and through intervention phase | 20 (46) | 13 (30) |
| Values occasionally outside normal range during intervention phase | 18 (42) | 25 (57) |
| Sustained out-of-range values during intervention phase | 5 (12) | 6 (14) |

*Plus-minus values are means ± SD. Additional patient characteristics are provided in Table S2. Patients were recruited in the following countries: Germany (19 patients), Italy (6), the United Kingdom (10), and the United States (53). A breakdown of randomization according to clinical center is provided in Table S3. Unless otherwise stated, baseline characteristics shown are from the safety population (44 patients in the placebo group and 43 patients in the teprotumumab group), which differs from the intention-to-treat population (45 patients in the placebo group and 42 patients in the teprotumumab group), since 1 patient in the placebo group received teprotumumab in error.
†Data shown are for 10 patients in the placebo group and 10 patients in the teprotumumab group.
‡The antithyroid drugs were carbimazole, methimazole, and propylthiouracil.
§Data for smoking status were based on patients who were current smokers at the time of the screening visit. Patients were stratified at randomization according to smoking status to balance the trial groups with respect to this known risk factor for thyroid-associated ophthalmopathy. However, there were imbalances in randomization blocks and discrepancies between patients who were randomly assigned to an intervention as nonsmokers at week 0 and those recorded as being smokers in their case-report forms. Data from the case-report forms were considered to be more accurate and were used to define smoking status at baseline.
¶The normal ranges of free triiodothyronine are 2.3 to 4.2 pg per milliliter (3.5 to 6.5 pmol per liter), and of free thyroxine, 0.9 to 1.8 ng per deciliter (11.6 to 23.2 pmol per liter).

Example 10. Primary and Secondary End Points from Trials

Proptosis, the Clinical Activity Score, and the GO-QOL score were nearly identical at baseline in the two groups (Table 4). At baseline, there was an imbalance between the groups with respect to diplopia, with a higher occurrence in the teprotumumab-group.

Figure 2:
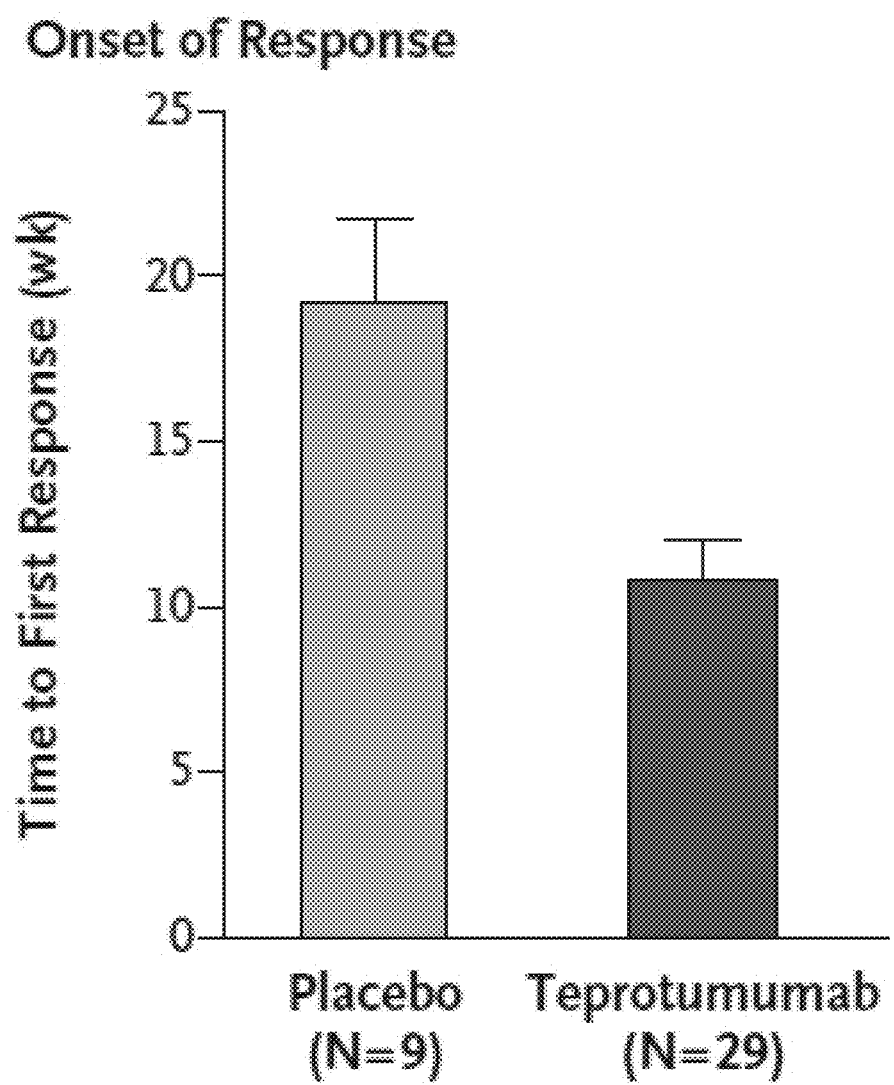
FIGS. 2-4 show the primary efficacy endpoints of the clinical studies for the teprotumumab and placebo groups.
Figure 3:
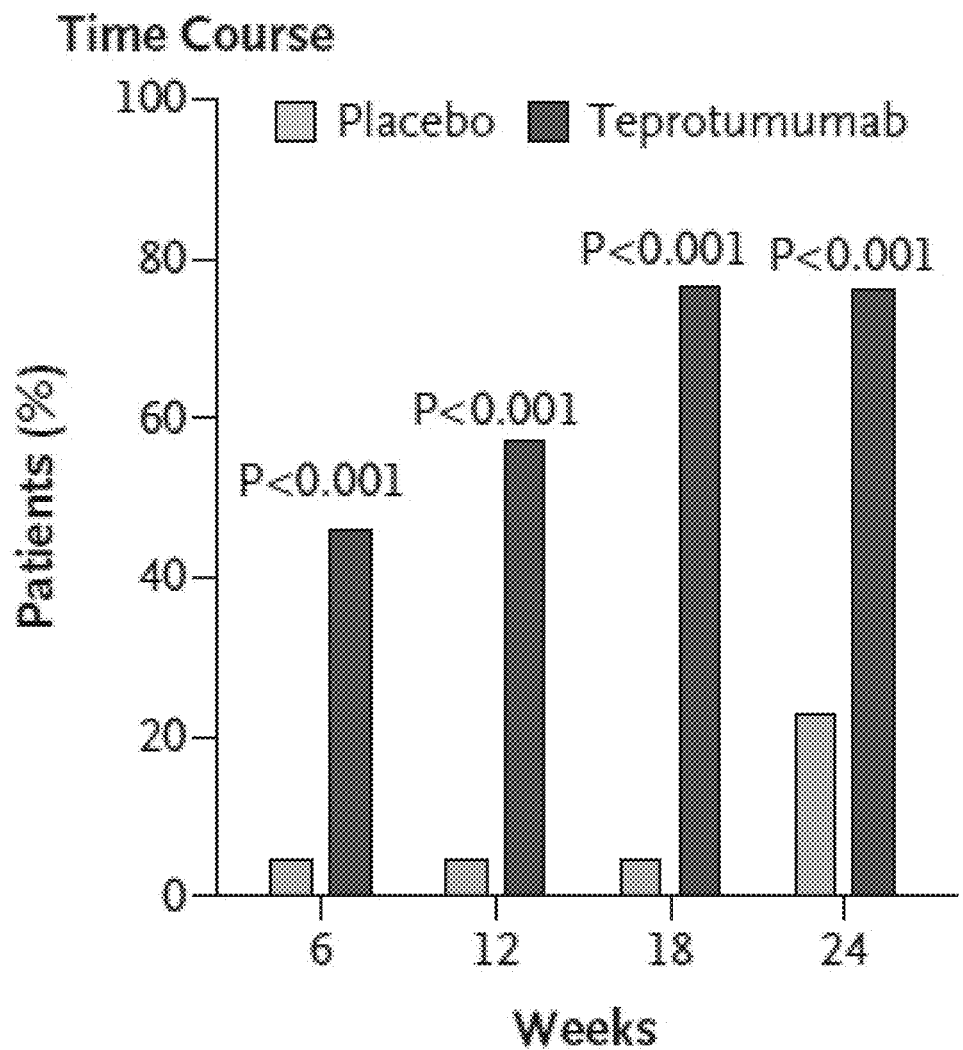

In the primary outcome measure in the intention-to-treat population, 9 of 45 patients who received placebo (20%) and 29 of 42 patients who received teprotumumab (69%) had a response at week 24 (adjusted odds ratio, 8.86; P<0.001). Similarly, in the per-protocol population, 8 of 36 patients who received placebo (22%) and 26 of 33 patients who received teprotumumab (79%) had a response at week 24 (adjusted odds ratio, 12.73; P<0.001). The time to the first response was markedly shorter in the teprotumumab group than in the placebo group (FIG. 2). The onset of the response was rapid. The proportion of patients who had a response was greater in the teprotumumab group than in the placebo group at weeks 6, 12, and 18 (P<0.001 for all comparisons) (FIG. 3). In a separate analysis that graded the level of response, more patients in the teprotumumab group than in the placebo group had reductions of 3 points or more in the CAS and reductions of 3 mm or more in proptosis (P<0.001 for the comparisons at every level of response) (FIG. 4).

Figure 4:
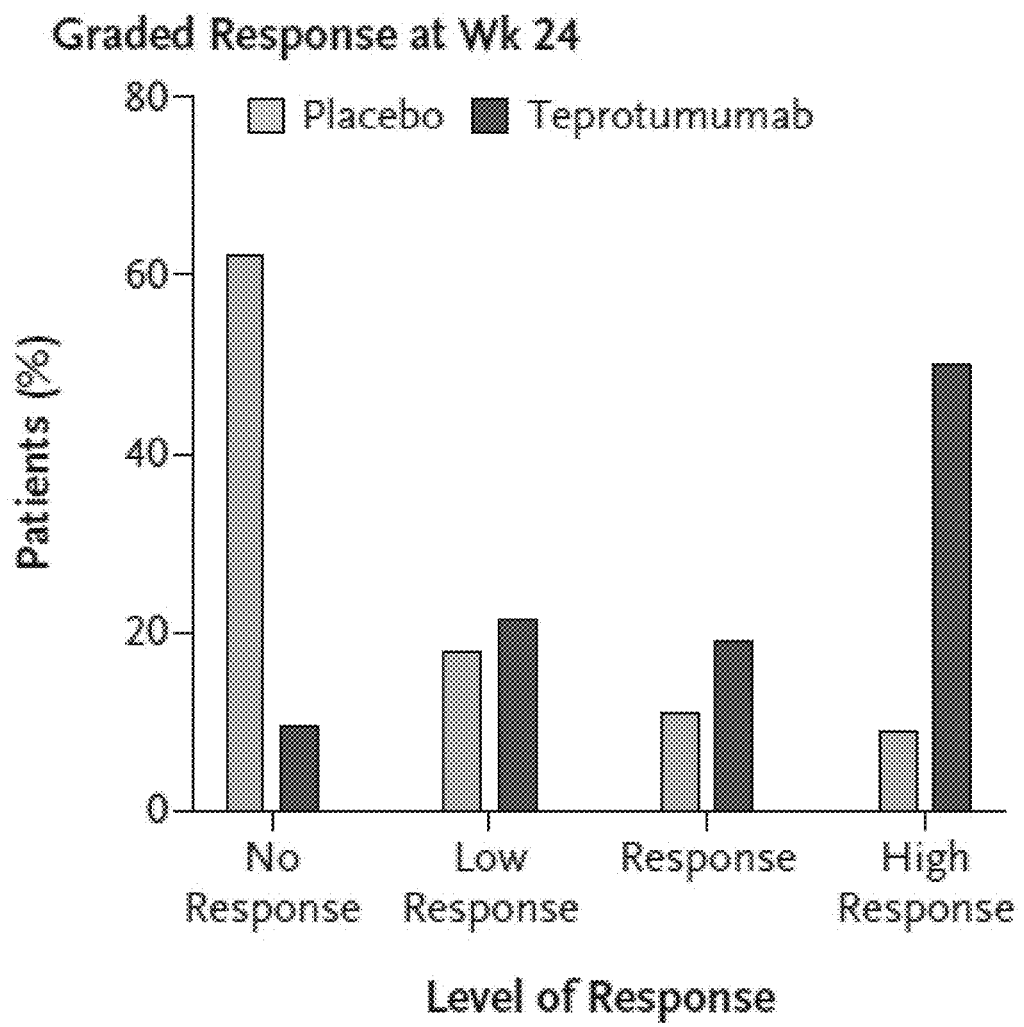

As shown in FIG. 2-4, the primary end point was a logistic regression of response status according to trial-drug group at week 24. A response was defined as a reduction of 2 mm or more in proptosis and a reduction of 2 points or more in the CAS in the study eye, without an equivalent increase in proptosis or in the CAS in the non-study eye. The CAS, which comprises seven components, ranges from 0 to 7, and a change of 2 points is considered to be clinically relevant. As shown in Panel B, in the analysis of the time to first response, data are expressed as means±SE. As shown in Panel C, in the analysis of the time course in patients who met the response criteria, P values were calculated with the use of a logistic-regression model. As shown in Panel D, in the grading of a response at week 24, P<0.001 was calculated with the use of a logistic-regression model. A high response indicates that proptosis was reduced by 3 mm or more and the CAS was reduced by 3 points or more. A response indicates a reduction of 2 mm or more, but less than 3 mm, in proptosis and 2 points or more, but less than 3 points, in the CAS. A low response indicates reductions of 1 mm or more, but less than 2 mm, in proptosis and 1 point or more, but less than 2 points, in the Clinical Activity Score. No response indicates that the patient did not meet any response criteria or had missing evaluations at week 24.

Figure 5:
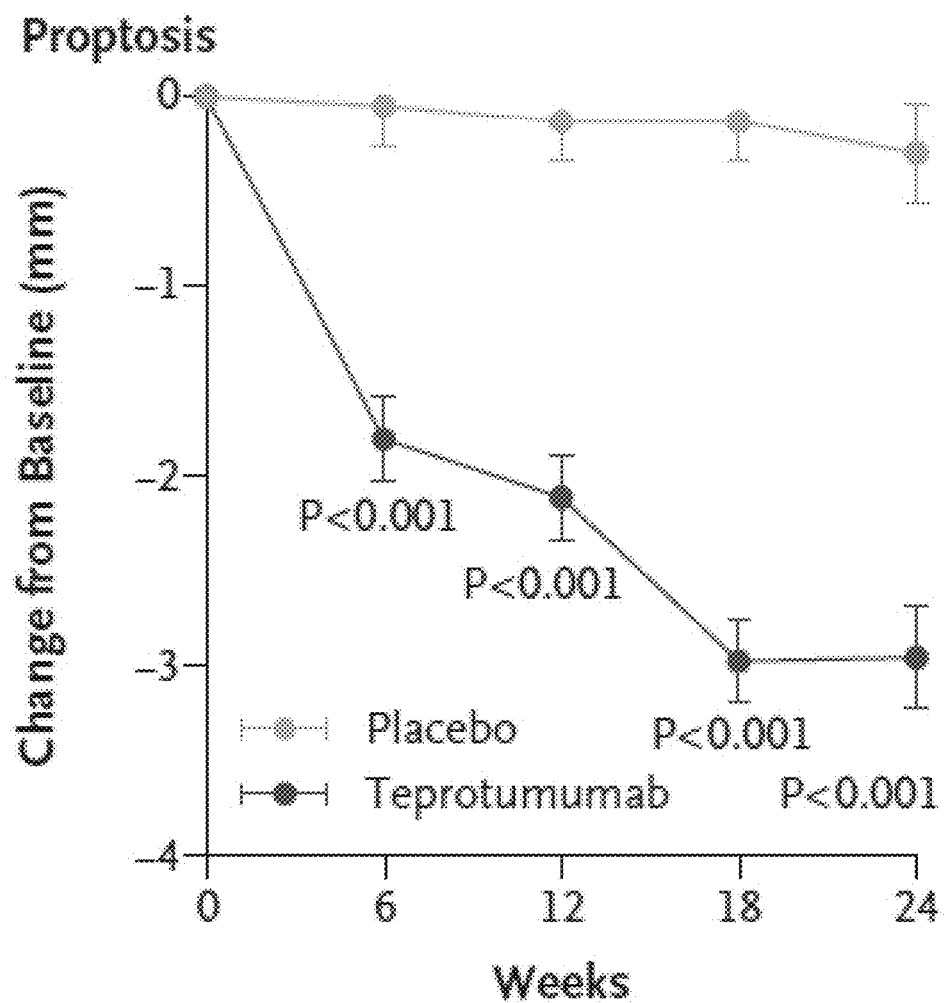
FIGS. 5-10 show the secondary efficacy end points for the teprotumumab group and the placebo group from the trial.

At weeks 6, 12, 18, and 24, the reduction in proptosis from baseline, measured as a continuous variable, was significantly greater in patients who received teprotumumab than in those who received placebo (P<0.001 for all comparisons) (FIG. 5). At week 24, a total of 17 of 42 patients (40%) who received teprotumumab had a reduction of 4 mm or more in proptosis, as compared with 0% of patients who received placebo.

Figure 6:
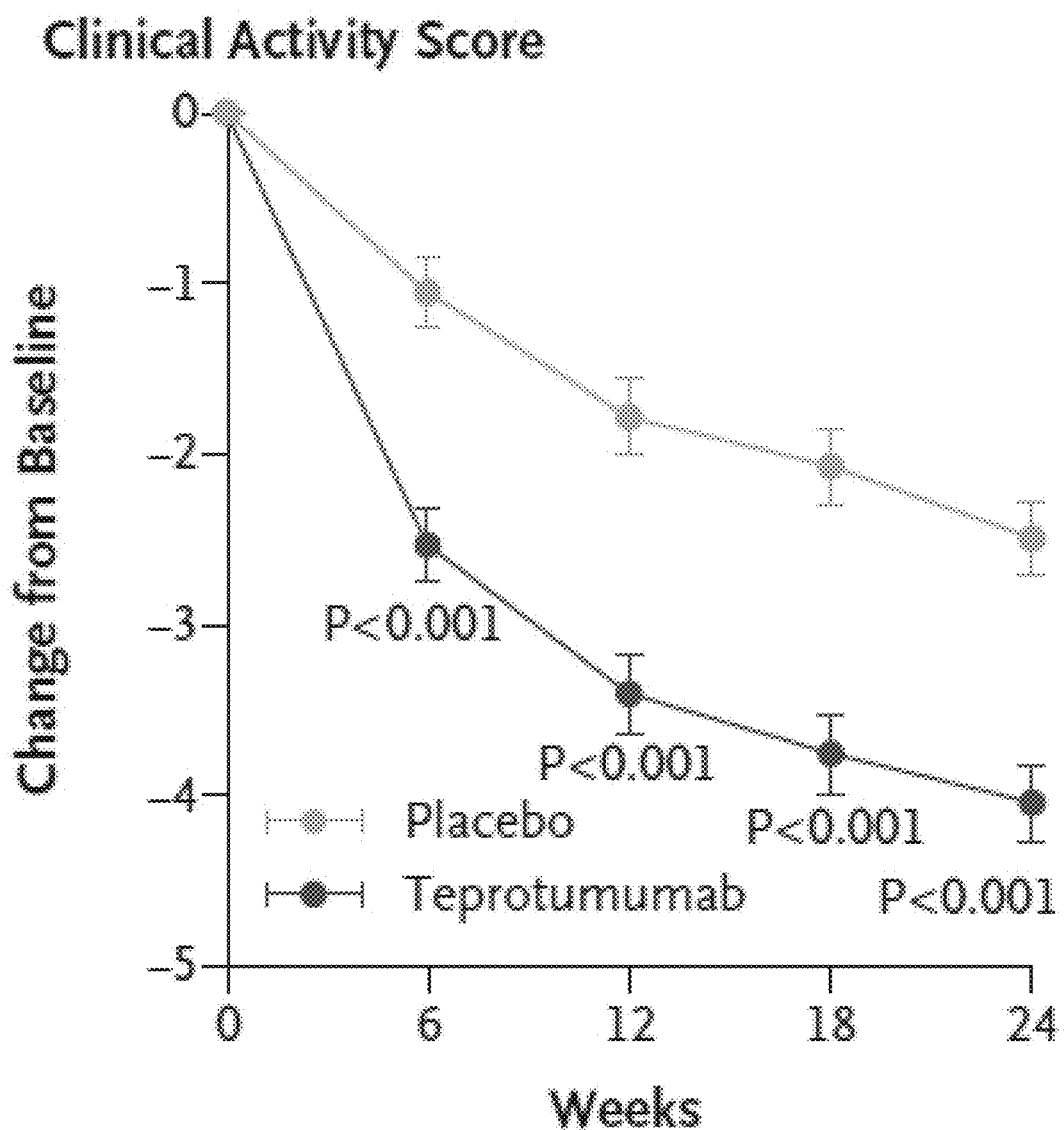
Figure 7:
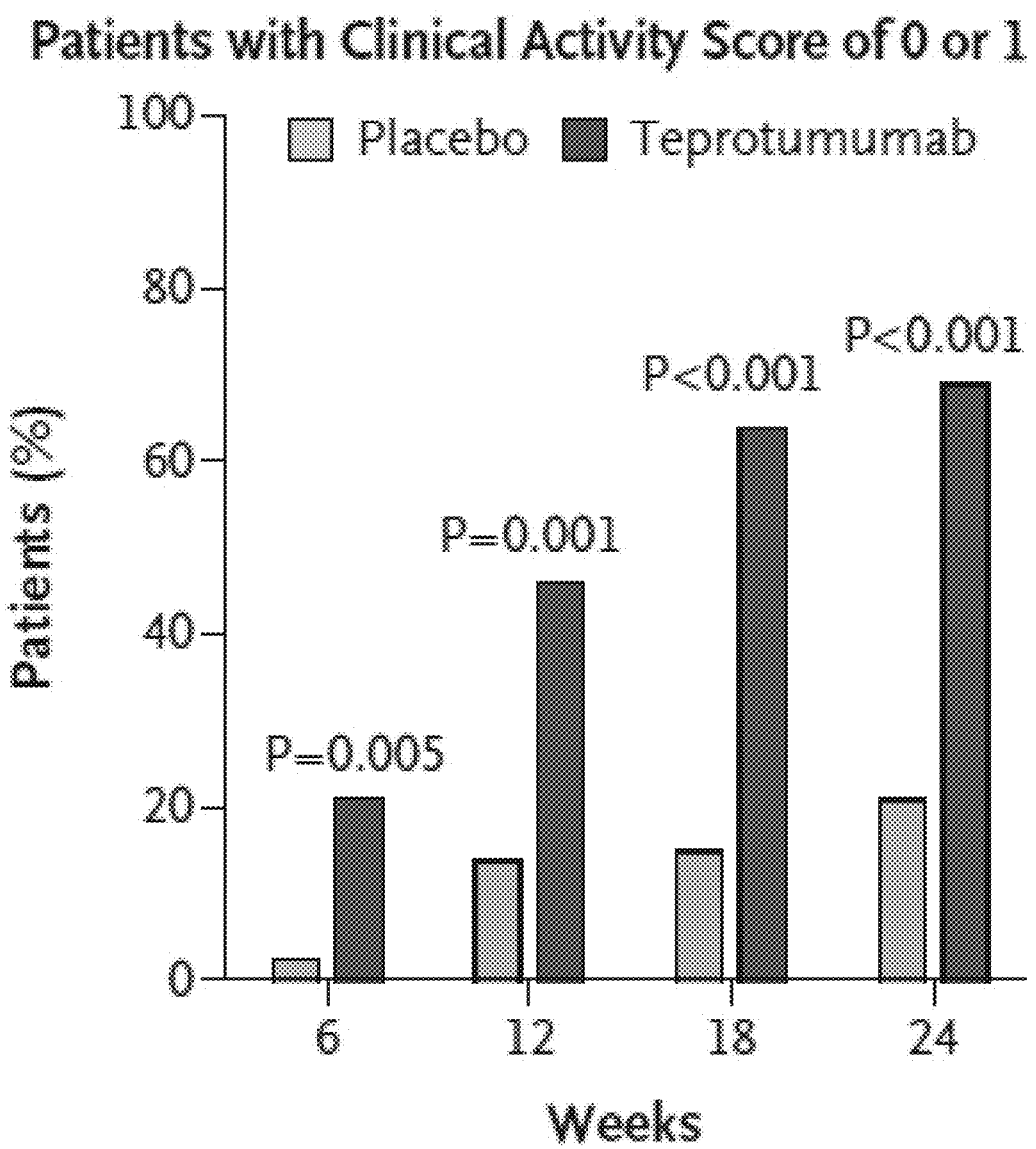

At weeks 6, 12, 18, and 24, the reduction in the Clinical Activity Score in the teprotumumab group was also significantly greater than that in the placebo group (P<0.001 for all comparisons) (FIG. 6), although this score also decreased markedly and progressively in the placebo group. The baseline Clinical Activity Score in the teprotumumab group was 5.1 points, and the mean reduction at week 24 was 4 points. This indicates that some patients had a near-maximal therapeutic effect. This finding was confirmed by a post hoc categorical analysis involving patients who had a CAS of 0 points or 1 point; this analysis showed that 69% of the patients who received teprotumumab had a Clinical Activity Score of 0 or 1 at week 24, as compared with 21% of the patients who received placebo (adjusted odds ratio, 8.97; P<0.001) (FIG. 7). A post hoc analysis showed that the reductions in the CAS in the teprotumumab group were broad-based (i.e., they were not driven by large decreases in subsets of the CAS components). Reductions in the CAS seen in the placebo group were similarly broad-based.

Figure 8:
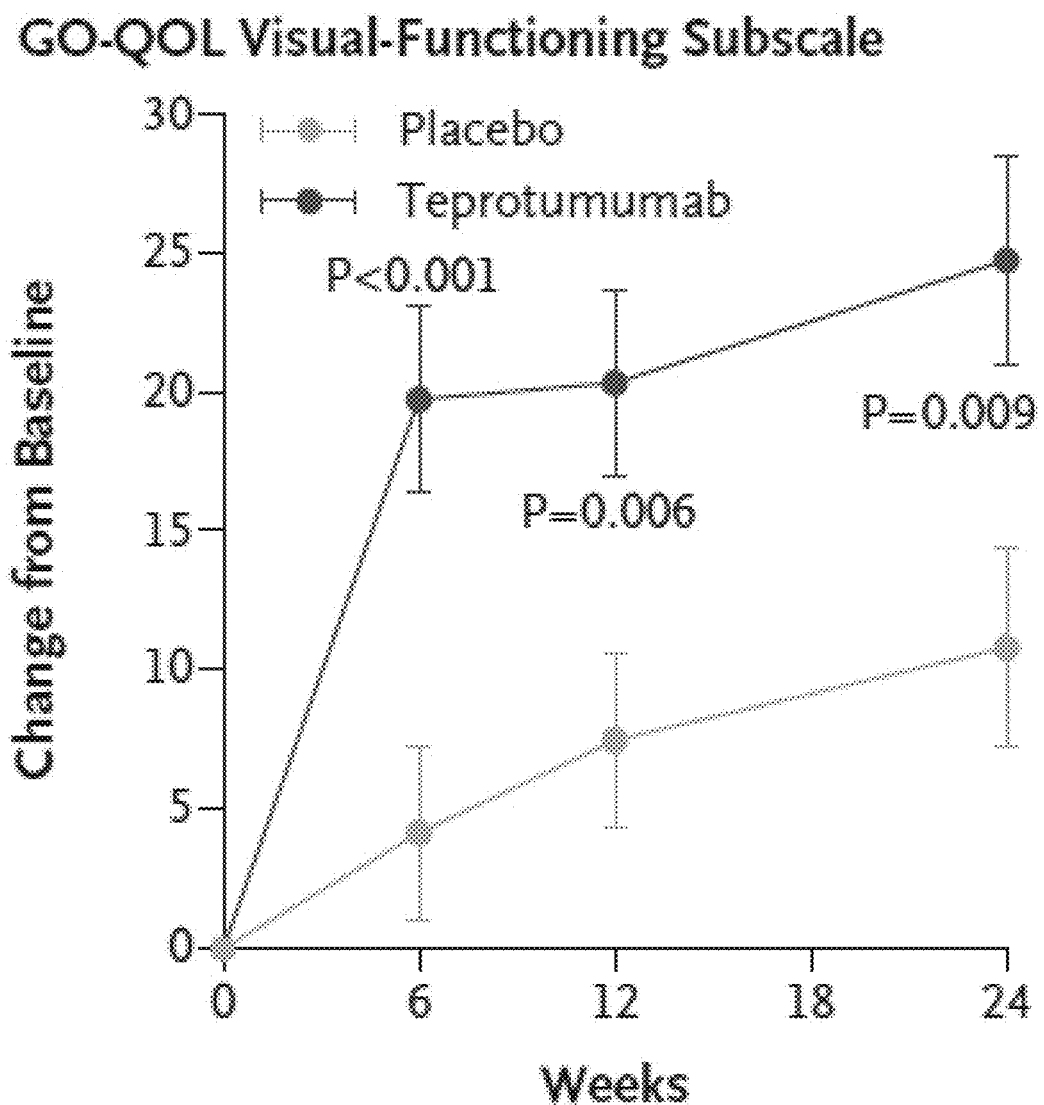
Figure 9:
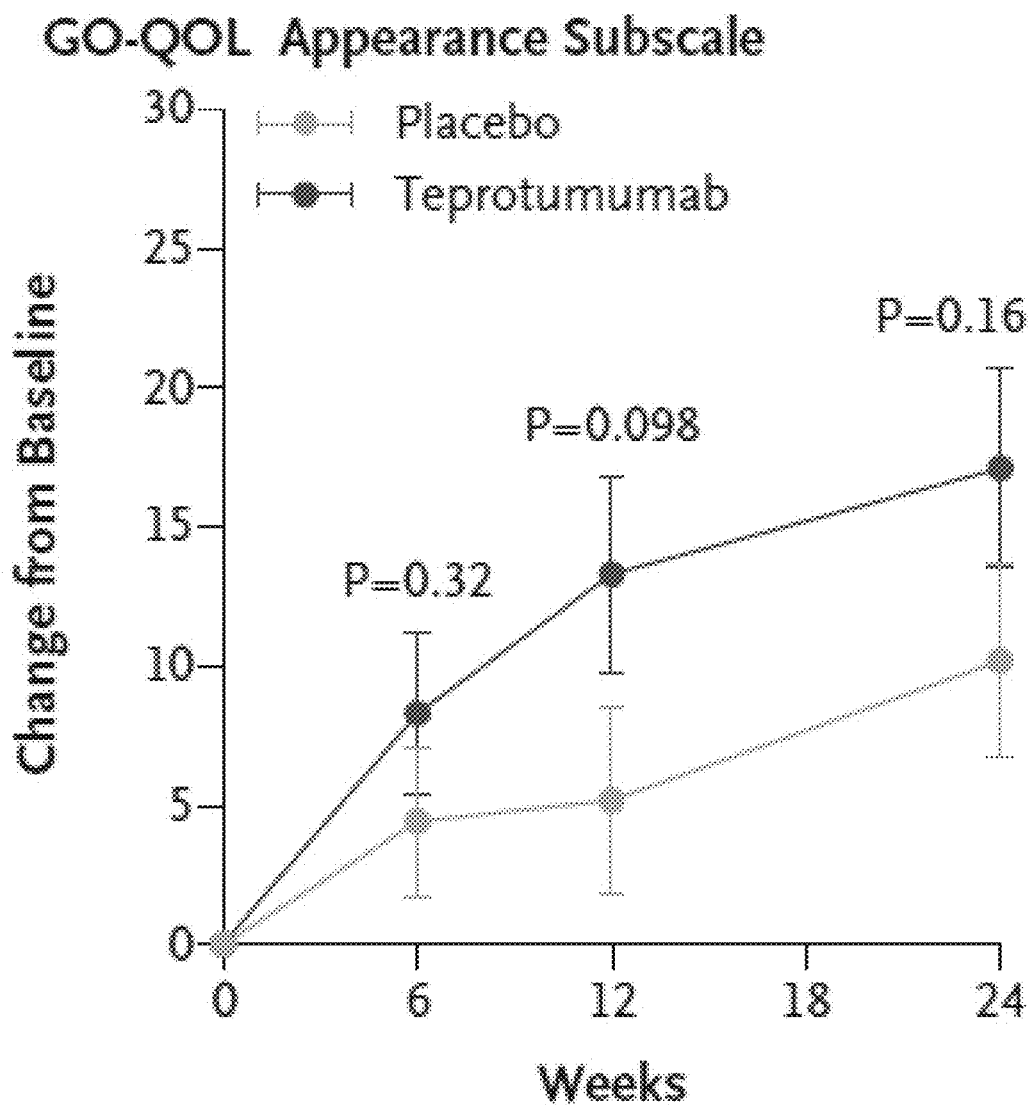
Figure 10:
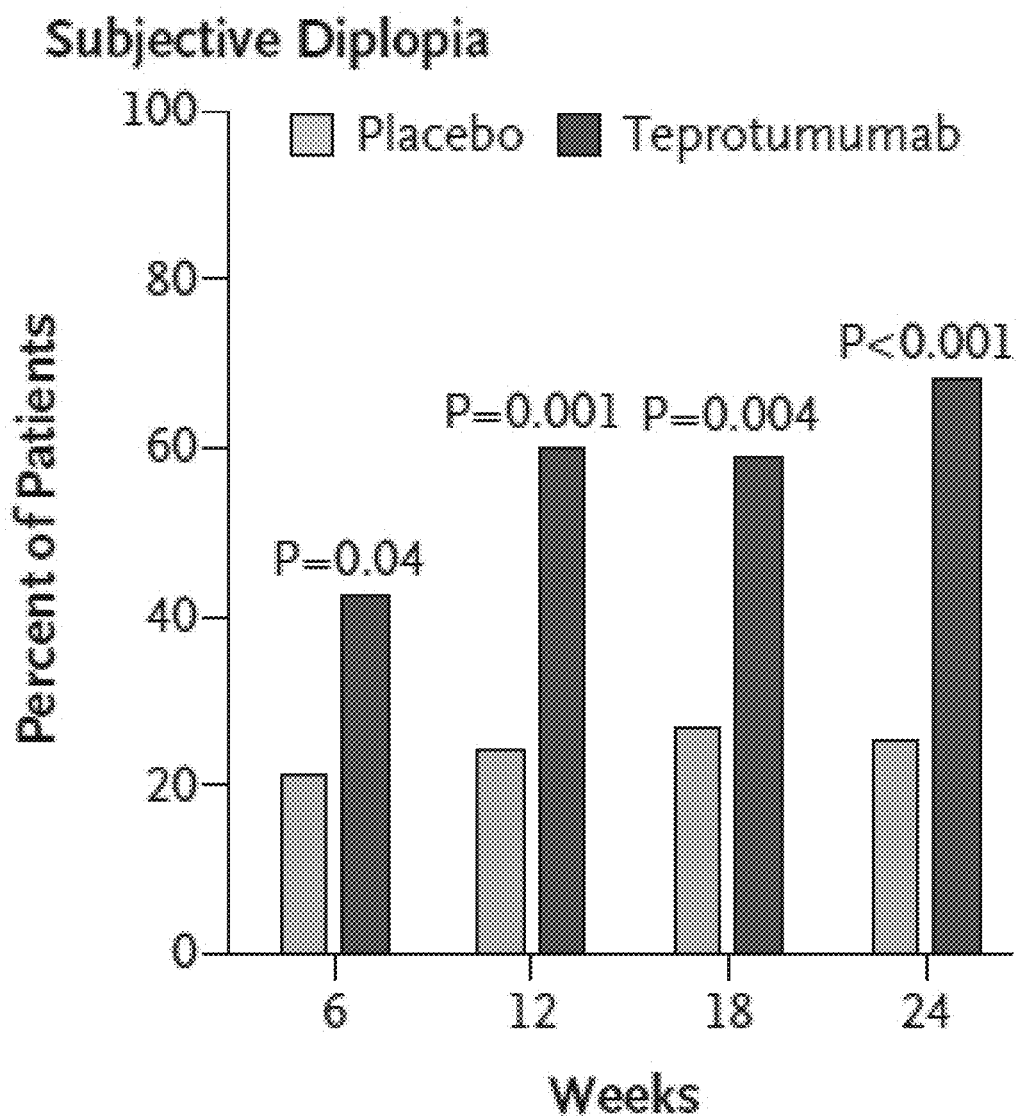

The GO-QOL visual-functioning score increased significantly in the teprotumumab group at all time points (FIG. 8). This increase ranged from 12.8 to 15.6 points greater than the increase in the placebo group. On the GO-QOL appearance subscale, a consistent trend toward improvement emerged but did not achieve significance (FIG. 9). When the two scales were combined, significance was seen at weeks 6, 12, and 24 (P=0.003, P=0.007, and P=0.012, respectively) (Table 4). Response rates with respect to subjective diplopia were also significantly higher in the teprotumumab group than in the placebo group (FIG. 10).

Efficacy was also assessed at week 28 (7 weeks after the final dose was administered), and this assessment showed no evidence of diminution (i.e., no "rebound" phenomenon). Indeed, the numbers of patients with a response increased and proptosis and the CAS were further reduced at week 28 as compared with week 24. The efficacy of teprotumumab in the non-study eye was also similar to the efficacy in the study eye with respect to response rates, proptosis, and the CAS. Serum assays showed no drug-induced changes in interleukin-6, interleukin-16, and RANTES (regulated on activation, normal T-cell expressed and secreted) levels. During the intervention phase, levels of thyroid-stimulating immunoglobulins and thyrotropin-binding inhibitory immunoglobulins decreased progressively (by 15 to 30%) in the two groups.

TABLE 4

Results of Efficacy Assessment before and after Administration of Trial Drug.*

| Variable | Teprotumumab (N = 42) | Placebo (N = 45) | Odds Ratio (95% CI) | P Value |
|---|---|---|---|---|
| Response analysis | | | | |
| Primary outcome measure: response in study eye at wk 24 - no. of patients/total no. (%)† | | | | |
| Intention-to-treat population | 29/42 (69) | 9/45 (20) | 8.86 (3.29-23.8) | <0.001 |
| Per-protocol population | 26/33 (79) | 8/36 (22) | 12.73 (4.01-40.4) | <0.001 |
| Time to first response - wk | 11.2 ± 6.6 | 18.7 ± 7.6 | | NC |
| Graded response - no. of patients (%)‡ | | | 11.80 (4.72-29.5) | <0.001 |
| High response | 21 (50) | 4 (9) | | |
| Response | 8 (19) | 5 (11) | | |
| Low response | 9 (21) | 8 (18) | | |
| No response or missing data | 4 (10) | 28 (62) | | |
| Proptosis - mm | | | | |
| Baseline | 23.4 ± 3.2 | 23.1 ± 2.9 | | |
| Change from baseline | −2.46 ± 0.20 | −0.15 ± 0.19 | | <0.001 |
| Clinical Activity Score§ | | | | |
| Baseline | 5.1 ± 0.975 | .2 ± 0.74 | | |
| Change from baseline | −3.43 ± 0.18 | −1.85 ± 0.17 | | <0.001 |
| GO-QOL score¶ | | | | |
| Combined visual-functioning and appearance subscales | | | | |
| Baseline | 34.5 ± 7.3 | 34.5 ± 6.8 | | |
| Change from baseline | 17.7 ± 2.4 | 6.8 ± 2.3 | | <0.01 |
| Visual-functioning subscale | | | | |
| Baseline | 16.9 ± 4.4 | 17.8 ± 4.3 | | |
| Change from baseline | 21.7 ± 2.9 | 7.5 ± 2.7 | | <0.001 |
| Appearance subscale | | | | |
| Baseline | 17.6 ± 4.51 | 6.7 ± 3.8 | | |
| Change from baseline | 12.9 ± 2.8 | 6.6 ± 2.7 | | 0.1 |
| Subjective diplopia‖ | | | | |
| Baseline according to grade - no. of patients (%) | | | 3.78 (1.68-8.54)** | 0.001 |
| No diplopia | 4 (10) | 14 (31) | | |
| Intermittent | 16 (38) | 19 (42) | | |
| Inconstant | 7 (17) | 8 (18) | | |
| Constant | 15 (35) | 4 (9) | | |
| Wk 24 according to grade - no. of patients (%) | | | | |
| No diplopia | 21 (50) | 18 (40) | | |
| Intermittent | 4 (10) | 8 (18) | | |
| Inconstant | 9 (21) | 7 (16) | | |
| Constant | 4 (10) | 6 (13) | | |

TABLE 4-continued

Results of Efficacy Assessment before and after Administration of Trial Drug.*

| Variable | Teprotumumab (N = 42) | Placebo (N = 45) | Odds Ratio (95% CI) | P Value |
|---|---|---|---|---|
| Wk 24 response - no. of patients/total no. (%) | 26/38 (68) | 10/39 (26) | | <0.001 |

*Plus-minus values are means ± SD, except for the change from baseline in proptosis, which is expressed as means ± SE. CI denotes confidence interval, and NC not calculated;
†The primary outcome measure was analyzed with the use of a logistic-regression model that included smoking as a covariate, with a supporting sensitivity analysis conducted in the per-protocol population. The intention-to-treat population, defined as all patients who received an infusion of placebo or teprotumumab, excluded one randomly assigned patient who withdrew consent before drug administration. Secondary end points, analyzed hierarchically, were the Graves' ophthalmopathy- specific quality-of-life (GO-QoL) combined score, proptosis, the Clinical Activity Score, the GO-QoL visual-functioning score, and the GO-QoL appearance score. These continuous variables were analyzed with the use of a mixed model of repeated measurements with smoking as a covariate. Any apparent discrepancies between the tabulated mixed model of repeated-measurements calculations for change from baseline and data plotted in the figures are because tabulated data are an average difference between the trial groups over all post-baseline time points up to week 24. Values plotted in the figures are calculations of the mean change from baseline for specific time points. Prespecified exploratory end points included the time to first response, graded response, and subjective diplopia.
‡A high response indicates that proptosis was reduced by 3 mm or more and the Clinical Activity Score was reduced by 3 points or more. A response indicates a reduction of 2 mm or more but less than 3 mm in proptosis and 2 points or more but less than 3 points in the Clinical Activity Score. A low response indicates reductions of 1 mm or more but less than 2 mm in proptosis and 1 point or more but less than 2 points in the Clinical Activity Score. No response indicates that the patient did not meet any response criteria or had missing evaluations at week 24. The P value for the comparison of placebo with teprotumumab was calculated for the overall distribution of graded responses, with the use of a logistic-regression model for cumulative logits.
§The Clinical Activity Score comprised seven components. Scores range from 0 to 7, and a change of 2 points is considered to be clinically relevant.
¶Quality of life was evaluated with the use of the GO-QoL questionnaire.24 The GO-QoL comprises two subscales, and scores on each subscale as well as the score on the overall GO-QOL scale have a range of 0 to 100 points. A change of 8 points is considered to be clinically relevant.
||Subjective diplopia was assessed on the basis of four grades, and a change of one grade or more is considered to be clinically relevant. A response in patients with diplopia was defined as a decrease of one grade or more. The chi-square test was used to compare data from patients who had a response with data from those who did not at week 24.
**The estimated odds ratio shown was calculated with the use of logistic regression for cumulative logits. This imbalance should be viewed in light of the large number of characteristics assessed at baseline. A sensitivity post hoc logistic-regression analysis of the week 24 response, which included adjustment for baseline smoking status, sex, study eye, and diplopia, did not show a substantial difference from the primary analysis (adjusted odds ratio, 8.16; P < 0.001).

Example 11. Safety During the Trials

Adverse events that emerged during the intervention phase, that occurred in more than 5% of patients in the teprotumumab group, and that were greater in number in the teprotumumab group than in the placebo group are listed in Table 5. The majority of adverse events were mild, involved no treatment, and resolved while the patients continued to receive the intervention. Hyperglycemia, the only adverse event clearly identified by the investigators as being related to teprotumumab, was monitored by assessing blood glucose and glycated hemoglobin levels. Hyperglycemia in patients who did not have diabetes was uniformly grade 1, was intermittent, and occurred at similar rates in the two groups. Grade 2 or 3 hyperglycemia occurred in some patients with diabetes who received teprotumumab, and it was well controlled after adjustment of the medication for diabetes. Glycemic control, assessed according to the glycated hemoglobin level, was similar to that at baseline levels after the intervention phase in all patients who received antibody.

No deaths occurred during the trial. A total of 6 patients in each group discontinued the intervention. Serious adverse events occurred in 5 of 43 patients in the teprotumumab group (12%) and in 1 of 45 patients in the placebo group (2%) (Table 5). Two serious adverse events (diarrhea and mental confusion) in patients who received teprotumumab were categorized by the investigators as "possibly related" to the drug. Other serious adverse events were categorized as "unrelated." Although designated as having a nonresponse treatment failure in the analyses, these 5 patients all met response criteria at their early withdrawal visit. Antidrug antibodies were detected in 1 patient in the teprotumumab group at baseline and in 1 patient during the intervention phase (week 3). Both patients tested negative on subsequent visits (at weeks 9 and 24), and neither patient had neutralizing antibodies; using the term in the context that neither had marked reductions in plasma levels of teprotumumab. Four patients in the placebo group tested positive for antidrug antibodies at baseline; all were graded as having low-level antibody responses.

TABLE 5

Adverse Events and Serious Adverse Events During Intervention.

| Variable | Teprotumumab (N = 43)* number of patients (percent) | Placebo (N = 44)* | Summary Details of Adverse Events in Teprotumumab Group |
|---|---|---|---|
| Adverse event† | | | |
| Nausea | 8 (19) | 4 (9) | Generally mild and reported after first and second infusions |
| Muscle spasms | 8 (19) | 2 (5) | Intermittent, 2 of 8 patients had muscle spasms for >1 wk and received muscle relaxants |
| Diarrhea | 6 (14) | 2 (5) | Treatment occurred in 2 of 6 patients, 1 case designated as a serious adverse event (see below) |
| Hyperglycemia | 5 (12) | 2 (5) | Mechanism-based adverse event |
| Alopecia | 3 (7) | 2 (5) | All mild and no treatment necessary |
| Dry skin | 3 (7) | 0 | All mild, 1 patient used topical dry-skin cream |
| Dysgeusia on days 1-2 | 3 (7) | 0 | In 2 of 3 patients, a transient "metallic" taste reported |

TABLE 5-continued

Adverse Events and Serious Adverse Events During Intervention.

| Variable | Teprotumumab (N = 43)* number of patients (percent) | Placebo (N = 44)* | Summary Details of Adverse Events in Teprotumumab Group |
|---|---|---|---|
| Headache | 3 (7) | 2 (5) | Generally mild, 1 patient took paracetamol |
| Paresthesia | 3 (7) | 0 | "Tingling" reported in nose, feet, or chest; variable onset and in 2 of 3 patients occurred on 1 day |
| Hearing impairment | 3 (7) | 0 | Disparate symptoms, onset, and duration (i.e., one case of unilateral hearing impairment with onset 16 wk after end of therapy, ‡ one case of mild bilateral hearing impairment that resolved, and one case of tinnitus in a patient with a history of tinnitus) |
| Weight loss | 3 (7) | 0 | Variable timing; decreases ranged from 5-9 lb (11-20 kg) |
| Any adverse event | 32 (74) | 32 (73) | |
| Serious adverse event§ | | | |
| Optic neuropathy¶ | 0 | 1 (2) | |
| Diarrhea | 1 (2) | 0 | Severe diarrhea in 1 patient with a 6-mo history of ulcerative colitis |
| Inflammatory bowel disease | 1 (2) | 0 | In 1 patient with recent diagnosis of ileitis and colitis, inflammatory bowel disease diagnosed and treated while patient received trial drug |
| *Escherichia* sepsis‖ | 1 | (2) 0 | *Escherichia coli* infection of unknown origin treated with intravenous antibiotics |
| Hashimoto's encephalopathy | 1 (2) | 0 | Provisional diagnosis after episodic mental confusion with no other neurologic symptoms |
| Urinary retention | 1 (2) | 0 | Diagnosed after patient had an inguinal herniorrhaphy |
| Any serious adverse event | 5 (12) | 1 (2) | |

*One patient in the placebo group received a single dose of teprotumumab in error at week 15. That patient is included here in the teprotumumab group.
†Adverse events of any cause were defined as those that occurred between the administration of the first dose and 30 days after the administration of the final dose. Listed adverse events that emerged during the intervention phase are those that occurred in more than 5% of patients in the teprotumumab group and that occurred in greater numbers in the teprotumumab group than in the placebo group. Patients may have had more than one adverse event.
‡ This case is included because the patient had unrelated, transient eustachian-tube dysfunction while receiving teprotumumab.
§Listed are all serious adverse events reported in the trial, including any adverse event involving hospitalization. In the teprotumumab group, four patients discontinued the intervention because of the following serious adverse events: diarrhea that occurred after six infusions, inflammatory bowel disease after seven, *Escherichia coli* sepsis after three, and Hashimoto's encephalopathy after six.
¶A total of three patients in the placebo group withdrew from the trial because of worsening eye symptoms or a lack of response. One case of dysthyroid optic neuropathy designated by an investigator as a serious adverse event occurred 3 days after the week 24 evaluation.
‖This patient was the only one whose intervention was unmasked during the course of the trial.

Example 12. Summary and Conclusions from Trial-Based Data

Patients who received antibody had reductions in proptosis, the Clinical Activity Score, the GO-QOL (both the visual-functioning subscale and combined scales), and subjective diplopia that were clinically meaningful and significant (P≤0.001) for all comparisons with placebo. Without being bound to any particular theory, the reductions observed across all components of the CAS suggest a therapeutic mechanism upstream from the inflammation in orbital tissues. The marked reduction in proptosis is similar to that reported after decompression surgery, without any risks or dangers associated with orbital surgery. Orbital surgery can provoke reactivation of ophthalmopathy and can cause or exacerbate strabismus; no such dangers arise in the methods disclosed herein. Taken together, the above studies suggest that the methods disclosed herein that recite inhibition of IGF-IR in patients with ophthalmopathy, may result in a disease-modifying reduction in the volume of orbital fat, muscles, or both.

Example 13. Teprotumumab (Antibody 1) Reduces the Primary Outcome of Both CAS and Proptosis Further to the multicenter, double-masked, randomized, placebo-controlled, phase-two trial of 88 patients with clinically active and moderate-to-severe GO described in Example 1 and the data obtained therefrom (described in the above examples), extended primary and secondary outcome analyses was conducted.

To follow-up patients seven weeks after completion of treatment, mean, percent and individual outcomes in teprotumumab (Tepro) intent-to-treat patients as compared with placebo were analyzed. Included were the primary composite endpoint of percentage patients with ≥2 points reduction in clinical activity score (CAS, seven-point scale) and a reduction of ≥2 mm in proptosis, secondary individual endpoints of proptosis and CAS reduction, GO quality of life questionnaire (GO-QoL) and clinical severity improvement to assess possible relapse.

Thirty-one of 42 (74%) teprotumumab and six of 45 (13%) placebo treated patients with GO reached the primary outcome at treatment week 28 (p<0.001). As much as 93% of teprotumumab treated patients maintained response from end of treatment period (week 24). Proptosis response was similar to the primary outcome, with 55% of teprotumumab patients maintaining a high response (≥3 mm decrease). At week 28, 37/42 (88%) of teprotumumab and 27/45 (60%) of placebo patients reached the CAS outcome (p=0.003). All individual CAS components were also significantly different from placebo (p≤0.04) except eyelid erythema (p=0.06). Severity measures (percentage of patients with chemosis and swelling of eyelid decreased one grade, p=0.11 and p=0.01, respectively. Lid aperture decrease ≥2 mm (p=0.09) favored teprotumumab, though not powered for these severity measures. Overall GO-QoL was significantly higher than placebo in the teprotumumab patients (p<0.001). Thyroid function was stable through the treatment phase and subsequent follow-up in both study groups. Teprotumumab did not affect thyroid-related hormone levels.

These data show that Tepro reduced the composite primary outcome of both CAS and proptosis, as well as the individual measures, i.e., GO-QoL, significantly at seven weeks after treatment discontinuation. This analysis also indicates that proptosis can serve as a primary and sensitive outcome for future clinical trials examining responses to therapy in GO.

Example 14. Teprotumumab (Antibody 1) Treatment Improved Diplopia During Active Treatment and Maintained Significance after Drug Discontinuation in TED Patients The clinical trial of an IGF-1R inhibitor teprotumumab described in Example 1 and the data obtained therefrom (described in the above examples) demonstrates that teprotumumab reduced proptosis and clinical activity score in thyroid eye disease (TED) patients.

Further to those experiments, forty two (42) teprotumumab-treated patients with TED were examined for diplopia severity compared with 45 placebo-treated patients up to 48 weeks after trial completion. Diplopia grades were none, intermittent, inconstant, and constant.

At the end of the controlled trial (week 24) there were significantly more Tepro patients who had improved by ≥1 grade than placebo (62% v 22%, p<0.001), improvement in GO-QoL Visual for those with constant diplopia at baseline versus placebo (p=0.03), reduction in constant diplopia (36% to 9.5%) and increase in those with no diplopia (9.5% to 50%). Grade improvement remained significant out to week 72 of follow-up off drug (50% v 24%, p=0.01).

These data show that Tepro treatment improved diplopia during active treatment and maintained significance after drug discontinuation in TED patients.

Example 15. Results of Follow-Up Treatment with Teprotumumab (Antibody 1)

The following are the data obtained from the follow-up of patients seven weeks after completion of treatment.

TABLE 6

Proportion of Responders by Treatment Group and Visit
Imputation for Subjects Receiving TED During Follow-up
ITT Population - Including Week 24 Responders on Primary Endpoint

| Week Statistics | Placebo (N = 9) | RV 001 (N = 29) |
|---|---|---|
| Week 28 | | |
| Responder [1] | 5 (55.6%) | 27 (93.1%) |
| Non-Responder | 4 (44.4%) | 2 (6.9%) |
| Total | 9 (100%) | 29 (100%) |
| Chi-square Test [2]: | | |
| Difference | | 37.5% |
| 95% CI | | (3.8%, 71.3%) |
| P-value | | 0.007 |
| Week 72 | | |
| Responder [1] | 5 (55.6%) | 15 (51.7%) |
| Non-Responder | 4 (44.4%) | 14 (48.3%) |
| Total | 9 (100%) | 29 (100%) |

TABLE 6-continued

Proportion of Responders by Treatment Group and Visit
Imputation for Subjects Receiving TED During Follow-up
ITT Population - Including Week 24 Responders on Primary Endpoint

| Week Statistics | Placebo (N = 9) | RV 001 (N = 29) |
|---|---|---|
| Chi-square Test [2]: | | |
| Difference | | −3.8% |
| 95% CI | | (−41.0%, 33.4%) |
| P-value | | 0.841 |

Note:
Subjects who received TED treatment in the follow-up were treated as non-responders from the time of TED treatment forward.
[1] Responders are defined as subjects who had a reduction in CAS of >=2 points AND reduction in proptosis of >=2 mm in the study eye and no deterioration (increase in CAS of >=2 points or increase in proptosis of >=2 mm) in the non-study eye.
[2] Chi square test comparing Responder vs. Non-Responder. Difference = responder proportion in RV 001 group − responder proportion in Placebo group.

TABLE 7

Proportion of Responders by Treatment Group and Visit (Study Eye)
Imputation for Subjects Receiving TED During Follow-up
(ITT Population)

| Week Statistics | Placebo (N = 45) | RV 001 (N = 42) |
|---|---|---|
| Week 6 | | |
| Responder [1] | 2 (4.4%) | 18 (42.9%) |
| Non-Responder/Missing | 43 (95.6%) | 24 (57.1%) |
| Total | 45 (100%) | 42 (100%) |
| Chi-square Test [2]: | | |
| Difference | | 38.4% |
| 95% CI | | (22.3%, 54.5%) |
| P-value | | <0.001 |
| Week 12 | | |
| Responder [1] | 2 (4.4%) | 23 (54.8%) |
| Non-Responder/Missing | 43 (95.6%) | 19 (45.2%) |
| Total | 45 (100%) | 42 (100%) |
| Chi-square Test [2]: | | |
| Difference | | 50.3% |
| 95% CI | | (34.1%, 66.5%) |
| P-value | | <0.001 |
| Week 18 | | |
| Responder [1] | 2 (4.4%) | 30 (71.4%) |
| Non-Responder/Missing | 43 (95.6%) | 12 (28.6%) |
| Total | 45 (100%) | 42 (100%) |
| Chi-square Test [2]: | | |
| Difference | | 67.0% |
| 95% CI | | (52.1%, 81.9%) |
| P-value | | <0.001 |
| Week 24 | | |
| Responder [1] | 9 (20.0%) | 29 (69.0%) |
| Non-Responder/Missing | 36 (80.0%) | 13 (31.0%) |
| Total | 45 (100%) | 42 (100%) |
| Chi-square Test [2]: | | |
| Difference | | 49.0% |
| 95% CI | | (30.8%, 67.3%) |
| P-value | | <0.001 |

TABLE 7-continued

Proportion of Responders by Treatment Group and Visit (Study Eye) Imputation for Subjects Receiving TED During Follow-up (ITT Population)

| Week Statistics | Placebo (N = 45) | RV 001 (N = 42) |
|---|---|---|
| Week 28 | | |
| Responder [1] | 6 (13.3%) | 31 (73.8%) |
| Non-Responder/Missing | 39 (86.7%) | 11 (26.2%) |
| Total | 45 (100%) | 42 (100%) |
| Chi-square Test [2]: | | |
| Difference | | 60.5% |
| 95% CI | | (43.9%, 77.1%) |
| P-value | | <0.001 |
| Week 72 | | |
| Responder [1] | 10 (22.2%) | 19 (45.2%) |
| Non-Responder/Missing | 35 (77.8%) | 23 (54.8%) |
| Total | 45 (100%) | 42 (100%) |
| Chi-square Test [2]: | | |
| Difference | | 23.0% |
| 95% CI | | (3.7%, 42.4%) |
| P-value | | 0.023 |

Note:
Subjects who received TED treatment in the follow-up were treated as non-responders from the time of TED treatment forward.
[1] Responders are defined as subjects who had a reduction in CAS of >=2 points AND reduction in proptosis of >=2 mm in the study eye and no deterioration (increase in CAS of >=2 points or increase in proptosis of >=2 mm) in the non-study eye.
[2] Chi square test comparing Responder vs. Non-Responder. Difference = responder proportion in RV 001 group − responder proportion in Placebo group.

TABLE 8

Proportion of Proptosis Response by Treatment Group and Visit - Responder versus Other Imputation for Subjects Receiving TED During Follow-up (ITT Population)

| Eye Week Statistics | Placebo (N = 45) | RV 001 (N = 42) |
|---|---|---|
| Study Eye | | |
| Week 6 | | |
| Responder [1] | 4 (8.9%) | 22 (52.4%) |
| Other | 41 (91.1%) | 20 (47.6%) |
| Chi-square Test [2]: | | |
| Difference | | 43.5% |
| 95% CI | | (26.3%, 60.7%) |
| P-value | | <0.001 |
| Week 12 | | |
| Responder [1] | 2 (4.4%) | 24 (57.1%) |
| Other | 43 (95.6%) | 18 (42.9%) |
| Chi-square Test [2]: | | |
| Difference | | 52.7% |
| 95% CI | | (36.6%, 68.8%) |
| P-value | | <0.001 |
| Week 18 | | |
| Responder [1] | 4 (8.9%) | 32 (76.2%) |
| Other | 41 (91.1%) | 10 (23.8%) |
| Chi-square Test [2]: | | |
| Difference | | 67.3% |
| 95% CI | | (52.0%, 82.6%) |
| P-value | | <0.001 |
| Week 24 | | |
| Responder [1] | 9 (20.0%) | 30 (71.4%) |
| Other | 36 (80.0%) | 12 (28.6%) |
| Chi-square Test [2]: | | |
| Difference | | 51.4% |
| 95% CI | | (33.4%, 69.4%) |
| P-value | | <0.001 |
| Week 28 | | |
| Responder [1] | 6 (13.3%) | 31 (73.8%) |
| Other | 39 (86.7%) | 11 (26.2%) |
| Chi-square Test [2]: | | |
| Difference | | 60.5% |
| 95% CI | | (43.9%, 77.1%) |
| P-value | | <0.001 |
| Week 72 | | |
| Responder [1] | 10 (22.2%) | 19 (45.2%) |
| Other | 35 (77.8%) | 23 (54.8%) |
| Chi-square Test [2]: | | |
| Difference | | 23.0% |
| 95% CI | | (3.7%, 42.4%) |
| P-value | | 0.023 |
| Non-Study Eye | | |
| Week 6 | | |
| Responder [1] | 3 (6.7%) | 9 (21.4%) |
| Other | 42 (93.3%) | 33 (78.6%) |
| Chi-square Test [2]: | | |
| Difference | | 14.8% |
| 95% CI | | (0.4%, 29.2%) |
| P-value | | 0.046 |
| Week 12 | | |
| Responder [1] | 3 (6.7%) | 15 (35.7%) |
| Other | 42 (93.3%) | 27 (64.3%) |
| Chi-square Test [2]: | | |
| Difference | | 29.0% |
| 95% CI | | (12.8%, 45.3%) |
| P-value | | 0.001 |
| Week 18 | | |
| Responder [1] | 4 (8.9%) | 21 (50.0%) |
| Other | 41 (91.1%) | 21 (50.0%) |
| Chi-square Test [2]: | | |
| Difference | | 41.1% |
| 95% CI | | (23.9%, 58.4%) |
| P-value | | <0.001 |
| Week 24 | | |
| Responder [1] | 6 (13.3%) | 26 (61.9%) |
| Other | 39 (86.7%) | 16 (38.1%) |
| Chi-square Test [2]: | | |
| Difference | | 48.6% |
| 95% CI | | (30.8%, 66.3%) |
| P-value | | <0.001 |
| Week 28 | | |
| Responder [1] | 5 (11.1%) | 23 (54.8%) |
| Other | 40 (88.9%) | 19 (45.2%) |

TABLE 8-continued

Proportion of Proptosis Response by Treatment Group and Visit - Responder versus Other Imputation for Subjects Receiving TED During Follow-up (ITT Population)

| Eye Week Statistics | Placebo (N = 45) | RV 001 (N = 42) |
|---|---|---|
| Chi-square Test [2]: | | |
| Difference | | 43.7% |
| 95% CI | | (26.0%, 61.3%) |
| P-value | | <0.001 |
| Week 72 | | |
| Responder [1] | 7 (15.6%) | 13 (31.0%) |
| Other | 38 (84.4%) | 29 (69.0%) |
| Chi-square Test [2]: | | |
| Difference | | 15.4% |
| 95% CI | | (−2.1%, 32.9%) |
| P-value | | 0.088 |

Note:
Subjects who received TED treatment in the follow-up were treated as non-responders from the time of TED treatment forward.
[1] Responder is defined as a reduction in proptosis of >=2 mm from baseline.
[2] Chi square test comparing Responder vs. Other (Stable, Worsening, or Missing/Drop Out). Difference = responder proportion in RV 001 group − responder proportion in Placebo group.

TABLE 9

Proportion of CAS Response by Treatment Group and Visit - Responder versus Other Imputation for Subjects Receiving TED During Follow-up (ITT Population)

| Eye Week Statistics | Placebo (N = 45) | RV 001 (N = 42) |
|---|---|---|
| Study Eye Week 6 | | |
| Responder [1] | 13 (28.9%) | 33 (78.6%) |
| Other | 32 (71.1%) | 9 (21.4%) |
| Chi-square Test [2]: | | |
| Difference | | 49.7% |
| 95% CI | | (31.5%, 67.8%) |
| P-value | | <0.001 |
| Week 12 | | |
| Responder [1] | 26 (57.8%) | 38 (90.5%) |
| Other | 19 (42.2%) | 4 (9.5%) |
| Chi-square Test [2]: | | |
| Difference | | 32.7% |
| 95% CI | | (15.8%, 49.6%) |
| P-value | | 0.001 |
| Week 18 | | |
| Responder [1] | 26 (57.8%) | 36 (85.7%) |
| Other | 19 (42.2%) | 6 (14.3%) |
| Chi-square Test [2]: | | |
| Difference | | 27.9% |
| 95% CI | | (10.0%, 45.8%) |
| P-value | | 0.004 |
| Week 24 | | |
| Responder [1] | 28 (62.2%) | 37 (88.1%) |
| Other | 17 (37.8%) | 5 (11.9%) |
| Chi-square Test [2]: | | |
| Difference | | 25.9% |
| 95% CI | | (8.7%, 43.1%) |
| P-value | | 0.006 |

TABLE 9-continued

Proportion of CAS Response by Treatment Group and Visit - Responder versus Other Imputation for Subjects Receiving TED During Follow-up (ITT Population)

| Eye Week Statistics | Placebo (N = 45) | RV 001 (N = 42) |
|---|---|---|
| Week 28 | | |
| Responder [1] | 27 (60.0%) | 37 (88.1%) |
| Other | 18 (40.0%) | 5 (11.9%) |
| Chi-square Test [2]: | | |
| Difference | | 28.1% |
| 95% CI | | (10.8%, 45.4%) |
| P-value | | 0.003 |
| Week 72 | | |
| Responder [1] | 31 (68.9%) | 29 (69.0%) |
| Other | 14 (31.1%) | 13 (31.0%) |
| Chi-square Test [2]: | | |
| Difference | | 0.2% |
| 95% CI | | (−19.3%, 19.6%) |
| P-value | | 0.987 |
| Non-Study Eye Week 6 | | |
| Responder [1] | 14 (31.1%) | 29 (69.0%) |
| Other | 31 (68.9%) | 13 (31.0%) |
| Chi-square Test [2]: | | |
| Difference | | 37.9% |
| 95% CI | | (18.5%, 57.4%) |
| P-value | | <0.001 |
| Week 12 | | |
| Responder [1] | 18 (40.0%) | 32 (76.2%) |
| Other | 27 (60.0%) | 10 (23.8%) |
| Chi-square Test [2]: | | |
| Difference | | 36.2% |
| 95% CI | | (16.9%, 55.4%) |
| P-value | | 0.001 |
| Week 18 | | |
| Responder [1] | 23 (51.1%) | 31 (73.8%) |
| Other | 22 (48.9%) | 11 (26.2%) |
| Chi-square Test [2]: | | |
| Difference | | 22.7% |
| 95% CI | | (2.9%, 42.4%) |
| P-value | | 0.029 |
| Week 24 | | |
| Responder [1] | 22 (48.9%) | 32 (76.2%) |
| Other | 23 (51.1%) | 10 (23.8%) |
| Chi-square Test [2]: | | |
| Difference | | 27.3% |
| 95% CI | | (7.8%, 46.8%) |
| P-value | | 0.009 |
| Week 28 | | |
| Responder [1] | 20 (44.4%) | 32 (76.2%) |
| Other | 25 (55.6%) | 10 (23.8%) |

TABLE 9-continued

Proportion of CAS Response by Treatment Group and Visit - Responder versus Other Imputation for Subjects Receiving TED During Follow-up (ITT Population)

| Eye<br>Week<br>Statistics | Placebo<br>(N = 45) | RV 001<br>(N = 42) |
|---|---|---|
| Chi-square Test [2]: | | |
| Difference | | 31.7% |
| 95% CI | | (12.3%, 51.2%) |
| P-value | | 0.003 |
| Week 72 | | |
| Responder [1] | 26 (57.8%) | 26 (61.9%) |
| Other | 19 (42.2%) | 16 (38.1%) |
| Chi-square Test [2]: | | |
| Difference | | 4.1% |
| 95% CI | | (−16.5%, 24.7%) |
| P-value | | 0.695 |

Abbreviation:
CAS = Clinical Activity Score (7 point scale).
Note:
Subjects who received TED treatment in the follow-up were treated as non-responders from the time of TED treatment forward.
[1] Responder is defined as decrease of 2 points or more from baseline.
[2] Chi square test comparing Responder vs. Other (Stable, Worsening, or Missing/Drop Out). Difference = responder proportion in RV 001 group − responder proportion in Placebo group.

TABLE 10

Summary of Individual CAS Component by Treatment (ITT Population)

| Percent of Subjects with Symptom | Placebo<br>N = 45 | RV 001<br>N = 42 |
|---|---|---|
| SPONTANEOUS ORBITAL PAIN | | |
| BASELINE | 31/45 (68.89%) | 31/42 (73.81%) |
| P-value (Chi-squared with correction) | | 0.78735 |
| P-value (Chi-squared w/o correction) | | 0.61229 |
| P-value (Fisher Exact) | | 0.64307 |
| Week 6 | 19/42 (45.24%) | 15/41 (36.59%) |
| P-value (Chi-squared with correction) | | 0.56312 |
| P-value (Chi-squared w/o correction) | | 0.42288 |
| P-value (Fisher Exact) | | 0.50517 |
| Week 12 | 15/41 (36.59%) | 5/40 (12.5%) |
| P-value (Chi-squared with correction) | | 0.02410 |
| P-value (Chi-squared w/o correction) | | 0.01196 |
| P-value (Fisher Exact) | | 0.01925 |
| Week 18 | 17/41 (41.46%) | 3/39 (7.69%) |
| P-value (Chi-squared with correction) | | 0.00124 |
| P-value (Chi-squared w/o correction) | | 0.00049 |
| P-value (Fisher Exact) | | 0.00061 |
| Week 24 | 8/39 (20.51%) | 2/38 (5.26%) |
| P-value (Chi-squared with correction) | | 0.09871 |
| P-value (Chi-squared w/o correction) | | 0.04657 |
| P-value (Fisher Exact) | | 0.08661 |
| Week 28 | 11/37 (29.73%) | 2/37 (5.41%) |
| P-value (Chi-squared with correction) | | 0.01453 |
| P-value (Chi-squared w/o correction) | | 0.00597 |
| P-value (Fisher Exact) | | 0.01226 |
| Week 72 | 5/32 (15.62%) | 7/33 (21.21%) |
| P-value (Chi-squared with correction) | | 0.79432 |
| P-value (Chi-squared w/o correction) | | 0.56163 |
| P-value (Fisher Exact) | | 0.75082 |
| GAZE EVOKED ORBITAL PAIN | | |
| BASELINE | 35/45 (77.78%) | 32/42 (76.19%) |
| P-value (Chi-squared with correction) | | 1.00000 |
| P-value (Chi-squared w/o correction) | | 0.86043 |
| P-value (Fisher Exact) | | 1.00000 |
| Week 6 | 22/42 (52.38%) | 15/41 (36.59%) |
| P-value (Chi-squared with correction) | | 0.21996 |
| P-value (Chi-squared w/o correction) | | 0.14776 |
| P-value (Fisher Exact) | | 0.18697 |
| Week 12 | 14/41 (34.15%) | 8/40 (20%) |
| P-value (Chi-squared with correction) | | 0.23749 |
| P-value (Chi-squared w/o correction) | | 0.15240 |
| P-value (Fisher Exact) | | 0.21224 |
| Week 18 | 14/41 (34.15%) | 6/39 (15.38%) |
| P-value (Chi-squared with correction) | | 0.09319 |
| P-value (Chi-squared w/o correction) | | 0.05273 |
| P-value (Fisher Exact) | | 0.07145 |

TABLE 10-continued

Summary of Individual CAS Component by Treatment (ITT Population)

| Percent of Subjects with Symptom | Placebo N = 45 | RV 001 N = 42 |
|---|---|---|
| Week 24 | 14/39 (35.9%) | 4/38 (10.53%) |
| P-value (Chi-squared with correction) | | 0.01824 |
| P-value (Chi-squared w/o correction) | | 0.00854 |
| P-value (Fisher Exact) | | 0.01412 |
| Week 28 | 14/37 (37.84%) | 4/37 (10.81%) |
| P-value (Chi-squared with correction) | | 0.01475 |
| P-value (Chi-squared w/o correction) | | 0.00674 |
| P-value (Fisher Exact) | | 0.01336 |
| Week 72 | 6/32 (18.75%) | 3/33 (9.09%) |
| P-value (Chi-squared with correction) | | 0.44245 |
| P-value (Chi-squared w/o correction) | | 0.25965 |
| P-value (Fisher Exact) | | 0.30339 |
| EYELID SWELLING | | |
| BASELINE | 45/45 (100%) | 40/42 (95.24%) |
| P-value (Chi-squared with correction) | | 0.44417 |
| P-value (Chi-squared w/o correction) | | 0.13861 |
| P-value (Fisher Exact) | | 0.23015 |
| Week 6 | 37/42 (88.1%) | 26/41 (63.41%) |
| P-value (Chi-squared with correction) | | 0.01770 |
| P-value (Chi-squared w/o correction) | | 0.00857 |
| P-value (Fisher Exact) | | 0.01067 |
| Week 12 | 33/41 (80.49%) | 21/40 (52.5%) |
| P-value (Chi-squared with correction) | | 0.01486 |
| P-value (Chi-squared w/o correction) | | 0.00755 |
| P-value (Fisher Exact) | | 0.00978 |
| Week 18 | 33/41 (80.49%) | 17/39 (43.59%) |
| P-value (Chi-squared with correction) | | 0.00149 |
| P-value (Chi-squared w/o correction) | | 0.00066 |
| P-value (Fisher Exact) | | 0.00107 |
| Week 24 | 27/39 (69.23%) | 11/38 (28.95%) |
| P-value (Chi-squared with correction) | | 0.00094 |
| P-value (Chi-squared w/o correction) | | 0.00041 |
| P-value (Fisher Exact) | | 0.00059 |
| Week 28 | 27/37 (72.97%) | 9/37 (24.32%) |
| P-value (Chi-squared with correction) | | 0.00008 |
| P-value (Chi-squared w/o correction) | | 0.00003 |
| P-value (Fisher Exact) | | 0.00006 |
| Week 72 | 16/32 (50%) | 9/33 (27.27%) |
| P-value (Chi-squared with correction) | | 0.10353 |
| P-value (Chi-squared w/o correction) | | 0.05971 |
| P-value (Fisher Exact) | | 0.07692 |
| EYELID ERYTHEMA | | |
| BASELINE | 27/45 (60%) | 17/42 (40.48%) |
| P-value (Chi-squared with correction) | | 0.10838 |
| P-value (Chi-squared w/o correction) | | 0.06874 |
| P-value (Fisher Exact) | | 0.08744 |
| Week 6 | 20/42 (47.62%) | 8/41 (19.51%) |
| P-value (Chi-squared with correction) | | 0.01330 |
| P-value (Chi-squared w/o correction) | | 0.00677 |
| P-value (Fisher Exact) | | 0.01024 |
| Week 12 | 12/41 (29.27%) | 4/40 (10%) |
| P-value (Chi-squared with correction) | | 0.05762 |
| P-value (Chi-squared w/o correction) | | 0.02943 |
| P-value (Fisher Exact) | | 0.04884 |
| Week 18 | 12/41 (29.27%) | 3/39 (7.69%) |
| P-value (Chi-squared with correction) | | 0.02890 |
| P-value (Chi-squared w/o correction) | | 0.01346 |
| P-value (Fisher Exact) | | 0.02045 |
| Week 24 | 10/39 (25.64%) | 2/38 (5.26%) |
| P-value (Chi-squared with correction) | | 0.03151 |
| P-value (Chi-squared w/o correction) | | 0.01371 |
| P-value (Fisher Exact) | | 0.02488 |
| Week 28 | 7/37 (18.92%) | 1/37 (2.7%) |
| P-value (Chi-squared with correction) | | 0.06123 |
| P-value (Chi-squared w/o correction) | | 0.02469 |
| P-value (Fisher Exact) | | 0.05567 |
| Week 72 | 2/32 (6.25%) | 2/33 (6.06%) |
| P-value (Chi-squared with correction) | | 1.00000 |
| P-value (Chi-squared w/o correction) | | 0.97466 |
| P-value (Fisher Exact) | | 1.00000 |

TABLE 10-continued

Summary of Individual CAS Component by Treatment (ITT Population)

| Percent of Subjects with Symptom | Placebo N = 45 | RV 001 N = 42 |
|---|---|---|
| CONJUNCTIVAL REDNESS | | |
| BASELINE | 42/45 (93.33%) | 40/42 (95.24%) |
| P-value (Chi-squared with correction) | | 1.00000 |
| P-value (Chi-squared w/o correction) | | 0.70287 |
| P-value (Fisher Exact) | | 1.00000 |
| Week 6 | 33/42 (78.57%) | 21/41 (51.22%) |
| P-value (Chi-squared with correction) | | 0.01718 |
| P-value (Chi-squared w/o correction) | | 0.00897 |
| P-value (Fisher Exact) | | 0.01163 |
| Week 12 | 30/41 (73.17%) | 17/40 (42.5%) |
| P-value (Chi-squared with correction) | | 0.01013 |
| P-value (Chi-squared w/o correction) | | 0.00517 |
| P-value (Fisher Exact) | | 0.00698 |
| Week 18 | 21/41 (51.22%) | 13/39 (33.33%) |
| P-value (Chi-squared with correction) | | 0.16412 |
| P-value (Chi-squared w/o correction) | | 0.10575 |
| P-value (Fisher Exact) | | 0.11939 |
| Week 24 | 19/39 (48.72%) | 12/38 (31.58%) |
| P-value (Chi-squared with correction) | | 0.19333 |
| P-value (Chi-squared w/o correction) | | 0.12523 |
| P-value (Fisher Exact) | | 0.16461 |
| Week 28 | 17/37 (45.95%) | 7/37 (18.92%) |
| P-value (Chi-squared with correction) | | 0.02542 |
| P-value (Chi-squared w/o correction) | | 0.01302 |
| P-value (Fisher Exact) | | 0.02438 |
| Week 72 | 9/32 (28.12%) | 13/33 (39.39%) |
| P-value (Chi-squared with correction) | | 0.48534 |
| P-value (Chi-squared w/o correction) | | 0.33711 |
| P-value (Fisher Exact) | | 0.43386 |
| CHEMOSIS | | |
| BASELINE | 30/45 (66.67%) | 25/42 (59.52%) |
| P-value (Chi-squared with correction) | | 0.63982 |
| P-value (Chi-squared w/o correction) | | 0.48994 |
| P-value (Fisher Exact) | | 0.51306 |
| Week 6 | 25/42 (59.52%) | 9/41 (21.95%) |
| P-value (Chi-squared with correction) | | 0.00113 |
| P-value (Chi-squared w/o correction) | | 0.00050 |
| P-value (Fisher Exact) | | 0.00074 |
| Week 12 | 18/41 (43.9%) | 6/40 (15%) |
| P-value (Chi-squared with correction) | | 0.00919 |
| P-value (Chi-squared w/o correction) | | 0.00440 |
| P-value (Fisher Exact) | | 0.00689 |
| Week 18 | 17/41 (41.46%) | 4/39 (10.26%) |
| P-value (Chi-squared with correction) | | 0.00354 |
| P-value (Chi-squared w/o correction) | | 0.00152 |
| P-value (Fisher Exact) | | 0.00202 |
| Week 24 | 13/39 (33.33%) | 3/38 (7.89%) |
| P-value (Chi-squared with correction) | | 0.01352 |
| P-value (Chi-squared w/o correction) | | 0.00595 |
| P-value (Fisher Exact) | | 0.01005 |
| Week 28 | 13/37 (35.14%) | 3/37 (8.11%) |
| P-value (Chi-squared with correction) | | 0.01104 |
| P-value (Chi-squared w/o correction) | | 0.00475 |
| P-value (Fisher Exact) | | 0.00955 |
| Week 72 | 4/32 (12.5%) | 4/33 (12.12%) |
| P-value (Chi-squared with correction) | | 1.00000 |
| P-value (Chi-squared w/o correction) | | 0.96293 |
| P-value (Fisher Exact) | | 1.00000 |
| INFLAMMATION OF CARUNCLE OR PLICA | | |
| BASELINE | 26/45 (57.78%) | 28/42 (66.67%) |
| P-value (Chi-squared with correction) | | 0.52689 |
| P-value (Chi-squared w/o correction) | | 0.39319 |
| P-value (Fisher Exact) | | 0.50771 |
| Week 6 | 20/42 (47.62%) | 11/41 (26.83%) |
| P-value (Chi-squared with correction) | | 0.08351 |
| P-value (Chi-squared w/o correction) | | 0.05028 |
| P-value (Fisher Exact) | | 0.06967 |
| Week 12 | 18/41 (43.9%) | 8/40 (20%) |
| P-value (Chi-squared with correction) | | 0.03885 |
| P-value (Chi-squared w/o correction) | | 0.02124 |
| P-value (Fisher Exact) | | 0.03167 |
| Week 18 | 14/41 (34.15%) | 8/39 (20.51%) |

TABLE 10-continued

Summary of Individual CAS Component by Treatment (ITT Population)

| Percent of Subjects with Symptom | Placebo N = 45 | RV 001 N = 42 |
|---|---|---|
| P-value (Chi-squared with correction) | | 0.26503 |
| P-value (Chi-squared w/o correction) | | 0.17223 |
| P-value (Fisher Exact) | | 0.21440 |
| Week 24 | 12/39 (30.77%) | 5/38 (13.16%) |
| P-value (Chi-squared with correction) | | 0.11229 |
| P-value (Chi-squared w/o correction) | | 0.06249 |
| P-value (Fisher Exact) | | 0.09814 |
| Week 28 | 11/37 (29.73%) | 3/37 (8.11%) |
| P-value (Chi-squared with correction) | | 0.03774 |
| P-value (Chi-squared w/o correction) | | 0.01757 |
| P-value (Fisher Exact) | | 0.03515 |
| Week 72 | 5/32 (15.62%) | 2/33 (6.06%) |
| P-value (Chi-squared with correction) | | 0.39898 |
| P-value (Chi-squared w/o correction) | | 0.21364 |
| P-value (Fisher Exact) | | 0.25756 |

Note:
Subjects who received TED treatment in the follow-up were removed from summary statistics from the time of TED treatment forward.

TABLE 11

Individual CSS by Treatment Group and Visit - Lid Aperture (mm) Imputation for Subjects Receiving TED During Follow-up (ITT Population)

| | Placebo | RV 001 |
|---|---|---|
| Study Eye | 45 | 42 |
| BASELINE | | |
| n | 45 | 42 |
| Mean (SD) | 11.13 (1.832) | 11.79 (2.618) |
| Median | 11 | 11 |
| Q1, Q3 | 10.00, 12.00 | 10.00, 13.00 |
| Min, Max | 6.00, 15.00 | 8.00, 19.00 |
| WEEK 6 | | |
| n | 42 | 39 |
| Mean (SD) | 10.99 (1.930) | 11.59 (1.929) |
| Median | 11 | 11 |
| Q1, Q3 | 10.00, 12.00 | 10.00, 13.00 |
| Min, Max | 7.00, 16.00 | 8.00, 16.00 |
| CSS responder | 7 (15.6%) | 9 (21.4%) |
| CSS non-responder | 35 (77.8%) | 30 (71.4%) |
| Missing | 3 (6.7%) | 3 (7.1%) |
| Missing as non-responder | 38 (84.4%) | 33 (78.6%) |
| P-value Responder vs. non-responder | | 0.469 |
| P-value Responder vs. non-responder/Missing | | 0.4798 |
| WEEK 12 | | |
| n | 41 | 39 |
| Mean (SD) | 10.89 (1.679) | 11.32 (1.921) |
| Median | 11 | 11 |
| Q1, Q3 | 10.00, 12.00 | 10.00, 12.00 |
| Min, Max | 7.00, 15.00 | 8.00, 16.00 |
| CSS responder | 2 (4.4%) | 11 (26.2%) |
| CSS non-responder | 39 (86.7%) | 28 (66.7%) |
| Missing | 4 (8.9%) | 3 (7.1%) |
| Missing as non-responder | 43 (95.6%) | 31 (73.8%) |
| P-value Responder vs. non-responder | | 0.0047 |
| P-value Responder vs. non-responder/Missing | | 0.0045 |
| WEEK 18 | | |
| n | 41 | 39 |
| Mean (SD) | 10.80 (2.185) | 11.33 (1.733) |
| Median | 11 | 11 |
| Q1, Q3 | 9.50, 12.00 | 10.00, 12.00 |
| Min, Max | 4.50, 17.00 | 8.00, 16.00 |
| CSS responder | 6 (13.3%) | 10 (23.8%) |
| CSS non-responder | 35 (77.8%) | 29 (69.0%) |
| Missing | 4 (8.9%) | 3 (7.1%) |
| Missing as non-responder | 39 (86.7%) | 32 (76.2%) |
| P-value Responder vs. non-responder | | 0.2186 |
| P-value Responder vs. non-responder/Missing | | 0.2075 |
| WEEK 24 | | |
| n | 39 | 38 |
| Mean (SD) | 10.82 (2.293) | 11.32 (1.940) |
| Median | 11 | 11 |
| Q1, Q3 | 9.50, 12.00 | 10.00, 12.00 |
| Min, Max | 5.00, 17.00 | 8.00, 16.00 |
| CSS responder | 5 (11.1%) | 11 (26.2%) |
| CSS non-responder | 34 (75.6%) | 27 (64.3%) |
| Missing | 6 (13.3%) | 4 (9.5%) |
| Missing as non-responder | 40 (88.9%) | 31 (73.8%) |
| P-value Responder vs. non-responder | | 0.0812 |
| P-value Responder vs. non-responder/Missing | | 0.0696 |
| WEEK 28 | | |
| n | 36 | 36 |
| Mean (SD) | 11.06 (1.941) | 11.29 (1.987) |
| Median | 11 | 11 |
| Q1, Q3 | 10.00, 12.00 | 10.00, 12.00 |
| Min, Max | 6.50, 17.00 | 8.00, 15.00 |
| CSS responder | 7 (15.6%) | 13 (31.0%) |
| CSS non-responder | 31 (68.9%) | 23 (54.8%) |
| Missing | 7 (15.6%) | 6 (14.3%) |
| Missing as non-responder | 38 (84.4%) | 29 (69.0%) |
| P-value Responder vs. non-responder | | 0.0868 |
| P-value Responder vs. non-responder/Missing | | 0.0881 |
| WEEK 72 | | |
| n | 32 | 33 |
| Mean (SD) | 10.31 (1.759) | 11.39 (1.758) |
| Median | 10 | 11.5 |
| Q1, Q3 | 9.00, 12.00 | 10.00, 12.00 |
| Min, Max | 6.50, 14.00 | 9.00, 16.00 |
| CSS responder | 5 (11.1%) | 12 (28.6%) |
| CSS non-responder | 33 (73.3%) | 25 (59.5%) |

TABLE 11-continued

Individual CSS by Treatment Group and Visit - Lid Aperture (mm)
Imputation for Subjects Receiving TED During Follow-up
(ITT Population)

|  | Placebo | RV 001 |
|---|---|---|
| Missing | 7 (15.6%) | 5 (11.9%) |
| Missing as non-responder | 40 (88.9%) | 30 (71.4%) |
| P-value Responder vs. non-responder |  | 0.0462 |
| P-value Responder vs. non-responder/Missing |  | 0.0401 |
| Non-study Eye | 45 | 42 |
| BASELINE |  |  |
| n | 45 | 42 |
| Mean (SD) | 10.42 (1.481) | 10.87 (2.387) |
| Median | 10 | 10 |
| Q1, Q3 | 10.00, 11.00 | 9.00, 12.00 |
| Min, Max | 7.00, 15.00 | 8.00, 19.00 |
| WEEK 6 |  |  |
| n | 42 | 39 |
| Mean (SD) | 10.45 (1.521) | 10.74 (1.870) |
| Median | 10 | 11 |
| Q1, Q3 | 9.00, 11.00 | 9.00, 12.00 |
| Min, Max | 8.00, 15.00 | 8.00, 15.00 |
| CSS responder | 4 (8.9%) | 4 (9.5%) |
| CSS non-responder | 38 (84.4%) | 35 (83.3%) |
| Missing | 3 (6.7%) | 3 (7.1%) |
| Missing as non-responder | 41 (91.1%) | 38 (90.5%) |
| P-value Responder vs. non-responder |  | 0.9121 |
| P-value Responder vs. non-responder/Missing |  | 0.9184 |
| WEEK 12 |  |  |
| n | 41 | 39 |
| Mean (SD) | 10.16 (1.489) | 10.90 (2.159) |
| Median | 10 | 11 |
| Q1, Q3 | 9.00, 11.00 | 9.00, 12.00 |
| Min, Max | 7.00, 15.00 | 8.00, 17.50 |
| CSS responder | 6 (13.3%) | 5 (11.9%) |
| CSS non-responder | 35 (77.8%) | 34 (81.0%) |
| Missing | 4 (8.9%) | 3 (7.1%) |
| Missing as non-responder | 39 (86.7%) | 37 (88.1%) |
| P-value Responder vs. non-responder |  | 0.8139 |
| P-value Responder vs. non-responder/Missing |  | 0.8412 |
| WEEK 18 |  |  |
| n | 41 | 39 |
| Mean (SD) | 10.12 (1.836) | 10.92 (2.047) |
| Median | 10 | 11 |
| Q1, Q3 | 9.00, 11.00 | 9.00, 12.00 |
| Min, Max | 4.50, 15.00 | 8.00, 16.00 |
| CSS responder | 7 (15.6%) | 6 (14.3%) |
| CSS non-responder | 34 (75.6%) | 33 (78.6%) |
| Missing | 4 (8.9%) | 3 (7.1%) |
| Missing as non-responder | 38 (84.4%) | 36 (85.7%) |
| P-value Responder vs. non-responder |  | 0.8379 |
| P-value Responder vs. non-responder/Missing |  | 0.8681 |
| WEEK 24 |  |  |
| n | 39 | 38 |
| Mean (SD) | 10.18 (2.024) | 10.84 (2.096) |
| Median | 10 | 11 |
| Q1, Q3 | 9.00, 11.00 | 9.00, 12.00 |
| Min, Max | 3.00, 15.00 | 7.00, 15.00 |
| CSS responder | 4 (8.9%) | 7 (16.7%) |
| CSS non-responder | 35 (77.8%) | 31 (73.8%) |
| Missing | 6 (13.3%) | 4 (9.5%) |
| Missing as non-responder | 41 (91.1%) | 35 (83.3%) |
| P-value Responder vs. non-responder |  | 0.306 |
| P-value Responder vs. non-responder/Missing |  | 0.2754 |
| WEEK 28 |  |  |
| n | 36 | 36 |
| Mean (SD) | 10.26 (1.701) | 11.07 (2.122) |
| Median | 10 | 11 |
| Q1, Q3 | 9.00, 11.00 | 9.25, 12.00 |
| Min, Max | 8.00, 15.00 | 8.00, 16.00 |
| CSS responder | 6 (13.3%) | 6 (14.3%) |
| CSS non-responder | 32 (71.1%) | 30 (71.4%) |
| Missing | 7 (15.6%) | 6 (14.3%) |
| Missing as non-responder | 39 (86.7%) | 36 (85.7%) |
| P-value Responder vs. non-responder |  | 0.9185 |
| P-value Responder vs. non-responder/Missing |  | 0.8976 |
| WEEK 72 |  |  |
| n | 32 | 33 |
| Mean (SD) | 10.03 (1.502) | 10.95 (1.800) |
| Median | 10 | 11 |
| Q1, Q3 | 9.00, 11.00 | 10.00, 11.50 |
| Min, Max | 8.00, 14.00 | 8.50, 15.00 |
| CSS responder | 6 (13.3%) | 5 (11.9%) |
| CSS non-responder | 32 (71.1%) | 32 (76.2%) |
| Missing | 7 (15.6%) | 5 (11.9%) |
| Missing as non-responder | 39 (86.7%) | 37 (88.1%) |
| P-value Responder vs. non-responder |  | 0.7806 |
| P-value Responder vs. non-responder/Missing |  | 0.8412 |

Note:
Subjects who received TED treatment in the follow-up were removed from summary statistics from the time of TED treatment forward and were analyzed as non-responders.
CSS responders are defined as subjects who experienced a decrease of >=2 mm from baseline.
The p-values are from Chi square tests without continuity correction.

TABLE 12

Individual CSS by Treatment Group and Visit - Swelling of the Eyelids
Imputation for Subjects Receiving TED During Follow-up
(ITT Population)

|  | Placebo | RV 001 |
|---|---|---|
| Study Eye | 45 | 42 |
| BASELINE |  |  |
| ABSENT | 0 (0.0%) | 2 (4.8%) |
| MILD | 14 (31.1%) | 16 (38.1%) |
| MODERATE | 26 (57.8%) | 24 (57.1%) |
| SEVERE | 5 (11.1%) | 0 (0.0%) |
| Missing | 0 (0.0%) | 0 (0.0%) |
| WEEK 6 |  |  |
| ABSENT | 4 (8.9%) | 10 (23.8%) |
| MILD | 16 (35.6%) | 24 (57.1%) |
| MODERATE | 17 (37.8%) | 6 (14.3%) |
| SEVERE | 5 (11.1%) | 0 (0.0%) |
| Missing | 3 (6.7%) | 2 (4.8%) |
| CSS responder | 11 (24.4%) | 22 (52.4%) |
| CSS non-responder | 31 (68.9%) | 18 (42.9%) |
| Missing | 3 (6.7%) | 2 (4.8%) |
| Missing as non-responder | 34 (75.6%) | 20 (47.6%) |
| P-value Responder vs. non-responder |  | 0.0078 |
| P-value Responder vs. non-responder/Missing |  | 0.0073 |
| WEEK 12 |  |  |
| ABSENT | 6 (13.3%) | 17 (40.5%) |
| MILD | 14 (31.1%) | 19 (45.2%) |
| MODERATE | 17 (37.8%) | 4 (9.5%) |

TABLE 12-continued

Individual CSS by Treatment Group and Visit - Swelling of the Eyelids Imputation for Subjects Receiving TED During Follow-up (ITT Population)

| | Placebo | RV 001 |
|---|---|---|
| SEVERE | 4 (8.9%) | 0 (0.0%) |
| Missing | 4 (8.9%) | 2 (4.8%) |
| CSS responder | 15 (33.3%) | 26 (61.9%) |
| CSS non-responder | 26 (57.8%) | 14 (33.3%) |
| Missing | 4 (8.9%) | 2 (4.8%) |
| Missing as non-responder | 30 (66.7%) | 16 (38.1%) |
| P-value Responder vs. non-responder | | 0.0105 |
| P-value Responder vs. non-responder/Missing | | 0.0076 |
| WEEK 18 | | |
| ABSENT | 6 (13.3%) | 19 (45.2%) |
| MILD | 17 (37.8%) | 19 (45.2%) |
| MODERATE | 15 (33.3%) | 0 (0.0%) |
| SEVERE | 3 (6.7%) | 1 (2.4%) |
| Missing | 4 (8.9%) | 3 (7.1%) |
| CSS responder | 18 (40.0%) | 29 (69.0%) |
| CSS non-responder | 23 (51.1%) | 10 (23.8%) |
| Missing | 4 (8.9%) | 3 (7.1%) |
| Missing as non-responder | 27 (60.0%) | 13 (31.0%) |
| P-value Responder vs. non-responder | | 0.0057 |
| P-value Responder vs. non-responder/Missing | | 0.0066 |
| WEEK 24 | | |
| ABSENT | 9 (20.0%) | 24 (57.1%) |
| MILD | 19 (42.2%) | 12 (28.6%) |
| MODERATE | 8 (17.8%) | 1 (2.4%) |
| SEVERE | 3 (6.7%) | 1 (2.4%) |
| Missing | 6 (13.3%) | 4 (9.5%) |
| CSS responder | 22 (48.9%) | 29 (69.0%) |
| CSS non-responder | 17 (37.8%) | 9 (21.4%) |
| Missing | 6 (13.3%) | 4 (9.5%) |
| Missing as non-responder | 23 (51.1%) | 13 (31.0%) |
| P-value Responder vs. non-responder | | 0.0648 |
| P-value Responder vs. non-responder/Missing | | 0.0564 |
| WEEK 28 | | |
| ABSENT | 8 (17.8%) | 21 (50.0%) |
| MILD | 17 (37.8%) | 14 (33.3%) |
| MODERATE | 12 (26.7%) | 0 (0.0%) |
| SEVERE | 2 (4.4%) | 1 (2.4%) |
| Missing | 6 (13.3%) | 6 (14.3%) |
| CSS responder | 19 (42.2%) | 29 (69.0%) |
| CSS non-responder | 20 (44.4%) | 7 (16.7%) |
| Missing | 6 (13.3%) | 6 (14.3%) |
| Missing as non-responder | 26 (57.8%) | 13 (31.0%) |
| P-value Responder vs. non-responder | | 0.0041 |
| P-value Responder vs. non-responder/Missing | | 0.0119 |
| WEEK 72 | | |
| ABSENT | 14 (31.1%) | 20 (47.6%) |
| MILD | 15 (33.3%) | 12 (28.6%) |
| MODERATE | 8 (17.8%) | 2 (4.8%) |
| SEVERE | 1 (2.2%) | 2 (4.8%) |
| Missing | 7 (15.6%) | 6 (14.3%) |
| CSS responder | 21 (46.7%) | 24 (57.1%) |
| CSS non-responder | 17 (37.8%) | 12 (28.6%) |
| Missing | 7 (15.6%) | 6 (14.3%) |
| Missing as non-responder | 24 (53.3%) | 18 (42.9%) |
| P-value Responder vs. non-responder | | 0.3152 |
| P-value Responder vs. non-responder/Missing | | 0.3285 |
| Non-study Eye | 45 | 42 |
| BASELINE | | |
| ABSENT | 1 (2.2%) | 8 (19.0%) |
| MILD | 21 (46.7%) | 15 (35.7%) |
| MODERATE | 20 (44.4%) | 19 (45.2%) |
| SEVERE | 3 (6.7%) | 0 (0.0%) |
| Missing | 0 (0.0%) | 0 (0.0%) |
| WEEK 6 | | |
| ABSENT | 3 (6.7%) | 17 (40.5%) |
| MILD | 21 (46.7%) | 17 (40.5%) |
| MODERATE | 15 (33.3%) | 6 (14.3%) |
| SEVERE | 3 (6.7%) | 0 (0.0%) |
| Missing | 3 (6.7%) | 2 (4.8%) |
| CSS responder | 9 (20.0%) | 18 (42.9%) |
| CSS non-responder | 33 (73.3%) | 22 (52.4%) |
| Missing | 3 (6.7%) | 2 (4.8%) |
| Missing as non-responder | 36 (80.0%) | 24 (57.1%) |
| P-value Responder vs. non-responder | | 0.0232 |
| P-value Responder vs. non-responder/Missing | | 0.0213 |
| WEEK 12 | | |
| ABSENT | 5 (11.1%) | 22 (52.4%) |
| MILD | 20 (44.4%) | 14 (33.3%) |
| MODERATE | 14 (31.1%) | 4 (9.5%) |
| SEVERE | 2 (4.4%) | 0 (0.0%) |
| Missing | 4 (8.9%) | 2 (4.8%) |
| CSS responder | 13 (28.9%) | 22 (52.4%) |
| CSS non-responder | 28 (62.2%) | 18 (42.9%) |
| Missing | 4 (8.9%) | 2 (4.8%) |
| Missing as non-responder | 32 (71.1%) | 20 (47.6%) |
| P-value Responder vs. non-responder | | 0.0344 |
| P-value Responder vs. non-responder/Missing | | 0.0256 |
| WEEK 18 | | |
| ABSENT | 6 (13.3%) | 21 (50.0%) |
| MILD | 22 (48.9%) | 17 (40.5%) |
| MODERATE | 11 (24.4%) | 1 (2.4%) |
| SEVERE | 2 (4.4%) | 0 (0.0%) |
| Missing | 4 (8.9%) | 3 (7.1%) |
| CSS responder | 13 (28.9%) | 24 (57.1%) |
| CSS non-responder | 28 (62.2%) | 15 (35.7%) |
| Missing | 4 (8.9%) | 3 (7.1%) |
| Missing as non-responder | 32 (71.1%) | 18 (42.9%) |
| P-value Responder vs. non-responder | | 0.0075 |
| P-value Responder vs. non-responder/Missing | | 0.0077 |
| WEEK 24 | | |
| ABSENT | 8 (17.8%) | 25 (59.5%) |
| MILD | 22 (48.9%) | 10 (23.8%) |
| MODERATE | 7 (15.6%) | 3 (7.1%) |
| SEVERE | 2 (4.4%) | 0 (0.0%) |
| Missing | 6 (13.3%) | 4 (9.5%) |
| CSS responder | 18 (40.0%) | 24 (57.1%) |
| CSS non-responder | 21 (46.7%) | 14 (33.3%) |
| Missing | 6 (13.3%) | 4 (9.5%) |
| Missing as non-responder | 27 (60.0%) | 18 (42.9%) |
| P-value Responder vs. non-responder | | 0.1341 |
| P-value Responder vs. non-responder/Missing | | 0.1098 |
| WEEK 28 | | |
| ABSENT | 8 (17.8%) | 23 (54.8%) |
| MILD | 19 (42.2%) | 12 (28.6%) |
| MODERATE | 11 (24.4%) | 1 (2.4%) |
| SEVERE | 1 (2.2%) | 0 (0.0%) |
| Missing | 6 (13.3%) | 6 (14.3%) |
| CSS responder | 15 (33.3%) | 23 (54.8%) |
| CSS non-responder | 24 (53.3%) | 13 (31.0%) |
| Missing | 6 (13.3%) | 6 (14.3%) |
| Missing as non-responder | 30 (66.7%) | 19 (45.2%) |
| P-value Responder vs. non-responder | | 0.0278 |
| P-value Responder vs. non-responder/Missing | | 0.044 |
| WEEK 72 | | |
| ABSENT | 16 (35.6%) | 21 (50.0%) |
| MILD | 13 (28.9%) | 12 (28.6%) |

TABLE 12-continued

Individual CSS by Treatment Group and Visit - Swelling of the Eyelids Imputation for Subjects Receiving TED During Follow-up (ITT Population)

|  | Placebo | RV 001 |
|---|---|---|
| MODERATE | 8 (17.8%) | 2 (4.8%) |
| SEVERE | 1 (2.2%) | 1 (2.4%) |
| Missing | 7 (15.6%) | 6 (14.3%) |
| CSS responder | 18 (40.0%) | 20 (47.6%) |
| CSS non-responder | 20 (44.4%) | 16 (38.1%) |
| Missing | 7 (15.6%) | 6 (14.3%) |
| Missing as non-responder | 27 (60.0%) | 22 (52.4%) |
| P-value Responder vs. non-responder |  | 0.4813 |
| P-value Responder vs. non-responder/Missing |  | 0.474 |

Note:
Subjects who received TED treatment in the follow-up were treated as non-responders from the time of TED treatment forward.
CSS responders are defined as subjects who experienced a decrease of >=1 grade.
The p-values are from Chi square tests without continuity correction.

TABLE 13

Individual CSS by Treatment Group and Visit - Conjunctival Edema Imputation for Subjects Receiving TED During Follow-up (ITT Population)

|  | Placebo | RV 001 |
|---|---|---|
| Study Eye | 45 | 42 |
| BASELINE |  |  |
| ABSENT | 14 (31.1%) | 17 (40.5%) |
| PRESENT | 31 (68.9%) | 25 (59.5%) |
| Missing | 0 (0.0%) | 0 (0.0%) |
| WEEK 6 |  |  |
| ABSENT | 15 (33.3%) | 32 (76.2%) |
| PRESENT | 27 (60.0%) | 8 (19.0%) |
| Missing | 3 (6.7%) | 2 (4.8%) |
| CSS responder | 6 (13.3%) | 15 (35.7%) |
| CSS non-responder | 36 (80.0%) | 25 (59.5%) |
| Missing | 3 (6.7%) | 2 (4.8%) |
| Missing as non-responder | 39 (86.7%) | 27 (64.3%) |
| P-value Responder vs. non-responder |  | 0.0161 |
| P-value Responder vs. non-responder/Missing |  | 0.0148 |
| WEEK 12 |  |  |
| ABSENT | 21 (46.7%) | 34 (81.0%) |
| PRESENT | 20 (44.4%) | 6 (14.3%) |
| Missing | 4 (8.9%) | 2 (4.8%) |
| CSS responder | 10 (22.2%) | 17 (40.5%) |
| CSS non-responder | 31 (68.9%) | 23 (54.8%) |
| Missing | 4 (8.9%) | 2 (4.8%) |
| Missing as non-responder | 35 (77.8%) | 25 (59.5%) |
| P-value Responder vs. non-responder |  | 0.0839 |
| P-value Responder vs. non-responder/Missing |  | 0.0659 |
| WEEK 18 |  |  |
| ABSENT | 21 (46.7%) | 36 (85.7%) |
| PRESENT | 20 (44.4%) | 3 (7.1%) |
| Missing | 4 (8.9%) | 3 (7.1%) |
| CSS responder | 10 (22.2%) | 20 (47.6%) |
| CSS non-responder | 31 (68.9%) | 19 (45.2%) |
| Missing | 4 (8.9%) | 3 (7.1%) |
| Missing as non-responder | 35 (77.8%) | 22 (52.4%) |
| P-value Responder vs. non-responder |  | 0.013 |
| P-value Responder vs. non-responder/Missing |  | 0.0128 |
| WEEK 24 |  |  |
| ABSENT | 23 (51.1%) | 35 (83.3%) |
| PRESENT | 16 (35.6%) | 3 (7.1%) |
| Missing | 6 (13.3%) | 4 (9.5%) |
| CSS responder | 12 (26.7%) | 19 (45.2%) |

TABLE 13-continued

Individual CSS by Treatment Group and Visit - Conjunctival Edema Imputation for Subjects Receiving TED During Follow-up (ITT Population)

|  | Placebo | RV 001 |
|---|---|---|
| CSS non-responder | 27 (60.0%) | 19 (45.2%) |
| Missing | 6 (13.3%) | 4 (9.5%) |
| Missing as non-responder | 33 (73.3%) | 23 (54.8%) |
| P-value Responder vs. non-responder |  | 0.0854 |
| P-value Responder vs. non-responder/Missing |  | 0.0707 |
| WEEK 28 |  |  |
| ABSENT | 24 (53.3%) | 33 (78.6%) |
| PRESENT | 15 (33.3%) | 3 (7.1%) |
| Missing | 6 (13.3%) | 6 (14.3%) |
| CSS responder | 12 (26.7%) | 18 (42.9%) |
| CSS non-responder | 27 (60.0%) | 18 (42.9%) |
| Missing | 6 (13.3%) | 6 (14.3%) |
| Missing as non-responder | 33 (73.3%) | 24 (57.1%) |
| P-value Responder vs. non-responder |  | 0.0894 |
| P-value Responder vs. non-responder/Missing |  | 0.1124 |
| WEEK 72 |  |  |
| ABSENT | 31 (68.9%) | 34 (81.0%) |
| PRESENT | 7 (15.6%) | 2 (4.8%) |
| Missing | 7 (15.6%) | 6 (14.3%) |
| CSS responder | 16 (35.6%) | 16 (38.1%) |
| CSS non-responder | 22 (48.9%) | 20 (47.6%) |
| Missing | 7 (15.6%) | 6 (14.3%) |
| Missing as non-responder | 29 (64.4%) | 26 (61.9%) |
| P-value Responder vs. non-responder |  | 0.8391 |
| P-value Responder vs. non-responder/Missing |  | 0.8061 |
| Non-study Eye | 45 | 42 |
| BASELINE |  |  |
| ABSENT | 17 (37.8%) | 20 (47.6%) |
| PRESENT | 28 (62.2%) | 22 (52.4%) |
| Missing | 0 (0.0%) | 0 (0.0%) |
| WEEK 6 |  |  |
| ABSENT | 19 (42.2%) | 35 (83.3%) |
| PRESENT | 23 (51.1%) | 5 (11.9%) |
| Missing | 3 (6.7%) | 2 (4.8%) |
| CSS responder | 7 (15.6%) | 15 (35.7%) |
| CSS non-responder | 35 (77.8%) | 25 (59.5%) |
| Missing | 3 (6.7%) | 2 (4.8%) |
| Missing as non-responder | 38 (84.4%) | 27 (64.3%) |
| P-value Responder vs. non-responder |  | 0.0333 |
| P-value Responder vs. non-responder/Missing |  | 0.0306 |
| WEEK 12 |  |  |
| ABSENT | 24 (53.3%) | 35 (83.3%) |
| PRESENT | 17 (37.8%) | 5 (11.9%) |
| Missing | 4 (8.9%) | 2 (4.8%) |
| CSS responder | 8 (17.8%) | 15 (35.7%) |
| CSS non-responder | 33 (73.3%) | 25 (59.5%) |
| Missing | 4 (8.9%) | 2 (4.8%) |
| Missing as non-responder | 37 (82.2%) | 27 (64.3%) |
| P-value Responder vs. non-responder |  | 0.0727 |
| P-value Responder vs. non-responder/Missing |  | 0.058 |
| WEEK 18 |  |  |
| ABSENT | 24 (53.3%) | 34 (81.0%) |
| PRESENT | 17 (37.8%) | 5 (11.9%) |
| Missing | 4 (8.9%) | 3 (7.1%) |
| CSS responder | 8 (17.8%) | 15 (35.7%) |
| CSS non-responder | 33 (73.3%) | 24 (57.1%) |
| Missing | 4 (8.9%) | 3 (7.1%) |
| Missing as non-responder | 37 (82.2%) | 27 (64.3%) |
| P-value Responder vs. non-responder |  | 0.0612 |
| P-value Responder vs. non-responder/Missing |  | 0.058 |

TABLE 13-continued

Individual CSS by Treatment Group and Visit - Conjunctival Edema
Imputation for Subjects Receiving TED During Follow-up
(ITT Population)

|  | Placebo | RV 001 |
|---|---|---|
| WEEK 24 |  |  |
| ABSENT | 26 (57.8%) | 34 (81.0%) |
| PRESENT | 13 (28.9%) | 4 (9.5%) |
| Missing | 6 (13.3%) | 4 (9.5%) |
| CSS responder | 12 (26.7%) | 15 (35.7%) |
| CSS non-responder | 27 (60.0%) | 23 (54.8%) |
| Missing | 6 (13.3%) | 4 (9.5%) |
| Missing as non-responder | 33 (73.3%) | 27 (64.3%) |
| P-value Responder vs. non-responder |  | 0.4235 |
| P-value Responder vs. non-responder/Missing |  | 0.362 |
| WEEK 28 |  |  |
| ABSENT | 24 (53.3%) | 32 (76.2%) |
| PRESENT | 15 (33.3%) | 4 (9.5%) |
| Missing | 6 (13.3%) | 6 (14.3%) |
| CSS responder | 10 (22.2%) | 14 (33.3%) |
| CSS non-responder | 29 (64.4%) | 22 (52.4%) |
| Missing | 6 (13.3%) | 6 (14.3%) |
| Missing as non-responder | 35 (77.8%) | 28 (66.7%) |
| P-value Responder vs. non-responder |  | 0.2192 |
| P-value Responder vs. non-responder/Missing |  | 0.2466 |
| WEEK 72 |  |  |
| ABSENT | 31 (68.9%) | 31 (73.8%) |
| PRESENT | 7 (15.6%) | 5 (11.9%) |
| Missing | 7 (15.6%) | 6 (14.3%) |
| CSS responder | 14 (31.1%) | 12 (28.6%) |
| CSS non-responder | 24 (53.3%) | 24 (57.1%) |
| Missing | 7 (15.6%) | 6 (14.3%) |
| Missing as non-responder | 31 (68.9%) | 30 (71.4%) |
| P-value Responder vs. non-responder |  | 0.752 |
| P-value Responder vs. non-responder/Missing |  | 0.7959 |

Note:
Subjects who received TED treatment in the follow-up were treated as non-responders from the time of TED treatment forward.
CSS responders are defined as subjects who experienced a decrease of >=1 grade (changed from Present to Absent).
The p-values are from Chi square tests without continuity correction.

TABLE 14

Individual CSS by Treatment Group and Visit - Subjective Diplopia Score
Imputation for Subjects Receiving TED During Follow-up
(ITT Population)

|  | Placebo | RV 001 |
|---|---|---|
| Study Eye | 45 | 42 |
| BASELINE |  |  |
| 0, NO DIPLOPIA | 14 (31.1%) | 4 (9.5%) |
| 1, INTERMITTENT | 19 (42.2%) | 16 (38.1%) |
| 2, INCONSTANT | 8 (17.8%) | 7 (16.7%) |
| 3, CONSTANT | 4 (8.9%) | 15 (35.7%) |
| Missing | 0 (0.0%) | 0 (0.0%) |
| WEEK 6 |  |  |
| 0, NO DIPLOPIA | 18 (40.0%) | 13 (31.0%) |
| 1, INTERMITTENT | 12 (26.7%) | 11 (26.2%) |
| 2, INCONSTANT | 8 (17.8%) | 6 (14.3%) |
| 3, CONSTANT | 4 (8.9%) | 10 (23.8%) |
| Missing | 3 (6.7%) | 2 (4.8%) |
| CSS responder | 9 (20.0%) | 17 (40.5%) |
| CSS non-responder | 33 (73.3%) | 23 (54.8%) |
| Missing | 3 (6.7%) | 2 (4.8%) |
| Missing as non-responder | 36 (80.0%) | 25 (59.5%) |
| P-value Responder vs. non-responder |  | 0.0404 |
| P-value Responder vs. non-responder/Missing |  | 0.0371 |
| WEEK 12 |  |  |
| 0, NO DIPLOPIA | 20 (44.4%) | 16 (38.1%) |
| 1, INTERMITTENT | 9 (20.0%) | 8 (19.0%) |
| 2, INCONSTANT | 7 (15.6%) | 9 (21.4%) |
| 3, CONSTANT | 5 (11.1%) | 7 (16.7%) |
| Missing | 4 (8.9%) | 2 (4.8%) |
| CSS responder | 10 (22.2%) | 24 (57.1%) |
| CSS non-responder | 31 (68.9%) | 16 (38.1%) |
| Missing | 4 (8.9%) | 2 (4.8%) |
| Missing as non-responder | 35 (77.8%) | 18 (42.9%) |
| P-value Responder vs. non-responder |  | 0.0012 |
| P-value Responder vs. non-responder/Missing |  | 0.0009 |
| WEEK 18 |  |  |
| 0, NO DIPLOPIA | 19 (42.2%) | 16 (38.1%) |
| 1, INTERMITTENT | 9 (20.0%) | 8 (19.0%) |
| 2, INCONSTANT | 8 (17.8%) | 8 (19.0%) |
| 3, CONSTANT | 5 (11.1%) | 7 (16.7%) |
| Missing | 4 (8.9%) | 3 (7.1%) |
| CSS responder | 11 (24.4%) | 23 (54.8%) |
| CSS non-responder | 30 (66.7%) | 16 (38.1%) |
| Missing | 4 (8.9%) | 3 (7.1%) |
| Missing as non-responder | 34 (75.6%) | 19 (45.2%) |
| P-value Responder vs. non-responder |  | 0.0036 |
| P-value Responder vs. non-responder/Missing |  | 0.0038 |
| WEEK 24 |  |  |
| 0, NO DIPLOPIA | 18 (40.0%) | 21 (50.0%) |
| 1, INTERMITTENT | 8 (17.8%) | 4 (9.5%) |
| 2, INCONSTANT | 7 (15.6%) | 9 (21.4%) |
| 3, CONSTANT | 6 (13.3%) | 4 (9.5%) |
| Missing | 6 (13.3%) | 4 (9.5%) |
| CSS responder | 10 (22.2%) | 26 (61.9%) |
| CSS non-responder | 29 (64.4%) | 12 (28.6%) |
| Missing | 6 (13.3%) | 4 (9.5%) |
| Missing as non-responder | 35 (77.8%) | 16 (38.1%) |
| P-value Responder vs. non-responder |  | 0.0002 |
| P-value Responder vs. non-responder/Missing |  | 0.0002 |
| WEEK 28 |  |  |
| 0, NO DIPLOPIA | 19 (42.2%) | 16 (38.1%) |
| 1, INTERMITTENT | 7 (15.6%) | 6 (14.3%) |
| 2, INCONSTANT | 6 (13.3%) | 10 (23.8%) |
| 3, CONSTANT | 7 (15.6%) | 4 (9.5%) |
| Missing | 6 (13.3%) | 6 (14.3%) |
| CSS responder | 9 (20.0%) | 23 (54.8%) |
| CSS non-responder | 30 (66.7%) | 13 (31.0%) |
| Missing | 6 (13.3%) | 6 (14.3%) |
| Missing as non-responder | 36 (80.0%) | 19 (45.2%) |
| P-value Responder vs. non-responder |  | 0.0004 |
| P-value Responder vs. non-responder/Missing |  | 0.0008 |
| WEEK 72 |  |  |
| 0, NO DIPLOPIA | 21 (46.7%) | 20 (47.6%) |
| 1, INTERMITTENT | 7 (15.6%) | 4 (9.5%) |
| 2, INCONSTANT | 5 (11.1%) | 6 (14.3%) |
| 3, CONSTANT | 5 (11.1%) | 6 (14.3%) |
| Missing | 7 (15.6%) | 6 (14.3%) |
| CSS responder | 11 (24.4%) | 21 (50.0%) |
| CSS non-responder | 27 (60.0%) | 15 (35.7%) |
| Missing | 7 (15.6%) | 6 (14.3%) |
| Missing as non-responder | 34 (75.6%) | 21 (50.0%) |
| P-value Responder vs. non-responder |  | 0.0108 |
| P-value Responder vs. non-responder/Missing |  | 0.0135 |
| Non-study Eye | 45 | 42 |

TABLE 14-continued

Individual CSS by Treatment Group
and Visit - Subjective Diplopia Score
Imputation for Subjects Receiving TED During Follow-up
(ITT Population)

|  | Placebo | RV 001 |
|---|---|---|
| BASELINE | | |
| 0, NO DIPLOPIA | 15 (33.3%) | 4 (9.5%) |
| 1, INTERMITTENT | 20 (44.4%) | 16 (38.1%) |
| 2, INCONSTANT | 6 (13.3%) | 7 (16.7%) |
| 3, CONSTANT | 4 (8.9%) | 15 (35.7%) |
| Missing | 0 (0.0%) | 0 (0.0%) |
| WEEK 6 | | |
| 0, NO DIPLOPIA | 19 (42.2%) | 14 (33.3%) |
| 1, INTERMITTENT | 12 (26.7%) | 10 (23.8%) |
| 2, INCONSTANT | 7 (15.6%) | 7 (16.7%) |
| 3, CONSTANT | 4 (8.9%) | 9 (21.4%) |
| Missing | 3 (6.7%) | 2 (4.8%) |
| CSS responder | 9 (20.0%) | 19 (45.2%) |
| CSS non-responder | 33 (73.3%) | 21 (50.0%) |
| Missing | 3 (6.7%) | 2 (4.8%) |
| Missing as non-responder | 36 (80.0%) | 23 (54.8%) |
| P-value Responder vs. non-responder | | 0.0128 |
| P-value Responder vs. non-responder/Missing | | 0.0118 |
| WEEK 12 | | |
| 0, NO DIPLOPIA | 21 (46.7%) | 17 (40.5%) |
| 1, INTERMITTENT | 9 (20.0%) | 8 (19.0%) |
| 2, INCONSTANT | 6 (13.3%) | 10 (23.8%) |
| 3, CONSTANT | 5 (11.1%) | 5 (11.9%) |
| Missing | 4 (8.9%) | 2 (4.8%) |
| CSS responder | 10 (22.2%) | 27 (64.3%) |
| CSS non-responder | 31 (68.9%) | 13 (31.0%) |
| Missing | 4 (8.9%) | 2 (4.8%) |
| Missing as non-responder | 35 (77.8%) | 15 (35.7%) |
| P-value Responder vs. non-responder | | 0.0001 |
| P-value Responder vs. non-responder/Missing | | 0.0001 |
| WEEK 18 | | |
| 0, NO DIPLOPIA | 19 (42.2%) | 16 (38.1%) |
| 1, INTERMITTENT | 9 (20.0%) | 8 (19.0%) |
| 2, INCONSTANT | 8 (17.8%) | 8 (19.0%) |
| 3, CONSTANT | 5 (11.1%) | 7 (16.7%) |
| Missing | 4 (8.9%) | 3 (7.1%) |
| CSS responder | 11 (24.4%) | 23 (54.8%) |
| CSS non-responder | 30 (66.7%) | 16 (38.1%) |
| Missing | 4 (8.9%) | 3 (7.1%) |
| Missing as non-responder | 34 (75.6%) | 19 (45.2%) |
| P-value Responder vs. non-responder | | 0.0036 |
| P-value Responder vs. non-responder/Missing | | 0.0038 |
| WEEK 24 | | |
| 0, NO DIPLOPIA | 18 (40.0%) | 21 (50.0%) |
| 1, INTERMITTENT | 8 (17.8%) | 4 (9.5%) |
| 2, INCONSTANT | 7 (15.6%) | 9 (21.4%) |
| 3, CONSTANT | 6 (13.3%) | 4 (9.5%) |
| Missing | 6 (13.3%) | 4 (9.5%) |
| CSS responder | 10 (22.2%) | 26 (61.9%) |
| CSS non-responder | 29 (64.4%) | 12 (28.6%) |
| Missing | 6 (13.3%) | 4 (9.5%) |
| Missing as non-responder | 35 (77.8%) | 16 (38.1%) |
| P-value Responder vs. non-responder | | 0.0002 |
| P-value Responder vs. non-responder/Missing | | 0.0002 |
| WEEK 28 | | |
| 0, NO DIPLOPIA | 19 (42.2%) | 16 (38.1%) |
| 1, INTERMITTENT | 7 (15.6%) | 6 (14.3%) |
| 2, INCONSTANT | 6 (13.3%) | 10 (23.8%) |
| 3, CONSTANT | 7 (15.6%) | 4 (9.5%) |
| Missing | 6 (13.3%) | 6 (14.3%) |
| CSS responder | 9 (20.0%) | 23 (54.8%) |
| CSS non-responder | 30 (66.7%) | 13 (31.0%) |
| Missing | 6 (13.3%) | 6 (14.3%) |
| Missing as non-responder | 36 (80.0%) | 19 (45.2%) |
| P-value Responder vs. non-responder | | 0.0004 |
| P-value Responder vs. non-responder/Missing | | 0.0008 |
| WEEK 72 | | |
| 0, NO DIPLOPIA | 21 (46.7%) | 20 (47.6%) |
| 1, INTERMITTENT | 7 (15.6%) | 3 (7.1%) |
| 2, INCONSTANT | 5 (11.1%) | 6 (14.3%) |
| 3, CONSTANT | 5 (11.1%) | 7 (16.7%) |
| Missing | 7 (15.6%) | 6 (14.3%) |
| CSS responder | 11 (24.4%) | 20 (47.6%) |
| CSS non-responder | 27 (60.0%) | 16 (38.1%) |
| Missing | 7 (15.6%) | 6 (14.3%) |
| Missing as non-responder | 34 (75.6%) | 22 (52.4%) |
| P-value Responder vs. non-responder | | 0.0204 |
| P-value Responder vs. non-responder/Missing | | 0.0241 |

Note:
Subject diplopia score is defined as 0, no diplopia;
1, intermittent, i.e. diplopia in primary position of gaze, when tired or when first awakening;
2, inconstant, i.e. diplopia at extremes of gaze;
3, constant, i.e. continuous diplopia in primary of reading position.
Subjects who received TED treatment in the follow-up were treated as non-responders from the time of TED treatment forward.
CSS responders are defined as subjects who had a decrease >=1 grade.
The p-values are from Chi square tests without continuity correction.

TABLE 15

ANCOVA Analysis of Change from Baseline in GO-QOL
Transformed Total Score at WEEK s 28, 48 and 72 (ITT Population)

|  | Placebo (N = 45) | RV 001 (N = 42) |
|---|---|---|
| WEEK 28 | | |
| n | 37 | 37 |
| Mean (SD) | 6.29 (24.080) | 21.58 (22.002) |
| Median | 9.38 | 20.62 |
| Q1, Q3 | −9.38, 25.00 | 9.38, 33.33 |
| Min, Max | −62.50, 48.96 | −21.88, 87.50 |
| WEEK 28 (ANCOVA) | | |
| LS Mean (SE) | 5.16 (3.201) | 22.12 (3.372) |
| Difference in LS Mean (SE) | | 16.96 (4.481) |
| 95% CI for Difference | | 8.027, 25.900 |
| P-value | | <0.001 |
| WEEK 48 | | |
| n | 33 | 37 |
| Mean (SD) | 12.82 (23.419) | 18.49 (21.887) |
| Median | 12.5 | 15.62 |
| Q1, Q3 | −6.25, 28.12 | 6.25, 30.00 |
| Min, Max | −25.00, 83.33 | −25.00, 87.50 |
| WEEK 48 (ANCOVA) | | |
| LS Mean (SE) | 9.71 (3.267) | 18.49 (3.227) |
| Difference in LS Mean (SE) | | 8.78 (4.412) |
| 95% CI for Difference | | −0.030, 17.586 |
| P-value | | 0.0508 |
| WEEK 72 | | |
| n | 32 | 33 |
| Mean (SD) | 14.69 (20.140) | 12.72 (20.719) |
| Median | 12.5 | 12.5 |
| Q1, Q3 | 3.12, 26.56 | 0.00, 24.17 |
| Min, Max | −31.25, 77.08 | −53.12, 50.00 |

TABLE 15-continued

ANCOVA Analysis of Change from Baseline in GO-QOL Transformed Total Score at WEEK s 28, 48 and 72 (ITT Population)

|  | Placebo (N = 45) | RV 001 (N = 42) |
| --- | --- | --- |
| WEEK 72 (ANCOVA) | | |
| LS Mean (SE) | 12.08 (3.429) | 13.82 (3.502) |
| Difference in LS Mean (SE) | | 1.74 (4.761) |
| 95% CI for Difference | | −7.780, 11.262 |
| P-value | | 0.7159 |

Note:
Separate ANCOVA (Analysis of Covariance) models were applied to WEEK 28, WEEK 49, and WEEK 72 data. The ANCOVA included Baseline values and smoke status as covariates.
Subjects who received TED treatment in the follow-up were excluded from the analyses from the time of TED treatment forward.

TABLE 16

Summary of Graded Proptosis Response at WEEK 28

|  | Placebo | | RV 001 | |
| --- | --- | --- | --- | --- |
|  | N | | | |
|  | 45 | | 42 | |
|  | No. subjects | % | No. subjects | % |
| High Response | 3 | 6.67% | 23 | 54.76% |
| Response | 3 | 6.67% | 8 | 19.05% |
| Low Response | 10 | 22.22% | 4 | 9.52% |
| No Response | 22 | 48.89% | 1 | 2.38% |
| Missing | 7 | 15.56% | 6 | 14.29% |
| Total | 45 | 100.00% | 42 | 100.00% |

Note 1:
high response (proptosis reduction ≥3 mm); response (2 mm ≤ proptosis reduction <3 mm); low response (1 mm ≤ proptosis reduction <2 mm); no response (proptosis reduction <1 mm).

Note 2:
Subjects who received additional TED treatment prior to WEEK 28 were considered as no response. This rule would apply to two Placebo subjects. One subject was not a responder (proptosis was increased by 2.5 mm at WEEK 28); one subject (proptosis was reduced by 2 mm at WEEK 28) would be a responder but was considered as no response in the summary table.

TABLE 17

Sequences and SEQ ID Numbers

| SEQ ID NO | Description | Sequence |
| --- | --- | --- |
|  | Antibody 1 (teprotumumab) | |
| 1 | CDRH1 aa | Ser Tyr Gly Met His |
| 2 | CDRH2 aa | Ile Ile Trp Phe Asp Gly Ser Ser Thr Tyr Tyr Ala Asp Ser Val Arg Gly |
| 3 | CDRH3 aa | Glu Leu Gly Arg Arg Tyr Phe Asp Leu |
| 4 | CDRL1 aa | Arg Ala Ser Gln Ser Val Ser Ser Tyr Leu Ala |
| 5 | CDRL2 aa | Asp Ala Ser Lys Arg Ala Thr |
| 6 | CDRL3 aa | Gln Gln Arg Ser Lys Trp Pro Pro Trp Thr |
| 7 | VH aa | Gln Val Glu Leu Val Glu Ser Gly Gly Gly Val Val Gln Pro Gly Arg Ser Gln Arg Leu Ser Cys Ala Ala Ser Gly Phe Thr Phe Ser Ser Tyr Gly Met His Trp Val Arg Gln Ala Pro Gly Lys Gly Leu Glu Trp Val Ala Ile Ile Trp Phe Asp Gly Ser Ser Thr Tyr Tyr Ala Asp Ser Val Arg Gly Arg Phe Thr Ile Ser Arg Asp Asn Ser Lys Asn Thr Leu Tyr Leu Gln Met Asn Ser Leu Arg Ala Glu Asp Thr Ala Val Tyr Phe Cys Ala Arg Glu Leu Gly Arg Arg Tyr Phe Asp Leu Trp Gly Arg Gly Thr Leu Val Ser Val Ser Ser |
| 8 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Lys Arg Ala Thr Gly Ile Pro Ala Arg Phe Ser Gly Ser Gly Ser Gly Thr Asp Phe Thr Leu Thr Be Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ser Lys |
|  | Antibody 2 | |
| 1 | CDRH1 aa | Ser Tyr Gly Met His |
| 9 | CDRH2 aa | Ile Ile Trp Phe Asp Gly Ser Ser Lys Tyr Tyr Gly Asp Ser Val Lys Gly |
| 3 | CDRH3 aa | Glu Leu Gly Arg Arg Tyr Phe Asp Leu |
| 4 | CDRL1 aa | Arg Ala Ser Gln Ser Val Ser Ser Tyr Leu Ala |

TABLE 17-continued

Sequences and SEQ ID Numbers

| SEQ ID NO | Description | Sequence |
|---|---|---|
| 10 | CDRL2 aa | Asp Ala Ser Asn Arg Ala Thr |
| 6 | CDRL3 aa | Gln Gln Arg Ser Lys Trp Pro Pro Trp Thr |
| 11 | VH aa | Gln Val Gln Leu Val Glu Ser Gly Gly Gly Val Val Gln Pro Gly<br>Arg Ser Leu Arg Leu Ser Cys Ala Ala Ser Gly Phe Thr Phe Ser<br>Ser Tyr Gly Met His Trp Val Arg Gln Ala Pro Gly Lys Gly Leu<br>Glu Trp Met Ala Ile Ile Trp Phe Asp Gly Ser Ser Lys Tyr Tyr<br>Gly Asp Ser Val Lys Gly Arg Phe Thr Ile Ser Arg Asp Asn Ser<br>Lys Asn Thr Leu Tyr Leu Gln Met Asn Ser Leu Arg Ala Asp Asp<br>Thr Ala Val Tyr Tyr Cys Ala Arg Glu Leu Gly Arg Arg Tyr Phe<br>Asp Leu Trp Gly Arg Gly Thr Leu Val Thr Val Ser Ser |
| 12 | VL aa | Glu Ile Val Leu Thr Gln Ser Pro Ala Thr Leu Ser Leu Ser Pro<br>Gly Glu Arg Ala Thr Leu Ser Cys Arg Ala Ser Gln Ser Val Ser<br>Ser Tyr Leu Ala Trp Tyr Gln Gln Lys Pro Gly Gln Ala Pro Arg<br>Leu Leu Ile Tyr Asp Ala Ser Asn Arg Ala Thr Gly Ile Pro Ala<br>Arg Phe Ser Gly Ser Gly Ser Gly Thr Asp Phe Thr Leu Thr Ile<br>Ser Ser Leu Glu Pro Glu Asp Phe Ala Val Tyr Tyr Cys Gln Gln<br>Arg Ser Lys Trp Pro Pro Trp Thr Phe Gly Gln Gly Thr Lys Val<br>Glu Ile Lys |

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fail within the scope of the appended claims.

The invention claimed is:

1. A method of treating a subject with thyroid eye disease, comprising:

reducing proptosis in the subject with thyroid eye disease by administering to the subject an antibody comprising a heavy chain comprising CDRH1, CDRH2, and CDRH3 and a light chain comprising CDRL1, CDRL2, and CDRL3, as set forth in SEQ ID NOs: 1-6, respectively, wherein the antibody specifically binds and inhibits insulin-like growth factor I receptor, wherein the antibody is administered at a dosage of about 5 mg/kg to about 10 mg/kg antibody as a first dose, and wherein the proptosis is reduced by at least 3 mm.

2. The method of claim 1, wherein the antibody comprises a heavy chain variable region comprising the amino acid sequence of SEQ ID NO: 7 and a light chain variable region comprising the amino acid sequence of SEQ ID NO: 8.

3. The method of claim 2, wherein the antibody is a human monoclonal antibody.

4. The method of claim 3, wherein the antibody is IgG.

5. The method of claim 4, wherein the antibody is IgG1.

6. The method of claim 5, wherein the antibody is teprotumumab.

7. The method of claim 1, wherein the antibody is administered at a dosage of about 5 mg/kg to about 20 mg/kg in subsequent doses.

8. The method of claim 7, wherein the antibody comprises a heavy chain variable region comprising the amino acid sequence of SEQ ID NO: 7 and a light chain variable region comprising the amino acid sequence of SEQ ID NO: 8.

9. The method of claim 7, wherein the antibody is administered in the following amounts:
about 10 mg/kg as a first dose; and
about 20 mg/kg in subsequent doses.

10. The method of claim 9, wherein the antibody is teprotumumab.

11. The method of claim 9, wherein the subsequent doses are administered every three weeks for at least 21 weeks.

12. The method of claim 11, wherein the antibody comprises a heavy chain variable region comprising the amino acid sequence of SEQ ID NO: 7 and a light chain variable region comprising the amino acid sequence of SEQ ID NO: 8.

13. The method of claim 11, wherein the antibody is teprotumumab.

14. The method of claim 7, wherein the subsequent doses are administered every three weeks for at least 21 weeks.

15. The method of claim 1, wherein the antibody is administered by intravenous infusion.

16. A method of treating a subject with thyroid eye disease, comprising:
reducing proptosis in the subject with thyroid eye disease by administering to the subject a course of intravenous infusions of an antibody comprising a heavy chain variable region comprising the amino acid sequence of SEQ ID NO: 7 and a light chain variable region comprising the amino acid sequence of SEQ ID NO: 8, wherein the antibody specifically binds and inhibits insulin-like growth factor I receptor,
wherein the course of intravenous infusions comprises an initial intravenous infusion of the antibody at a dosage of about 5 mg/kg to about 10 mg/kg and subsequent intravenous infusions of the antibody at a dosage of about 5 mg/kg to about 20 mg/kg, and
wherein after administration of the course of intravenous infusions proptosis is reduced by at least 3 mm.

17. The method of claim 16, wherein the antibody is a human monoclonal antibody.

18. The method of claim 17, wherein the antibody is IgG.

19. The method of claim 18, wherein the antibody is IgG1.

20. The method of claim 19, wherein the antibody is teprotumumab.

21. The method of claim 16, wherein the intravenous infusions are administered every three weeks.

22. The method of claim 21, wherein the course of intravenous infusions consists of 8 intravenous infusions.

23. The method of claim 16, wherein the initial intravenous infusion comprises a dose of about 10 mg/kg of the antibody and the subsequent intravenous infusions comprise a dose of about 20 mg/kg of the antibody.

24. The method of claim 23, wherein the antibody is teprotumumab.

25. The method of claim 23, wherein the subsequent intravenous infusions are administered every three weeks.

26. The method of claim 25, wherein the course of intravenous infusions consists of 8 intravenous infusions.

27. The method of claim 26, wherein the antibody is teprotumumab.

28. A method of reducing proptosis by at least 2 mm in a subject with thyroid eye disease (TED),
comprising administering to the subject an effective amount of an antibody, comprising a heavy chain comprising CDR1, CDR2 and CDR3 and a light chain comprising CDR1, CDR2 and CDR3, as set forth in SEQ ID NOs: 1-6, respectively, wherein the antibody specifically binds and inhibits insulin-like growth factor I receptor (IGF-IR),
wherein the antibody is administered at a dosage of about 5 mg/kg to about 10 mg/kg antibody as a first dose.

* * * * *